United States Patent
Cha et al.

(10) Patent No.: US 11,968,897 B2
(45) Date of Patent: Apr. 23, 2024

(54) HETEROCYCLIC COMPOUND AND ORGANIC LIGHT EMITTING DIODE CONTAINING SAME

(71) Applicant: LG Chem, Ltd., Seoul (KR)

(72) Inventors: Yongbum Cha, Daejeon (KR); Seongmi Cho, Daejeon (KR); Jungbum Kim, Daejeon (KR); Sung Kil Hong, Daejeon (KR); Jiwon Kwak, Daejeon (KR)

(73) Assignee: LG Chem, Ltd., Seoul (KR)

( * ) Notice: Subject to any disclaimer, the term of this patent is extended or adjusted under 35 U.S.C. 154(b) by 580 days.

(21) Appl. No.: 15/758,512

(22) PCT Filed: Feb. 23, 2017

(86) PCT No.: PCT/KR2017/001998
§ 371 (c)(1),
(2) Date: Mar. 8, 2018

(87) PCT Pub. No.: WO2017/146483
PCT Pub. Date: Aug. 31, 2017

(65) Prior Publication Data
US 2018/0261777 A1 Sep. 13, 2018

(30) Foreign Application Priority Data

Feb. 23, 2016 (KR) .................. 10-2016-0021336

(51) Int. Cl.
| | |
|---|---|
| *H10K 85/60* | (2023.01) |
| *C07D 307/91* | (2006.01) |
| *C07D 307/93* | (2006.01) |
| *C07D 405/04* | (2006.01) |
| *C07D 405/10* | (2006.01) |
| *C07D 405/14* | (2006.01) |
| *C07D 409/04* | (2006.01) |
| *C07D 409/14* | (2006.01) |
| *C09K 11/02* | (2006.01) |

(Continued)

(52) U.S. Cl.
CPC ....... *H10K 85/6574* (2023.02); *C07D 307/91* (2013.01); *C07D 307/93* (2013.01); *C07D 405/04* (2013.01); *C07D 405/10* (2013.01); *C07D 405/14* (2013.01); *C07D 409/04* (2013.01); *C07D 409/14* (2013.01); *C09K 11/025* (2013.01); *H10K 85/615* (2023.02); *H10K 85/622* (2023.02); *H10K 85/654* (2023.02); *H10K 85/6572* (2023.02); *H10K 85/6576* (2023.02); *H10K 50/11* (2023.02); *H10K 50/15* (2023.02); *H10K 50/16* (2023.02); *H10K 50/18* (2023.02)

(58) Field of Classification Search
CPC ............ H01L 51/0052; H01L 51/0054; H01L 51/0072; H01L 51/0073; H01L 51/0074; H01L 51/0062; H01L 51/0065; H01L 51/0067; C07D 307/91; C07D 307/93; C07D 307/78; C07D 307/87; C07D 307/77; C07D 405/02; C07D 405/04; C07D 405/10; C07D 409/04; C09K 11/025; H10K 85/615; H10K 85/622; H10K 85/6572; H10K 85/6574; H10K 85/6576; H10K 85/649; H10K 85/653; H10K 85/654
See application file for complete search history.

(56) References Cited

U.S. PATENT DOCUMENTS 9,056,870 B2 6/2015 Kato et al.
2002/0121860 A1* 9/2002 Seo .................. H01L 51/5016
313/506

(Continued)

FOREIGN PATENT DOCUMENTS

| CN | 102056899 A | 5/2011 |
|---|---|---|
| CN | 102056911 A | 5/2011 |

(Continued)

OTHER PUBLICATIONS

Kim et al., Machine translation of KR-20120029751-A (2012) pp. 1-23. (Year: 2012).*

(Continued)

*Primary Examiner* — Dylan C Kershner
(74) *Attorney, Agent, or Firm* — Lerner David LLP

(57) ABSTRACT

The present specification relates to a hetero-cyclic compound represented by the following Chemical Formula 1, and an organic light emitting device including the same. Such hetero-cyclic compound used as a material for an organic material layer of an organic light emitting device improves efficiency, achieves low driving voltage, and/or improves service life characteristics.

[Chemical Formula 1]

wherein R1 to R5, r3 to r5, L1, and Ar1 are defined therein.

13 Claims, 1 Drawing Sheet

(51) Int. Cl.
*H10K 50/11* (2023.01)
*H10K 50/15* (2023.01)
*H10K 50/16* (2023.01)
*H10K 50/18* (2023.01)

(56) References Cited

U.S. PATENT DOCUMENTS

| | | | |
|---|---|---|---|
| 2003/0059647 A1* | 3/2003 | Thompson | C09K 11/06 428/690 |
| 2003/0076032 A1* | 4/2003 | Suzuri | H01L 51/006 313/504 |
| 2004/0251816 A1 | 12/2004 | Leo et al. | |
| 2009/0309488 A1 | 12/2009 | Kato et al. | |
| 2010/0012931 A1 | 1/2010 | Kato et al. | |
| 2012/0104940 A1 | 5/2012 | Shin et al. | |
| 2013/0016191 A1 | 1/2013 | Katayama | |
| 2015/0144938 A1* | 5/2015 | Lee | C07D 405/04 548/440 |
| 2015/0236262 A1 | 8/2015 | Cho et al. | |
| 2015/0280136 A1 | 10/2015 | Ryu et al. | |
| 2015/0349270 A1* | 12/2015 | Lee | H10K 85/6576 546/281.1 |
| 2016/0133851 A1 | 5/2016 | Jo et al. | |
| 2016/0141522 A1 | 5/2016 | Ma et al. | |
| 2016/0351816 A1 | 12/2016 | Kim et al. | |
| 2017/0062734 A1* | 3/2017 | Suzuki | H10K 50/11 |
| 2017/0077416 A1 | 3/2017 | Kim et al. | |
| 2017/0110664 A1* | 4/2017 | Diev | C08G 61/124 |
| 2017/0207397 A1* | 7/2017 | Lee | H05B 33/20 |

FOREIGN PATENT DOCUMENTS

| | | | |
|---|---|---|---|
| CN | 106206999 | A | 12/2016 |
| CN | 106977497 | A | 7/2017 |
| EP | 2301926 | A1 | 3/2011 |
| EP | 03010067 | A1 | 4/2016 |
| EP | 03130591 | A1 | 2/2017 |
| JP | 201321550 | A | 1/2013 |
| JP | 2014028819 | A | 2/2014 |
| JP | 2014224047 | A | 12/2014 |
| JP | 2015534258 | A | 11/2015 |
| KR | 20120029751 | A * | 3/2012 |
| KR | 20120029751 | A | 3/2012 |
| KR | 20120078301 | A | 7/2012 |
| KR | 20140018825 | A | 2/2014 |
| KR | 20140045154 | A | 4/2014 |
| KR | 20140049186 | A | 4/2014 |
| KR | 20150045809 | A | 4/2015 |
| KR | 20150096593 | A | 8/2015 |
| KR | 20150125391 | A | 11/2015 |
| KR | 20160020159 | A | 2/2016 |
| KR | 20160066308 | A | 6/2016 |
| KR | 20160141360 | A | 12/2016 |
| WO | 2009148015 | A1 | 12/2009 |
| WO | 2014061963 | A1 | 4/2014 |
| WO | 2014104514 | A1 | 7/2014 |
| WO | 2014200148 | A1 | 12/2014 |
| WO | 2015023034 | A1 | 2/2015 |
| WO | 2015182887 | A1 | 12/2015 |
| WO | 2016006791 | A1 | 1/2016 |
| WO | 2016068411 | A1 | 5/2016 |
| WO | 2016068450 | A1 | 5/2016 |

OTHER PUBLICATIONS

Ito et al., Machine translation of JP 2014-224047 A (2014) pp. 1-105. (Year: 2014).*
Kim et al., machine translation of KR 10-2012-0029751 A (2012) pp. 1-24. (Year: 2012).*
Search report from International Application No. PCT/KR2017/001998, dated May 31, 2017.
Chinese Search Report for Application No. 201780003030, dated Dec. 3, 2020, 3 pages.

* cited by examiner

[Figure 1]
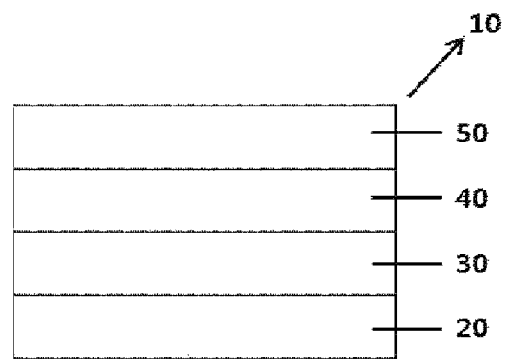
[Figure 2]
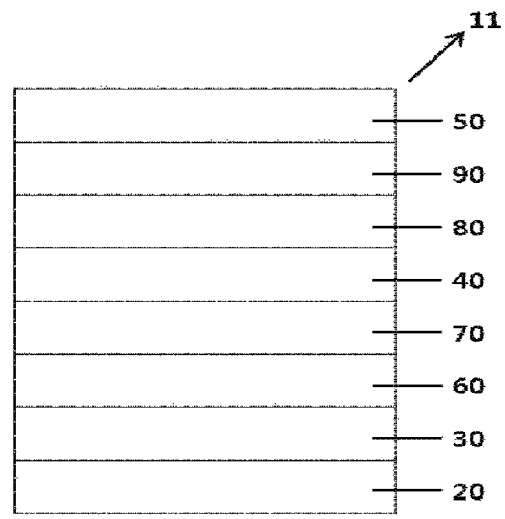

HETEROCYCLIC COMPOUND AND ORGANIC LIGHT EMITTING DIODE CONTAINING SAME

CROSS-REFERENCE TO RELATED APPLICATIONS

The present application is a national phase entry under 35 U.S.C. § 371 of International Application No. PCT/KR2017/001998 filed Feb. 23, 2017, which claims priority from Korean Patent Application No. 10-2016-0021336 filed in the Korean Intellectual Property Office on Feb. 23, 2016, the entire contents of which are incorporated herein by reference.

TECHNICAL FIELD

The present invention claims priority to and the benefit of Korean Patent Application No. 10-2016-0021336 filed in the Korean Intellectual Property Office on Feb. 23, 2016, the entire contents of which are incorporated herein by reference.

The present specification relates to a hetero-cyclic compound and an organic light emitting device including the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have in many cases a multi-layered structure composed of different materials in order to improve the efficiency and stability of an organic light emitting device, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

US Patent Publication No. 2004-0251816

DETAILED DESCRIPTION OF THE INVENTION

Technical Problem

The present specification provides a hetero-cyclic compound and an organic light emitting device including the same.

Technical Solution

An exemplary embodiment of the present specification provides a hetero-cyclic compound represented by the following Chemical Formula 1.

[Chemical Formula 1]

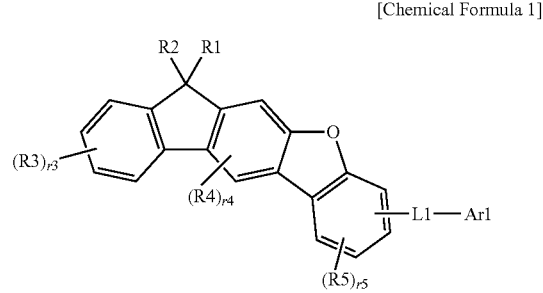

In Chemical Formula 1,
R1 and R2 are the same as or different from each other, and are each independently a substituted or unsubstituted alkyl group,
R3 to R5 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,
L1 is a direct bond; a substituted or unsubstituted monocyclic or bicyclic arylene group; a substituted or unsubstituted phenanthrenylene group; a substituted or unsubstituted phenylenylene group; a substituted or unsubstituted fluorenylene group; a substituted or unsubstituted tetracyclic or more arylene group; or a substituted or unsubstituted heteroarylene group,
Ar1 is a substituted or unsubstituted phosphine oxide group; a substituted or unsubstituted aryl group; or a substituted or unsubstituted heteroaryl group,
r3 is an integer from 1 to 4,
r4 is 1 or 2,
r5 is an integer from 1 to 3, and
when r3 to r5 are each present in a plural number, a plurality of structures in the parenthesis is the same as or different from each other.

Further, an exemplary embodiment of the present specification provides an organic light emitting device including: a first electrode; a second electrode disposed to face the first electrode; and an organic material layer having one or more layers disposed between the first electrode and the second electrode, in which one or more layers of the organic material layer include the hetero-cyclic compound represented by Chemical Formula 1.

Advantageous Effects

The hetero-cyclic compound according to an exemplary embodiment of the present specification may be used as a material for an organic material layer of an organic light emitting device, and it is possible to improve efficiency, achieve low driving voltage, and/or improve service life characteristics in the organic light emitting device by using the same.

BRIEF DESCRIPTION OF DRAWINGS

FIG. 1 illustrates an organic light emitting device 10 according to an exemplary embodiment of the present specification.

FIG. 2 illustrates an organic light emitting device 11 according to another exemplary embodiment of the present specification.

BEST MODE

Hereinafter, the present specification will be described in more detail.

The present specification provides the hetero-cyclic compound represented by Chemical Formula 1.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with the another member, but also a case where still another member is present between the two members.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a nitrile group; a nitro group; an imide group; an amide group; a carbonyl group; an ester group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted hetero-cyclic group or being substituted with a substituent to which two or more substituents are linked among the substituents exemplified above, or having no substituent. For example, "the substituent to which two or more substituents are linked" may be a biphenyl group. That is, the biphenyl group may also be an aryl group, and may be interpreted as a substituent to which two phenyl groups are linked.

In the present specification,

means a moiety bonded to another substituent or a bonding portion.

In the present specification, a halogen group may be fluorine, chlorine, bromine, or iodine.

In the present specification, the number of carbon atoms of an imide group is not particularly limited, but is preferably 1 to 30. Specifically, the imide group may be a compound having the following structures, but is not limited thereto.

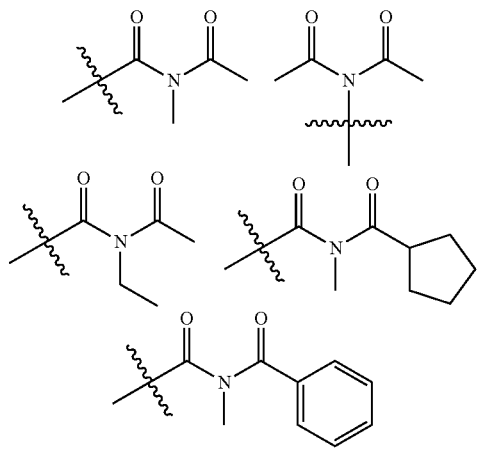

In the present specification, for an amide group, the nitrogen of the amide group may be substituted with hydrogen, a straight, branched, or cyclic alkyl group having 1 to 30 carbon atoms, or an aryl group having 6 to 30 carbon atoms. Specifically, the amide group may be a compound having the following structural formulae, but is not limited thereto.

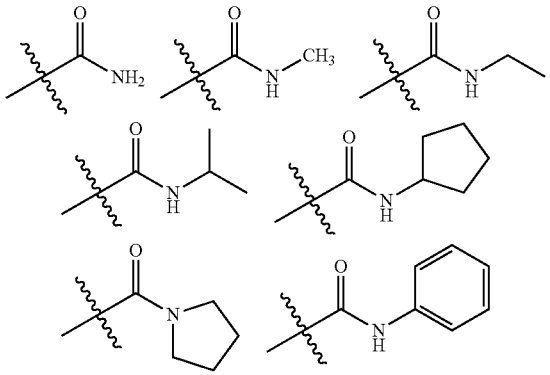

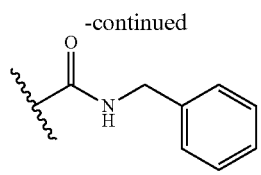

In the present specification, the number of carbon atoms of a carbonyl group is not particularly limited, but is preferably 1 to 30. Specifically, the carbonyl group may be a compound having the following structures, but is not limited thereto.

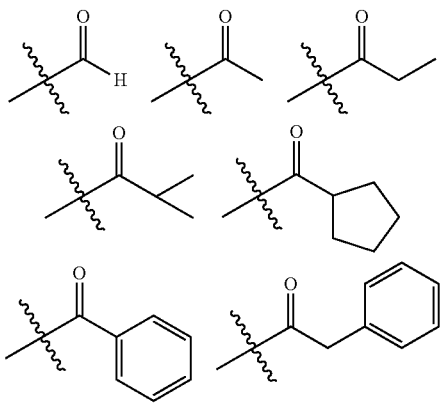

In the present specification, for an ester group, the oxygen of the ester group may be substituted with a straight, branched, or cyclic alkyl group having 1 to 25 carbon atoms, or an aryl group having 6 to 30 carbon atoms. Specifically, the ester group may be a compound having the following structural formulae, but is not limited thereto.

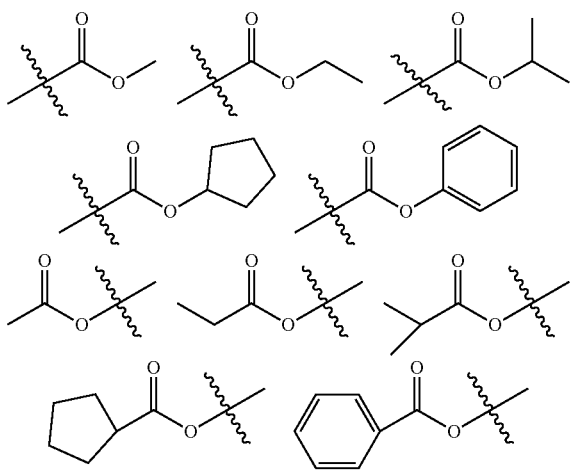

In the present specification, the alkyl group may be straight or branched, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but has preferably 3 to 30 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight, branched, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, an amine group may be selected from the group consisting of —$NH_2$; an alkylamine group; an N-alkylarylamine group; an arylamine group; an N-arylheteroarylamine group; an N-alkylheteroarylamine group; and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenyl terphenylamine group; an N-phenanthrenylfluorenylamine group; an N-biphenylfluorenylamine group, and the like, but are not limited thereto.

In the present specification, an N-alkylarylamine group means an amine group in which an alkyl group and an aryl group are substituted with N of the amine group.

In the present specification, an N-arylheteroarylamine group means an amine group in which an aryl group and a heteroaryl group are substituted with N of the amine group.

In the present specification, an N-alkylheteroarylamine group means an amine group in which an alkyl group and a heteroaryl group are substituted with N of the amine group.

In the present specification, the alkyl group in the alkylamine group, the N-arylalkylamine group, the alkylthioxy group, the alkylsulfoxy group, and the N-alkylheteroarylamine group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but the examples are not limited thereto.

In the present specification, the alkenyl group may be straight or branched, and the number of carbon atoms thereof is not particularly limited, but is preferably 2 to 30.

Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be $-BR_{100}R_{101}$, and $R_{100}$ and $R_{101}$ are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted straight or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of a phosphine oxide group include a diphenylphosphine oxide group, dinaphthylphosphine oxide group, and the like, but are not limited thereto.

In the present specification, an aryl group is not particularly limited, but has preferably 6 to 30 carbon atoms, and the aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a triphenyl group, a pyrenyl group, a phenalenyl group, a perylenyl group, a chrysenyl group, a fluorenyl group, and the like, but are not limited thereto.

In the present specification, the fluorenyl group may be substituted, and adjacent substituents may be bonded to each other to form a ring.

When the fluorenyl group is substituted, the fluorenyl group may be

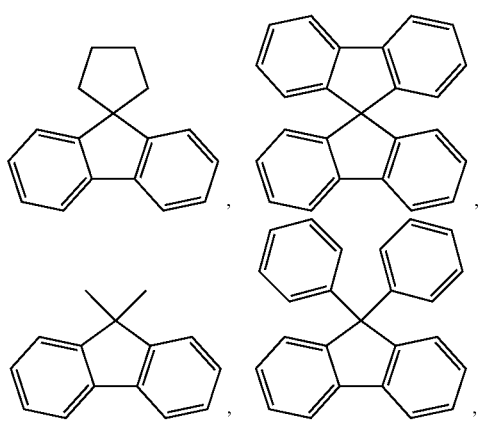

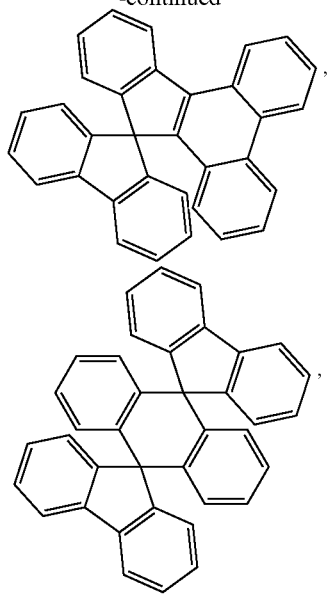

and the like.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the aryl group in the aryloxy group, the arylthioxy group, the arylsulfoxy group, the N-arylalkylamine group, the N-arylheteroarylamine group, and the arylphosphine group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group. For example, the aryl group in the arylamine group may be selected from the above-described examples of the aryl group.

In the present specification, a heteroaryl group includes one or more atoms other than carbon, that is, one or more heteroatoms, and specifically, the heteroatom may include one or more atoms selected from the group consisting of O, N, Se, and S, and the like. The number of carbon atoms thereof is not particularly limited, but is preferably 2 to 30, and the heteroaryl group may be monocyclic or polycyclic. Examples of a hetero-cyclic group include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group (phenanthroline), an isoxazolyl group, a thiadiazolyl group, a phenothiazinyl group, a dibenzofuranyl group, and the like, but are not limited thereto.

In the present specification, examples of a heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include a monocyclic heteroaryl group, a polycyclic heteroaryl group, or both a monocyclic heteroaryl group and a polycyclic heteroaryl group. For example, the heteroaryl group in the heteroarylamine group may be selected from the above-described examples of the heteroaryl group.

In the present specification, examples of the heteroaryl group in the N-arylheteroarylamine group and the N-alkylheteroarylamine group are the same as the above-described examples of the heteroaryl group.

In the present specification, an arylene group means a group having two bonding positions in an aryl group, that is, a divalent group. The above-described description on the aryl group may be applied to the arylene group, except for a divalent arylene group.

In the present specification, a heteroarylene group means a group having two bonding positions in a heteroaryl group, that is, a divalent group. The above-described description on the heteroaryl group may be applied to the heteroarylene group, except for a divalent heteroarylene group.

In the present specification, in a substituted or unsubstituted ring formed by bonding adjacent groups, the "ring" means a substituted or unsubstituted hydrocarbon ring; or a substituted or unsubstituted hetero ring.

In the present specification, a ring means a substituted or unsubstituted hydrocarbon ring; or a substituted or unsubstituted hetero ring.

In the present specification, a hydrocarbon ring may be an aromatic ring, an aliphatic ring, or a fused ring of the aromatic ring and the aliphatic ring, and may be selected from the examples of the cycloalkyl group or the aryl group, except for the hydrocarbon ring which is not monovalent.

In the present specification, an aromatic ring may be monocyclic or polycyclic, and may be selected from the examples of the aryl group, except for the aromatic ring which is not monovalent.

In the present specification, a hetero ring includes one or more atoms other than carbon, that is, one or more heteroatoms, and specifically, the heteroatom may include one or more atoms selected from the group consisting of O, N, Se, and S, and the like. The hetero ring may be monocyclic or polycyclic, may be an aromatic ring, an aliphatic ring, or a fused ring of the aromatic ring and the aliphatic ring, and may be selected from the examples of the heteroaryl group or the heterocyclic group, except for the hetero ring which is not monovalent.

According to an exemplary embodiment of the present specification, Chemical Formula 1 is represented by any one of the following Chemical Formulae 2 to 5.

[Chemical Formula 2]

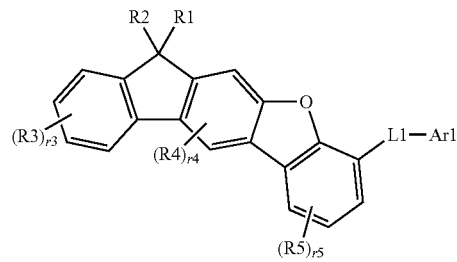

[Chemical Formula 3]

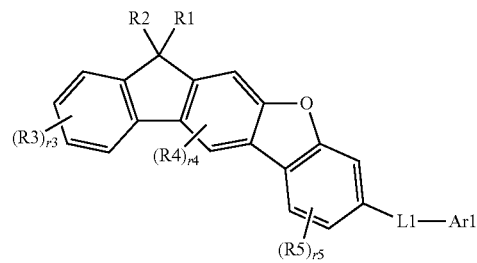

[Chemicl Formula 4]

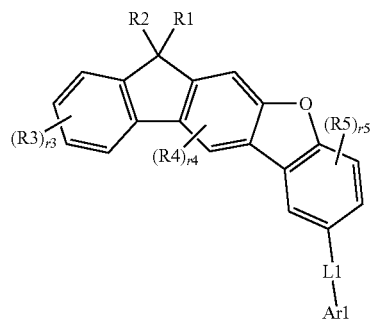

[Chemical Formula 5]

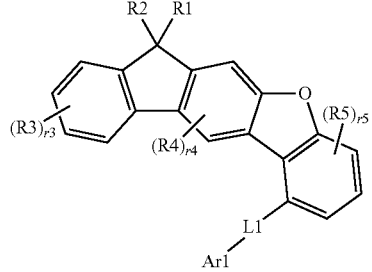

In Chemical Formulae 2 to 5, the definitions of R1 to R5, r3 to r5, L1, and Ar1 are the same as those in Chemical Formula 1.

According to an exemplary embodiment of the present specification, in Chemical Formula 1, R1 and R2 are the same as or different from each other, and are each independently an alkyl group.

According to an exemplary embodiment of the present specification, in Chemical Formula 1, R1 and R2 are the same as or different from each other, and are each independently a methyl group.

According to an exemplary embodiment of the present specification, Chemical Formula 1 is represented by the following Chemical Formula 6.

[Chemical Formula 6]

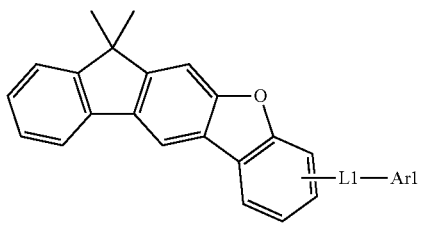

In Chemical Formula 6,
the definitions of L1 and Ar1 are the same as those in Chemical Formula 1.

According to an exemplary embodiment of the present specification, Chemical Formula 1 is represented by any one of the following Chemical Formulae 7 to 10.

[Chemical Formula 7]

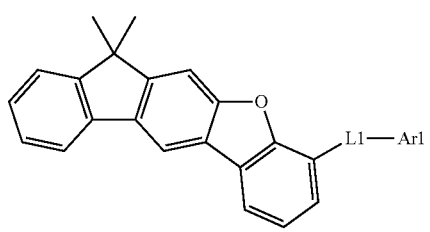

[Chemical Formula 8]

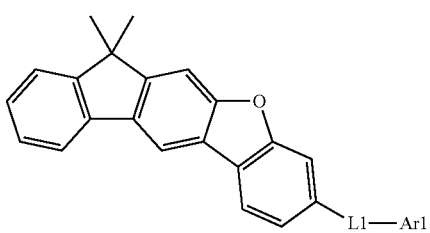

[Chemical Formula 9]

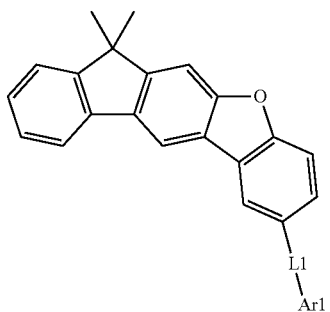

[Chemical Formula 10]

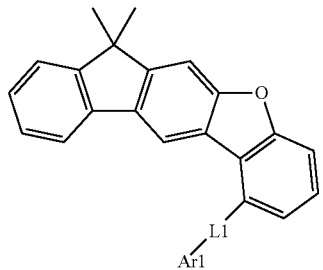

In Chemical Formulae 7 to 10,
the definitions of L1 and Ar1 are the same as those in Chemical Formula 1.

According to an exemplary embodiment of the present specification, in Chemical Formula 1, L1 is a direct bond; a substituted or unsubstituted monocyclic or bicyclic arylene group; a substituted or unsubstituted phenanthrenylene group; a substituted or unsubstituted phenylenylene group; a substituted or unsubstituted fluorenylene group; a substituted or unsubstituted tetracyclic or more arylene group; or a substituted or unsubstituted heteroarylene group.

According to an exemplary embodiment of the present specification, in Chemical Formula 1, L1 is a direct bond; a monocyclic or bicyclic arylene group; a phenanthrenylene group; a phenylenylene group; a fluorenylene group; a tetracyclic or more arylene group; or a heteroarylene group.

According to an exemplary embodiment of the present specification, in Chemical Formula 1, L1 is a direct bond.

According to an exemplary embodiment of the present specification, in Chemical Formula 1, L1 is a monocyclic or bicyclic arylene group having 6 to 20 carbon atoms.

According to an exemplary embodiment of the present specification, in Chemical Formula 1, L1 is a phenylene group, a biphenylene group, and a naphthylene group.

According to an exemplary embodiment of the present specification, in Chemical Formula 1, L1 is a polycyclic arylene group having 10 to 30 carbon atoms.

According to an exemplary embodiment of the present specification, in Chemical Formula 1, L1 is a terphenylene group, a fluorenylene group, a phenanthrenylene group, a quarterphenylene group, a pyrenylene group, or a triphenylene group.

According to an exemplary embodiment of the present specification, in Chemical Formula 1, L1 is a substituted or unsubstituted heteroarylene group including N.

According to an exemplary embodiment of the present specification, in Chemical Formula 1, L1 is a substituted or unsubstituted heteroarylene group having 5 to 20 carbon atoms, including N.

According to an exemplary embodiment of the present specification, in Chemical Formula 1, L1 is a carbazolene group.

According to an exemplary embodiment of the present invention, in Chemical Formula 1, L1 is a direct bond; a substituted or unsubstituted phenylene group; a substituted or unsubstituted biphenylylene group; a substituted or unsubstituted naphthylene group; a substituted or unsubstituted terphenylene group; a substituted or unsubstituted quarterphenylene group; a substituted or unsubstituted fluorenylene group; a substituted or unsubstituted phenanthrenylene group; a substituted or unsubstituted pyrenylene group; a substituted or unsubstituted triphenylenylene group; or a substituted or unsubstituted carbazolylene group.

According to an exemplary embodiment of the present specification, in Chemical Formula 1, L1 is a direct bond; a phenylene group; a biphenylylene group; a naphthylene group; a terphenylene group; a quarterphenylene group; a fluorenylene group; a phenanthrenylene group; a pyrenylene group; a triphenylenylene group; or a carbazolylene group.

According to an exemplary embodiment of the present specification, in Chemical Formula 1, L1 may be any one of the following structures, but is not limited thereto.

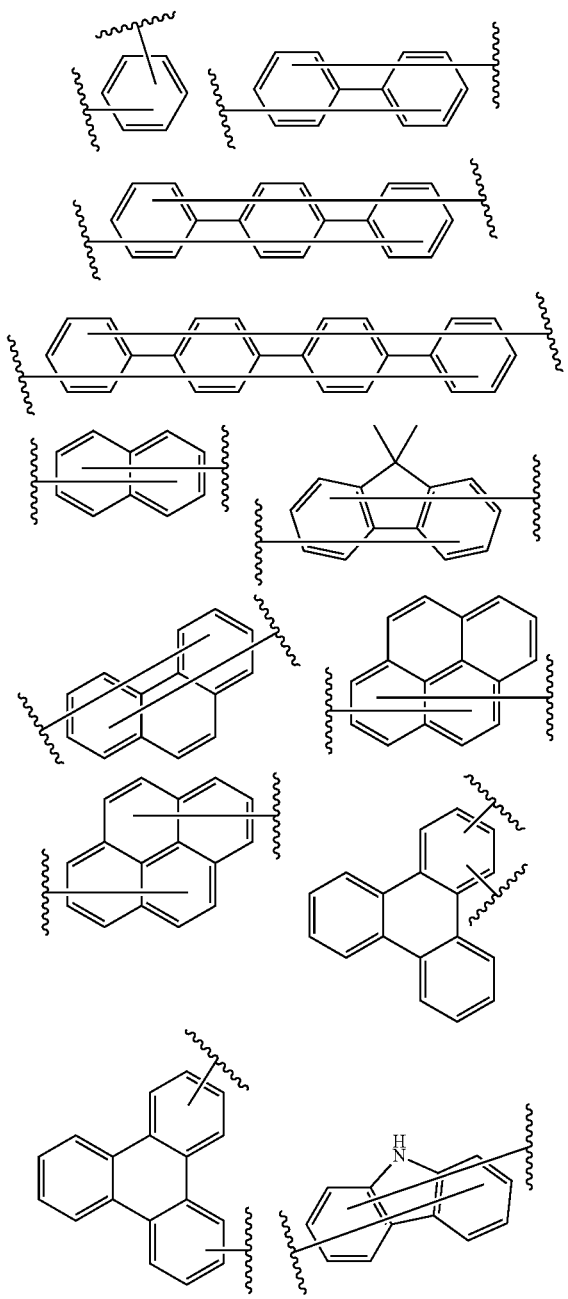

According to an exemplary embodiment of the present specification, in Chemical Formula 1, L1 is a direct bond; a phenylene group; or a carbazolylene group.

According to an exemplary embodiment of the present specification, in Chemical Formula 1, Ar1 is selected from the group consisting of a substituted or unsubstituted silyl group; a substituted or unsubstituted phosphine oxide group; a substituted or unsubstituted aryl group; and a substituted or unsubstituted heteroaryl group.

According to an exemplary embodiment of the present specification, in Chemical Formula 1, Ar1 is selected from the group consisting of a substituted or unsubstituted phenyl group; a substituted or unsubstituted biphenyl group; a substituted or unsubstituted phenanthrenyl group; a substituted or unsubstituted naphthyl group; a substituted or unsubstituted terphenyl group; a substituted or unsubstituted fluorenyl group; a substituted or unsubstituted anthracenyl group; a substituted or unsubstituted chrysenyl group; a substituted or unsubstituted quarterphenyl group; a substituted or unsubstituted spirobifluorenyl group; a substituted or unsubstituted pyrenyl group; a substituted or unsubstituted triphenylenyl group; a substituted or unsubstituted perylenyl group; a substituted or unsubstituted triazinyl group; a substituted or unsubstituted pyrimidyl group; a substituted or unsubstituted pyridyl group; a substituted or unsubstituted quinolinyl group; a substituted or unsubstituted quinazolinyl group; a substituted or unsubstituted benzoquinolinyl group; a substituted or unsubstituted phenanthrolinyl group; a substituted or unsubstituted quinoxalinyl group; a substituted or unsubstituted dibenzofuranyl group; a substituted or unsubstituted dibenzothiophene group; a substituted or unsubstituted benzonaphthofuranyl group; a substituted or unsubstituted benzonaphthothiophene group; a substituted or unsubstituted dimethylphosphine oxide group; a substituted or unsubstituted diphenylphosphine oxide group; a substituted or unsubstituted dinaphthylphosphine oxide group; a substituted or unsubstituted benzoxazolyl group; a substituted or unsubstituted benzothiazolyl group; a substituted or unsubstituted benzimidazolyl group; a substituted or unsubstituted triphenylsilyl group; a substituted or unsubstituted phenothiazinyl group; a substituted or unsubstituted phenoxazinyl group; a substituted or unsubstituted thiophene group; a substituted or unsubstituted benzocarbazolyl group; a substituted or unsubstituted dibenzocarbazolyl group; a substituted or unsubstituted carbazolyl group; a substituted or unsubstituted

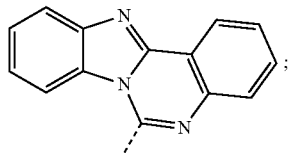

a substituted or unsubstituted

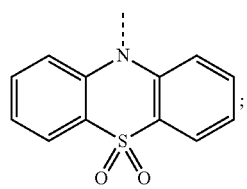

and a structure represented by the following Chemical Formula a, and

---- means a moiety bonded to Chemical Formula 1 via L1.

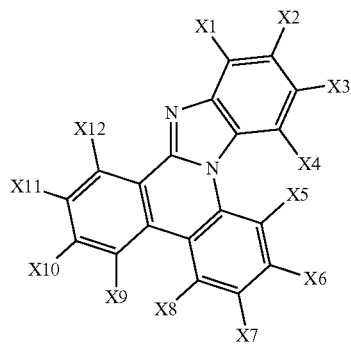

[Chemical Formula a]

In Chemical Formula a,
any one of X1 to X12 is a moiety bonded to Chemical Formula 1 via L1, and the others are the same as or different from each other, and are each independently hydrogen; a substituted or unsubstituted alkyl group; a substituted or unsubstituted aryl group; or a substituted or unsubstituted heteroaryl group, or adjacent groups are linked to each other to form a substituted or unsubstituted ring.

According to an exemplary embodiment of the present specification, in Chemical Formula a, any one of X1 to X12 is a moiety bonded to Chemical Formula 1 via L1, and the others are hydrogen.

According to an exemplary embodiment of the present specification, in Chemical Formula a, X11 and X12 are linked to each other to form a substituted or unsubstituted monocyclic or polycyclic hydrocarbon ring having 6 to 20 carbon atoms.

According to an exemplary embodiment of the present specification, in Chemical Formula a, X11 and X12 are linked to each other to form a substituted or unsubstituted monocyclic or polycyclic hydrocarbon ring having 6 to 10 carbon atoms.

According to an exemplary embodiment of the present specification, in Chemical Formula a, X11 and X12 are linked to each other to form a substituted or unsubstituted benzene ring.

According to an exemplary embodiment of the present specification, in Chemical Formula a, X11 and X12 are linked to each other to form a benzene ring.

According to an exemplary embodiment of the present specification, in Chemical Formula 1, Ar1 is selected from the group consisting of a phenyl group; a biphenyl group; a phenanthrenyl group; a naphthyl group; a terphenyl group; a fluorenyl group; an anthracenyl group; a chrysenyl group; a quarterphenyl group; a spirobifluorenyl group; a pyrenyl group; a triphenylenyl group; a perylenyl group; a triazinyl group; a pyrimidyl group; a pyridyl group; a quinolinyl group; a quinazolinyl group; a benzoquinolinyl group; a phenanthrolinyl group; a quinoxalinyl group; a dibenzofuranyl group; a dibenzothiophene group; benzonaphthofuranyl group; a benzonaphthothiophene group; a dimethylphosphine oxide group; diphenylphosphine oxide group; dinaphthylphosphine oxide group; a benzoxazolyl group; a benzothiazolyl group; a benzimidazolyl group; a triphenylsilyl group; a phenothiazinyl group; a phenoxazinyl group; a thiophene group; a benzocarbazolyl group; a dibenzocarbazolyl group; a carbazolyl group;

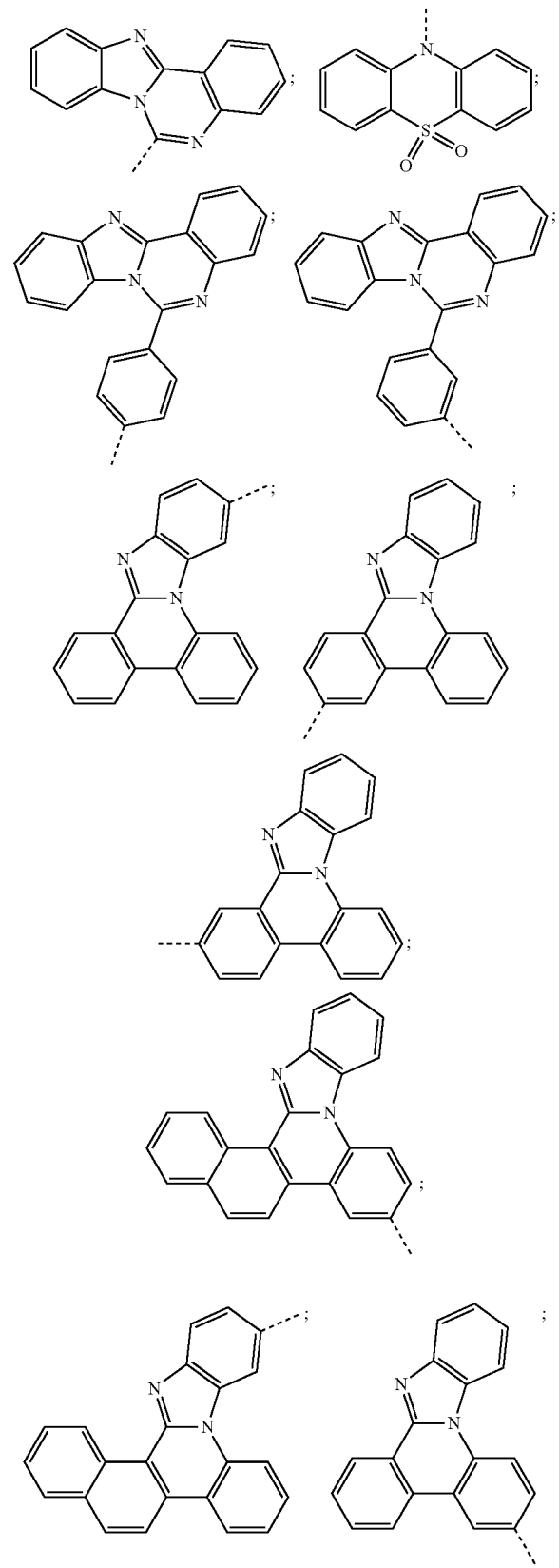

-continued

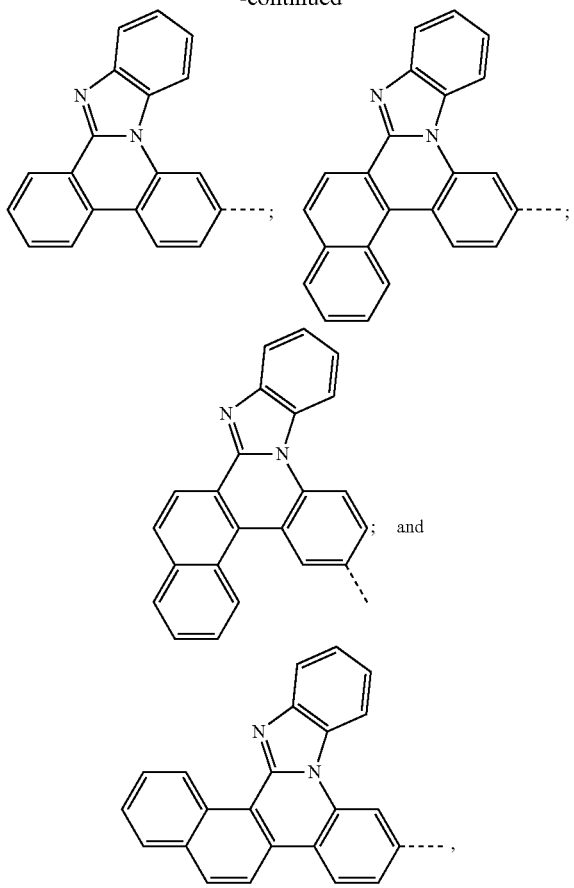

and

Ar1 may be unsubstituted or substituted with one or more selected from the group consisting of deuterium; a fluorine group; a nitrile group; a methyl group; a t-butyl group; a phenyl group; a biphenyl group; a naphthyl group; a fluorenyl group; a phenanthrenyl group; a carbazolyl group; a benzocarbazolyl group; a pyridyl group; a triazinyl group; a triphenylenyl group; a pyrimidyl group; a quinolinyl group; a dibenzofuranyl group; a dibenzothiophene group; a benzimidazolyl group; a benzothiazolyl group; a benzoxazolyl group; a thiophene group; a dimethylphosphine oxide group; a diphenylphosphine oxide group; a dinaphthylphosphine oxide group; a trimethylsilyl group; a triphenylsilyl group; and

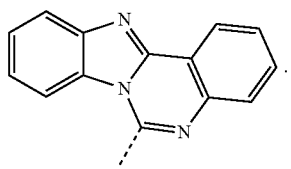

According to an exemplary embodiment of the present specification, in Chemical Formula 1, Ar1 is a substituted or unsubstituted phosphine oxide group; a substituted or unsubstituted aryl group; or a substituted or unsubstituted heteroaryl group.

According to an exemplary embodiment of the present specification, in Chemical Formula 1, Ar1 is a substituted or unsubstituted phosphine oxide group.

According to an exemplary embodiment of the present specification, in Chemical Formula 1, Ar1 is a phosphine oxide group which is unsubstituted or substituted with an aryl group.

According to an exemplary embodiment of the present specification, in Chemical Formula 1, Ar1 is a phosphine oxide group which is unsubstituted or substituted with a monocyclic aryl group.

According to an exemplary embodiment of the present specification, in Chemical Formula 1, Ar1 is a phosphine oxide group which is unsubstituted or substituted with a monocyclic aryl group having 6 to 10 carbon atoms.

According to an exemplary embodiment of the present specification, in Chemical Formula 1, Ar1 is a phosphine oxide group which is unsubstituted or substituted with a phenyl group.

According to an exemplary embodiment of the present specification, in Chemical Formula 1, Ar1 is a phosphine oxide group which is unsubstituted or substituted with a phenyl group.

According to an exemplary embodiment of the present specification, in Chemical Formula 1, Ar1 is a substituted or unsubstituted aryl group.

According to an exemplary embodiment of the present specification, in Chemical Formula 1, Ar1 is a substituted or unsubstituted monocyclic or polycyclic aryl group.

According to an exemplary embodiment of the present specification, in Chemical Formula 1, Ar1 is a substituted or unsubstituted monocyclic or polycyclic aryl group having 6 to 20 carbon atoms.

According to an exemplary embodiment of the present specification, in Chemical Formula 1, Ar1 is a monocyclic or polycyclic aryl group having 6 to 20 carbon atoms, which is unsubstituted or substituted with an alkyl group.

According to an exemplary embodiment of the present specification, in Chemical Formula 1, Ar1 is a naphthalene group, a phenanthrene group, a triphenylene group, or a dimethylfluorene group.

According to an exemplary embodiment of the present specification, in Chemical Formula 1, Ar1 is a substituted or unsubstituted heteroaryl group.

According to an exemplary embodiment of the present specification, in Chemical Formula 1, Ar1 is a substituted or unsubstituted N-containing heteroaryl group.

According to an exemplary embodiment of the present specification, in Chemical Formula 1, Ar1 is a substituted or unsubstituted N-containing heteroaryl group having 3 to 20 carbon atoms.

According to an exemplary embodiment of the present specification, in Chemical Formula 1, Ar1 is a substituted or unsubstituted monocyclic N-containing heteroaryl group having 3 to 10 carbon atoms.

According to an exemplary embodiment of the present specification, in Chemical Formula 1, Ar1 is a monocyclic N-containing heteroaryl group having 3 to 10 carbon atoms, which is unsubstituted or substituted with an aryl group.

According to an exemplary embodiment of the present specification, in Chemical Formula 1, Ar1 is a monocyclic N-containing heteroaryl group having 3 to 10 carbon atoms, which is unsubstituted or substituted with an aryl group having 6 to 20 carbon atoms.

According to an exemplary embodiment of the present specification, in Chemical Formula 1, Ar1 is a pyridine group, a pyrimidine group, or a triazine group, and the pyridine group, the pyrimidine group, or the triazine group is unsubstituted or substituted with a substituted or unsubstituted aryl group having 6 to 20 carbon atoms.

According to an exemplary embodiment of the present specification, in Chemical Formula 1, Ar1 is a pyridine group, a pyrimidine group, or a triazine group, and the pyridine group, the pyrimidine group, or the triazine group is unsubstituted or substituted with a phenyl group or a biphenyl group.

According to an exemplary embodiment of the present specification, in Chemical Formula 1, Ar1 is a pyridine group, a pyrimidine group, or a triazine group, and the pyridine group, the pyrimidine group, or the triazine group is unsubstituted or substituted with an aryl group having 6 to 20 carbon atoms, which is substituted with an alkyl group.

According to an exemplary embodiment of the present specification, in Chemical Formula 1, Ar1 is a pyridine group, a pyrimidine group, or a triazine group, and the pyridine group, the pyrimidine group, or the triazine group is unsubstituted or substituted with a dimethylfluorene group.

According to an exemplary embodiment of the present specification, in Chemical Formula 1, Ar1 is a pyridine group, a pyrimidine group, or a triazine group, and the pyridine group, the pyrimidine group, or the triazine group is unsubstituted or substituted with a heteroaryl group.

According to an exemplary embodiment of the present specification, in Chemical Formula 1, Ar1 is a pyridine group, a pyrimidine group, or a triazine group, and the pyridine group, the pyrimidine group, or the triazine group is unsubstituted or substituted with a heteroaryl group containing 0 or S.

According to an exemplary embodiment of the present specification, in Chemical Formula 1, Ar1 is a pyridine group, a pyrimidine group, or a triazine group, and the pyridine group, the pyrimidine group, or the triazine group is unsubstituted or substituted with a dibenzofuran group or a dibenzothiophene group.

According to an exemplary embodiment of the present specification, in Chemical Formula 1, Ar1 is a substituted or unsubstituted polycyclic N-containing heteroaryl group having 6 to 20 carbon atoms.

According to an exemplary embodiment of the present specification, in Chemical Formula 1, Ar1 is a polycyclic N-containing heteroaryl group having 6 to 20 carbon atoms, and the polycyclic N-containing heteroaryl group having 6 to 20 carbon atoms is unsubstituted or substituted with an aryl group which is unsubstituted or substituted with an alkyl group, or a heteroaryl group.

According to an exemplary embodiment of the present specification, in Chemical Formula 1, Ar1 is a carbazole group, a benzocarbazole group, or a quinazoline group, and the carbazole group, the benzocarbazole group, or the quinazoline group is unsubstituted or substituted with an aryl group which is unsubstituted or substituted with an alkyl group, or a heteroaryl group.

According to an exemplary embodiment of the present specification, in Chemical Formula 1, Ar1 is a carbazole group, a benzocarbazole group, or a quinazoline group, and the carbazole group, the benzocarbazole group, or the quinazoline group is unsubstituted or substituted with a phenyl group, a biphenyl group, a naphthyl group, a dimethylfluorene group, or a dibenzofuran group.

According to an exemplary embodiment of the present specification, in Chemical Formula 1, Ar1 is a carbazole group, and in the carbazole group, a phenyl group, a biphenyl group, or a naphthyl group is unsubstituted or substituted with N of the carbazole.

---- means a moiety bonded to Chemical Formula 1 via L1.

According to an exemplary embodiment of the present specification, in Chemical Formula 1, Ar1 is represented by any one of the following Structural Formulae [A-1] to [A-4].

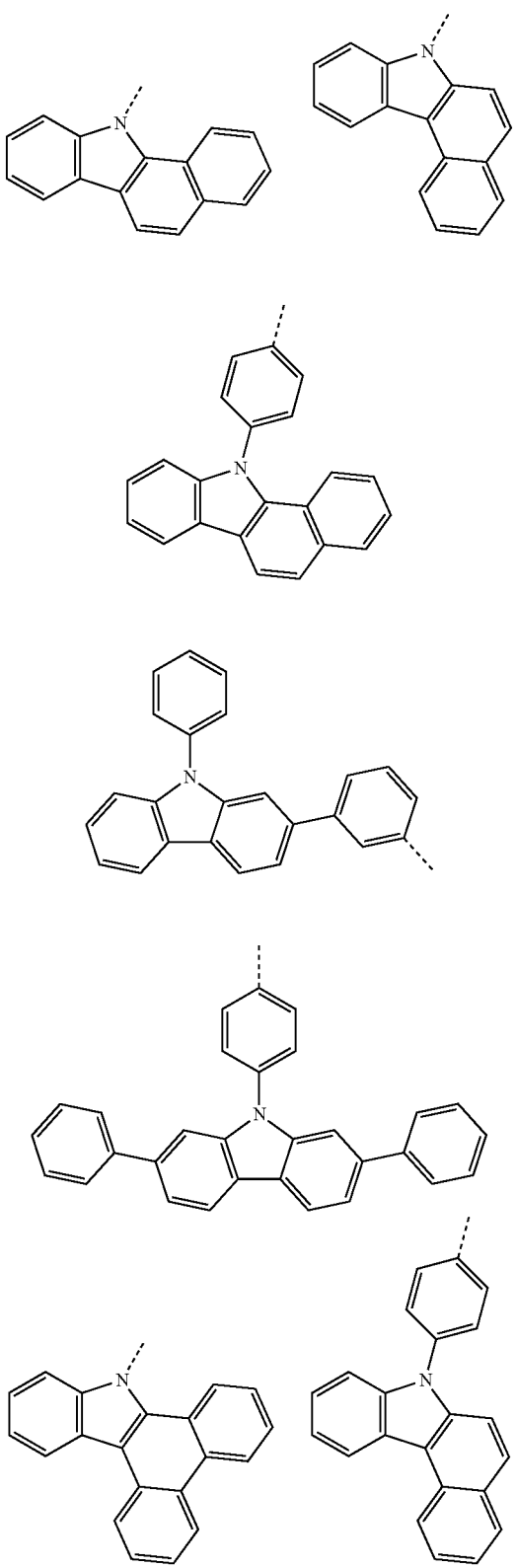

[A-1]

-continued
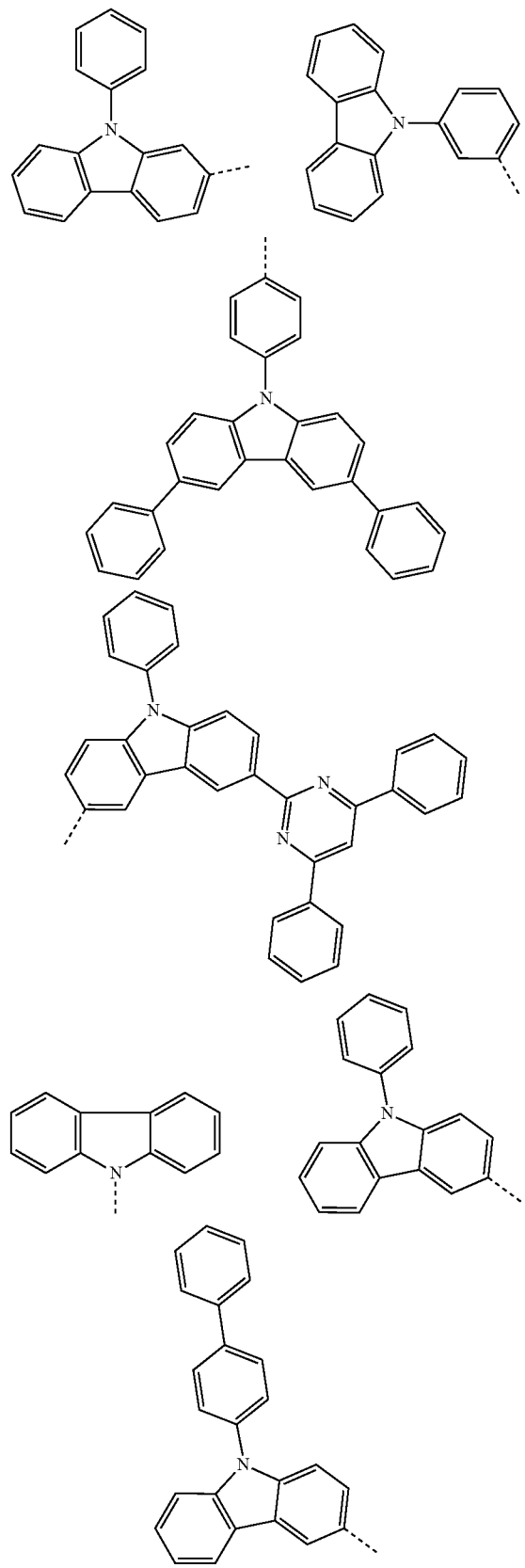
-continued
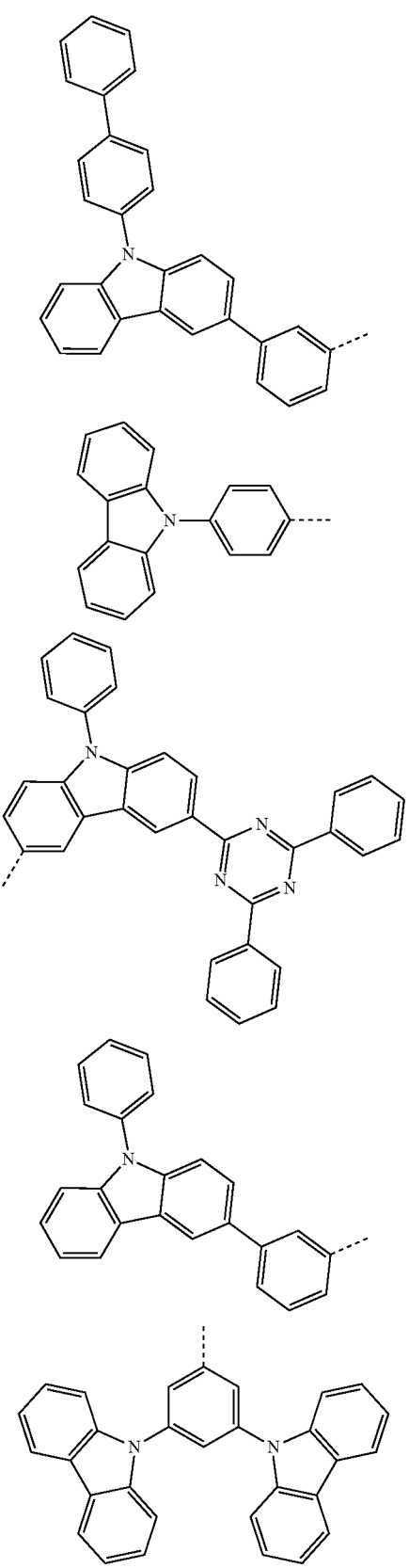

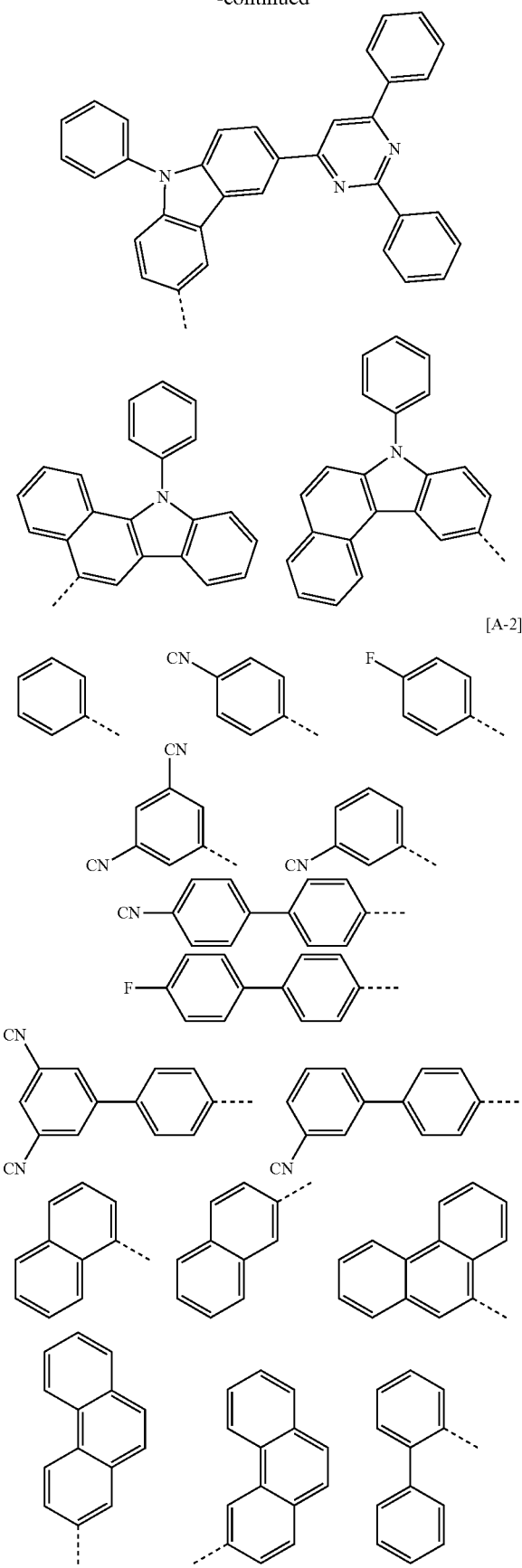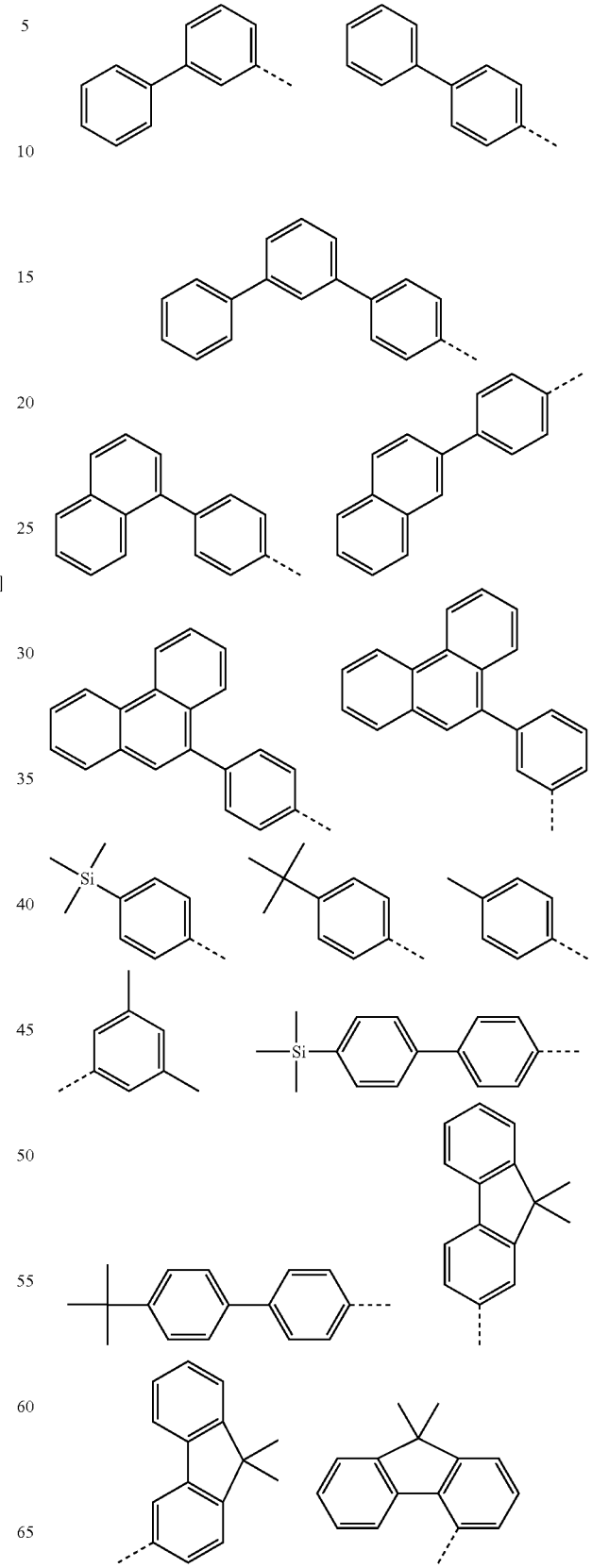

-continued
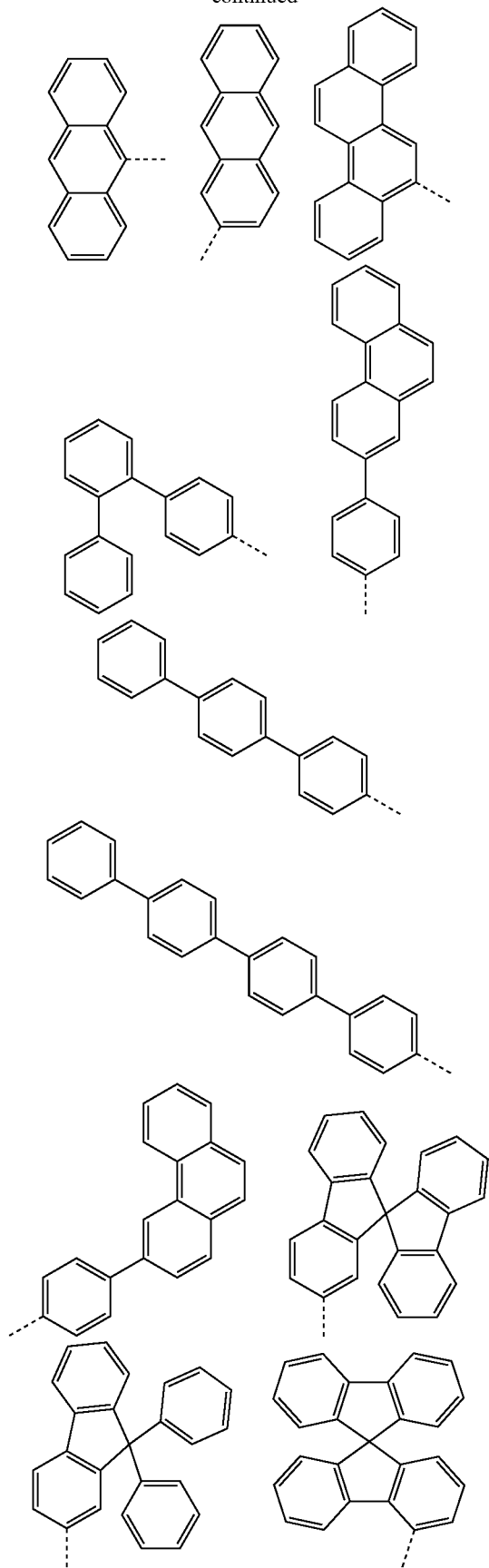
-continued
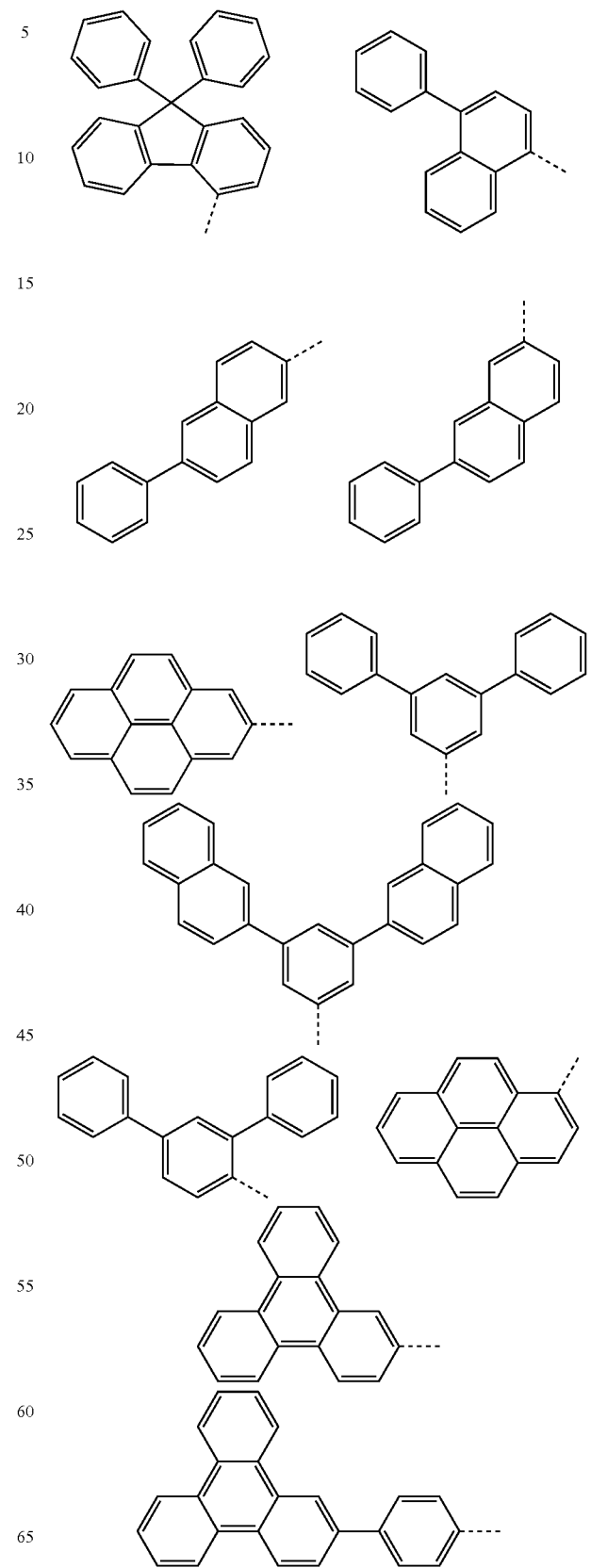

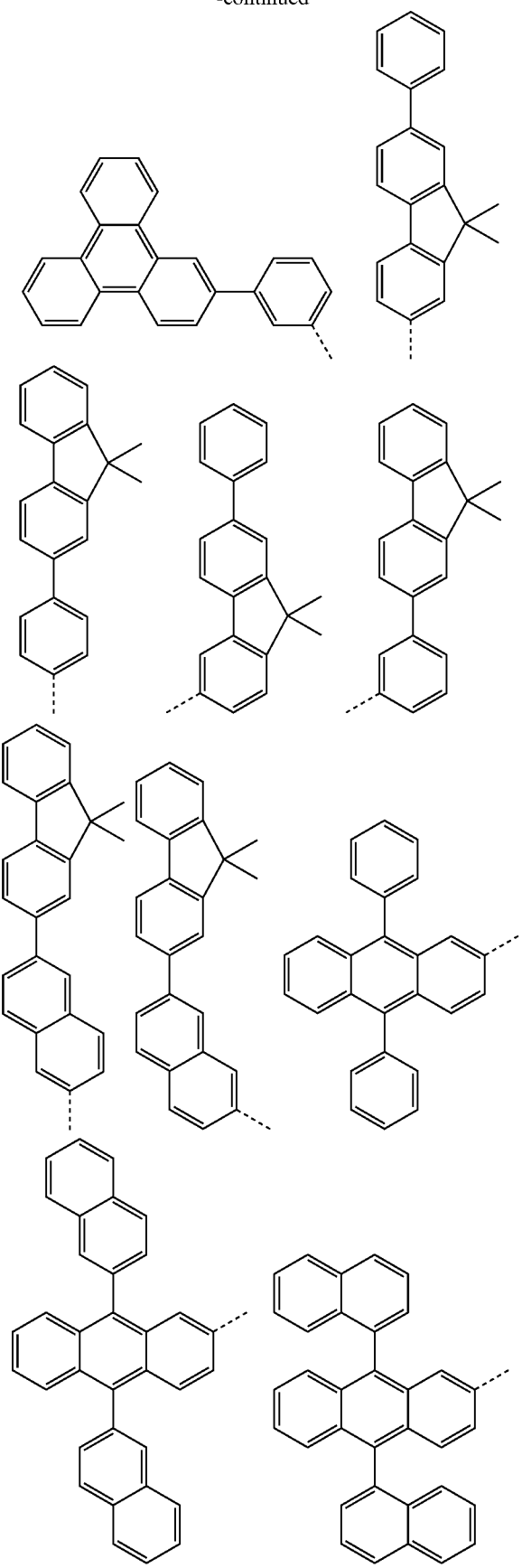
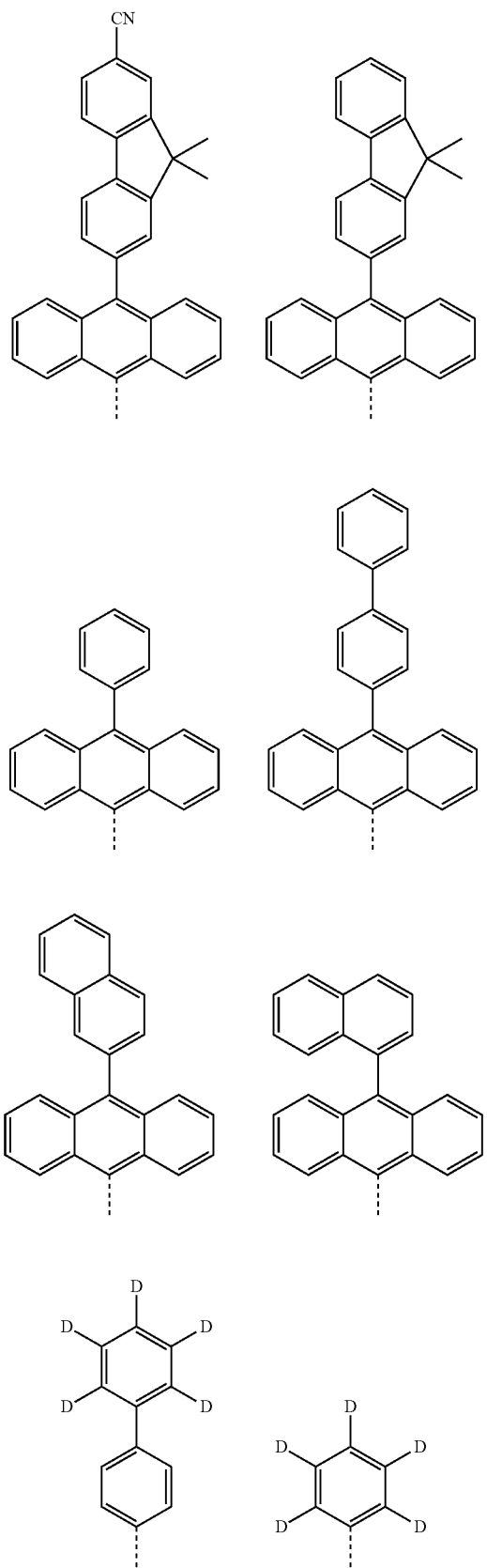

29
-continued
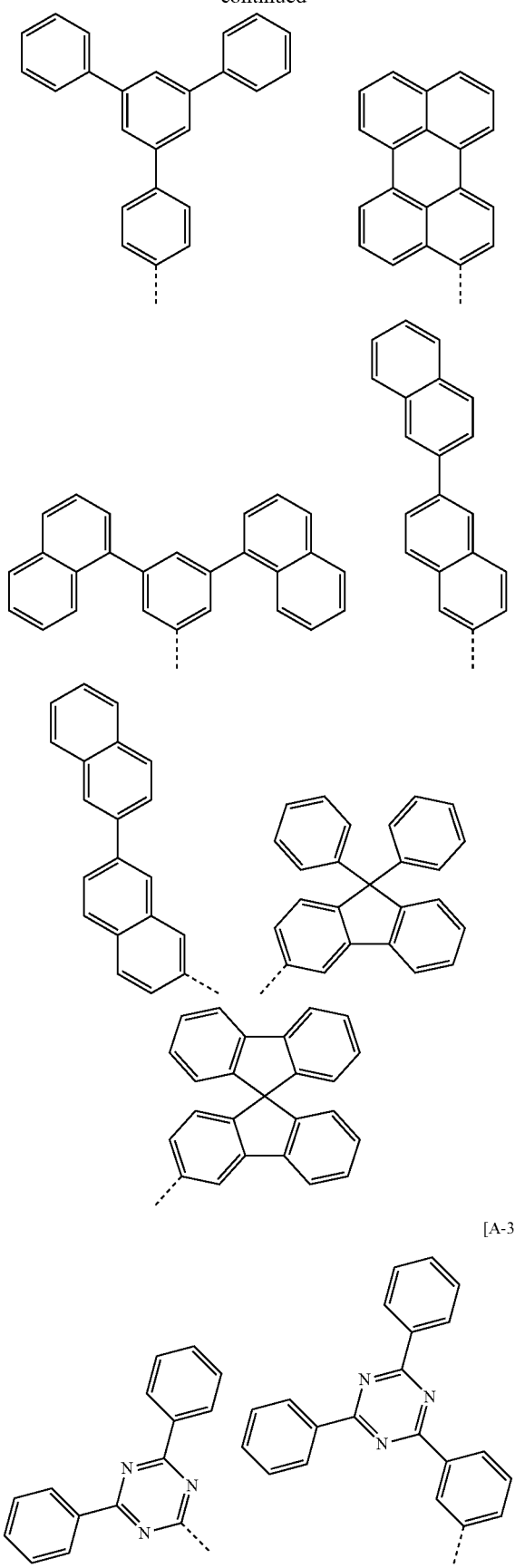
30
-continued
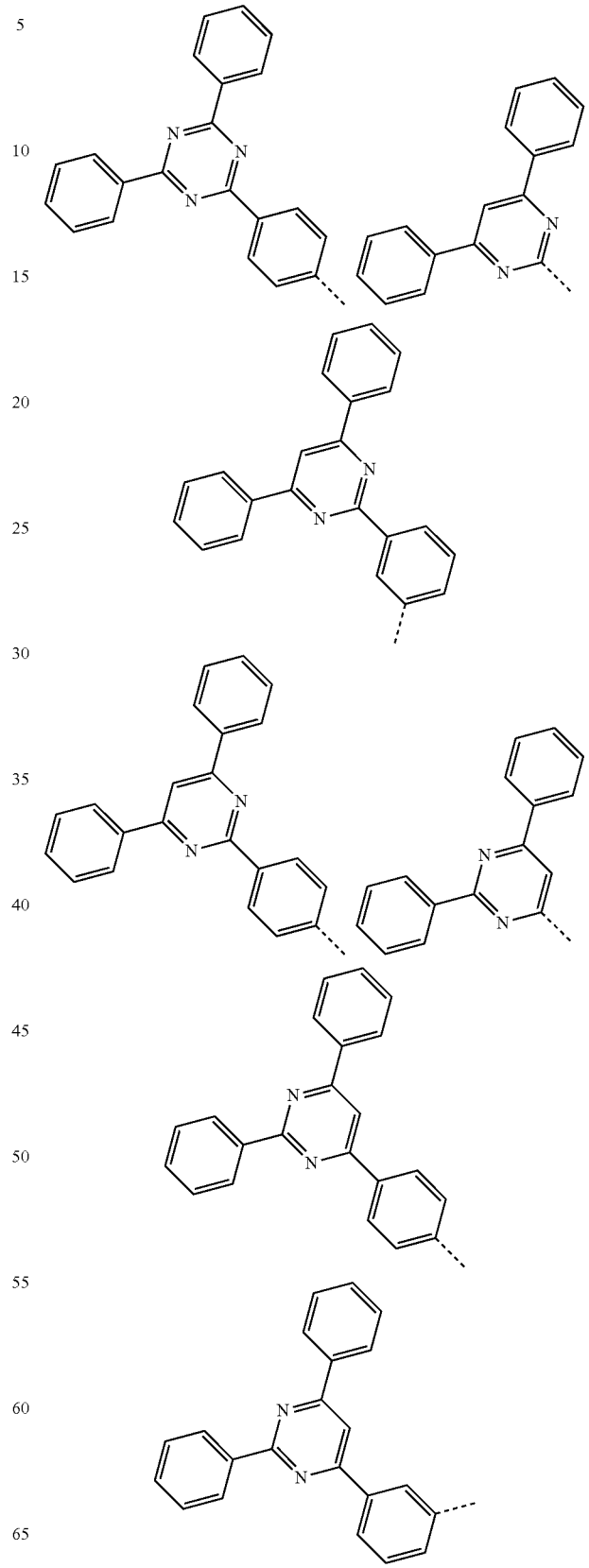
[A-3]

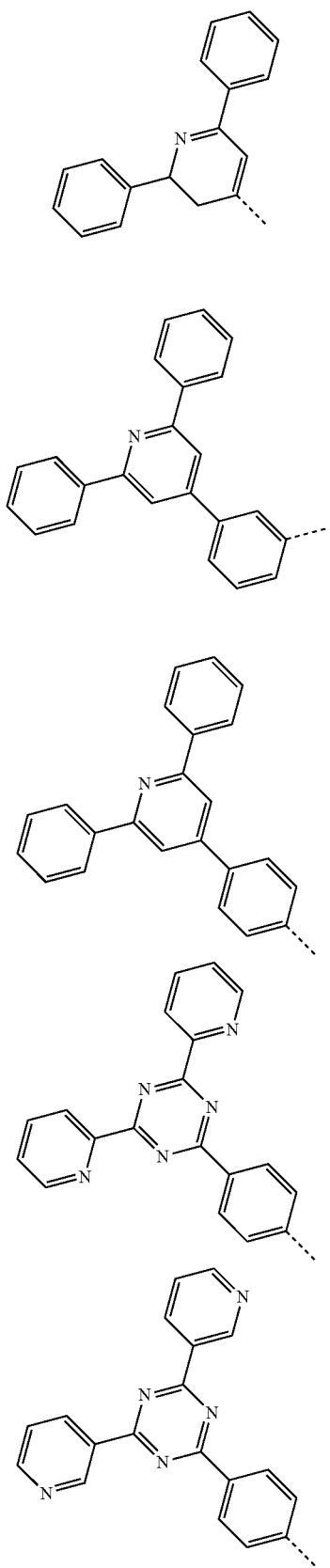

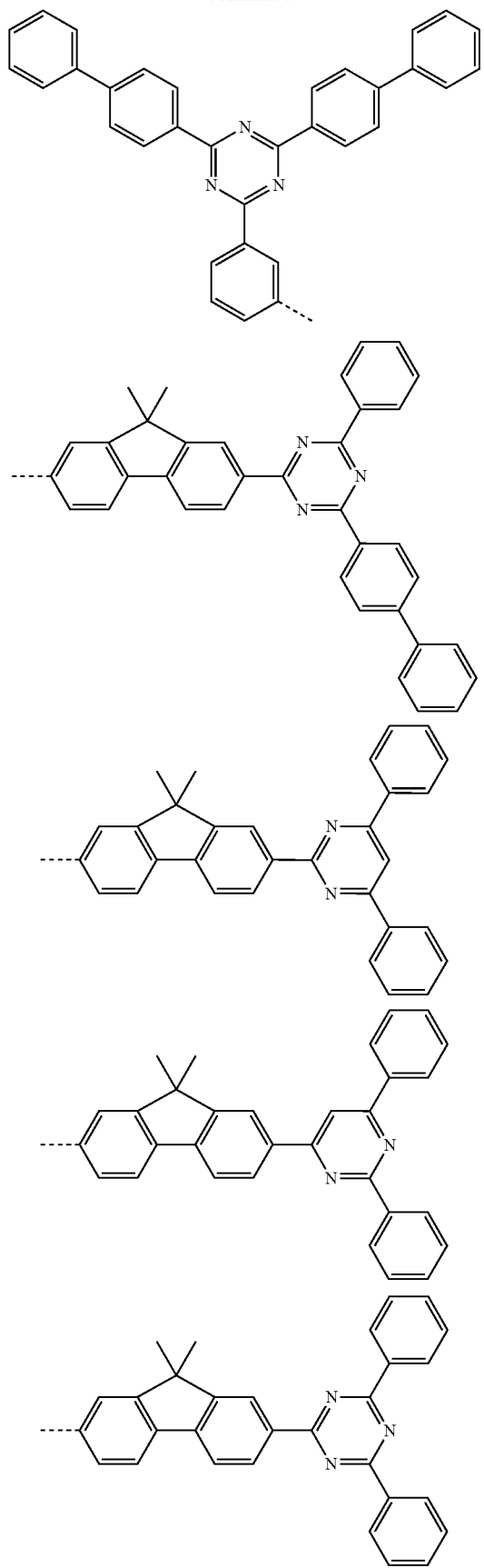
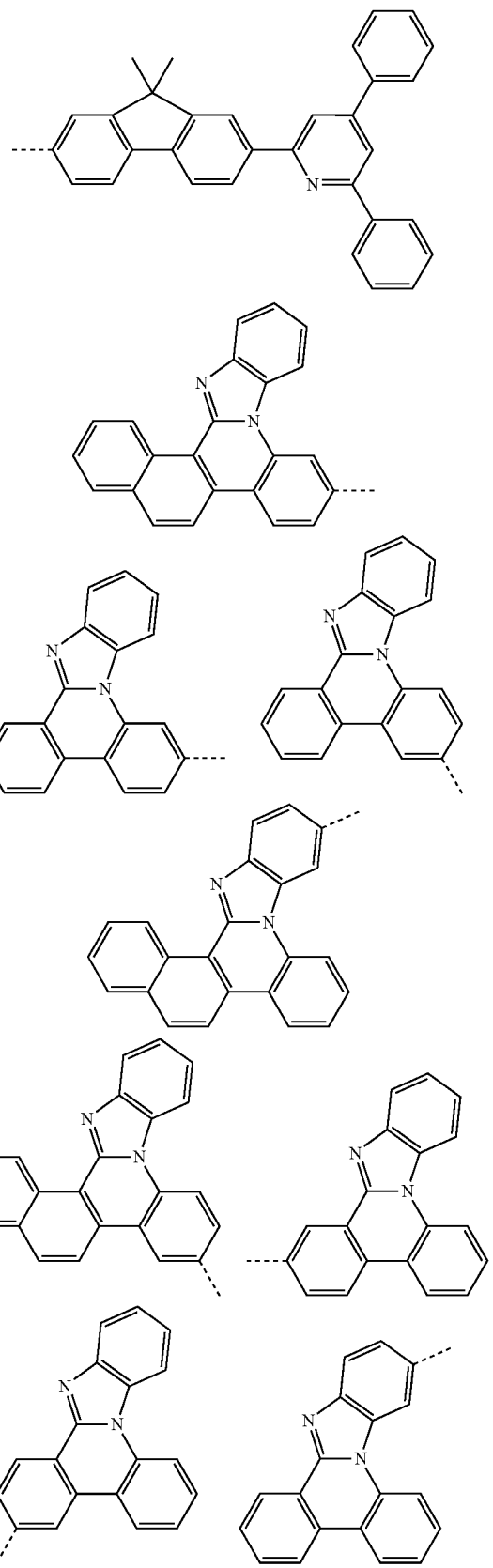

35
-continued
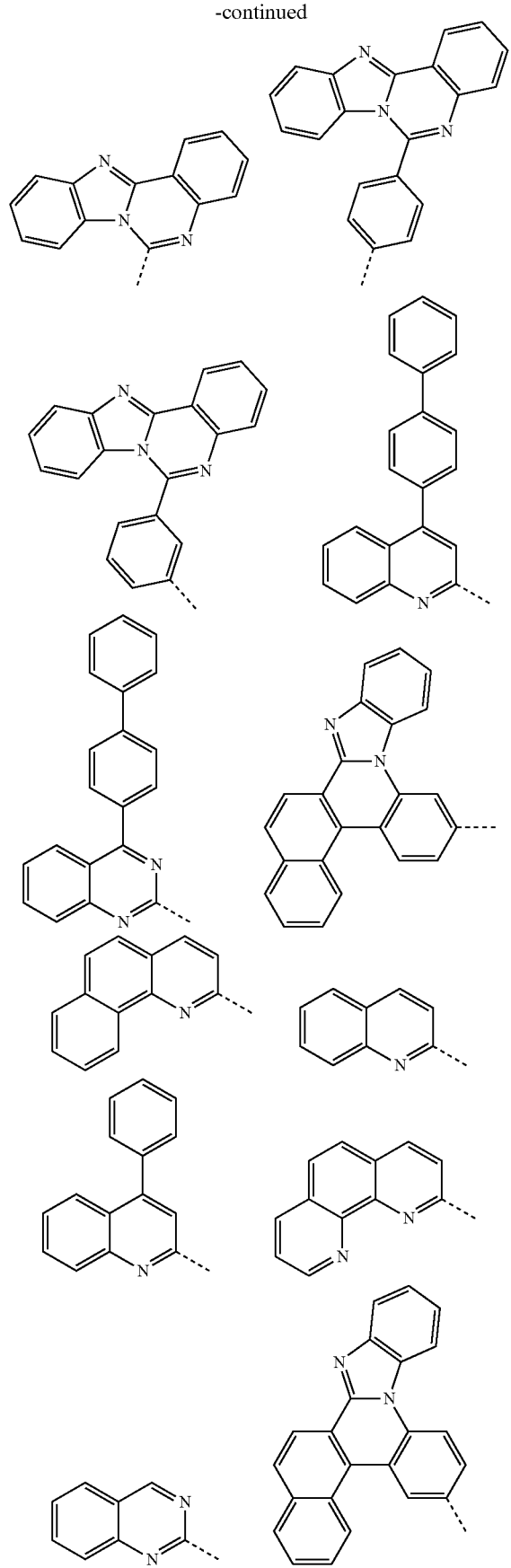
36
-continued
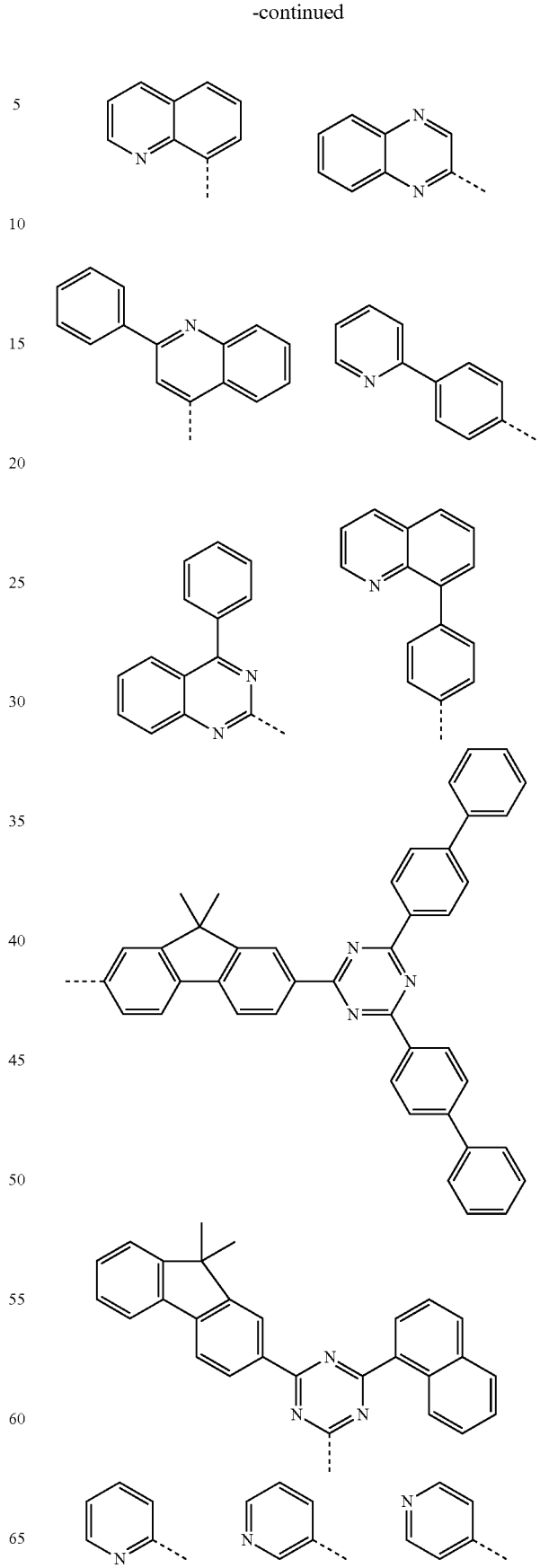

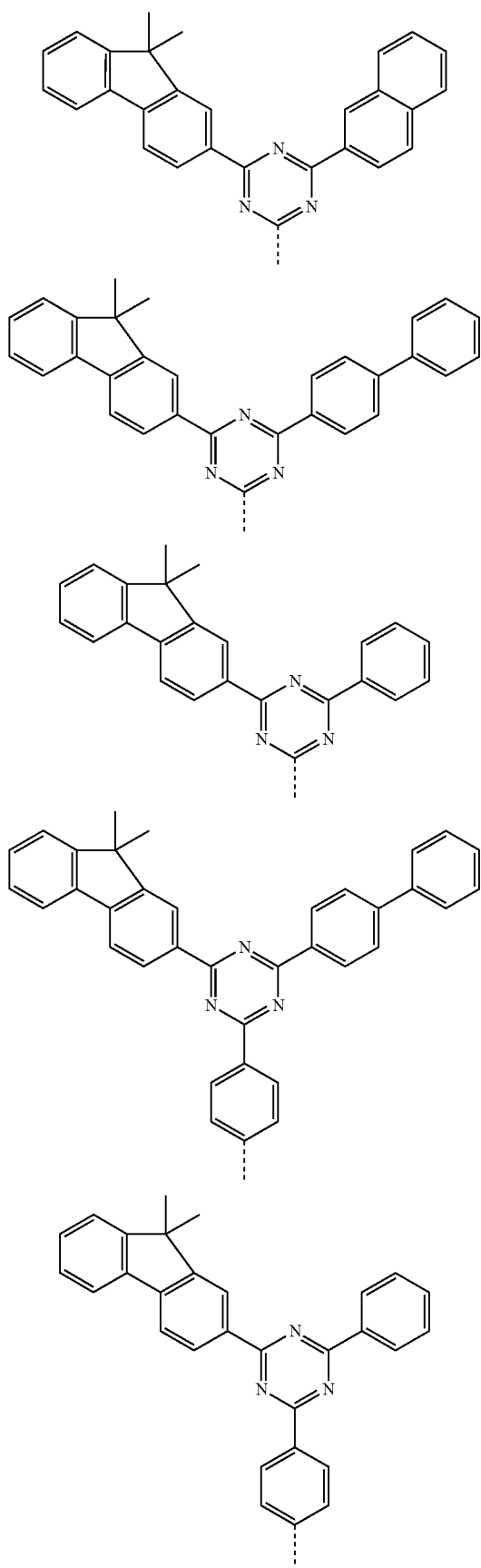
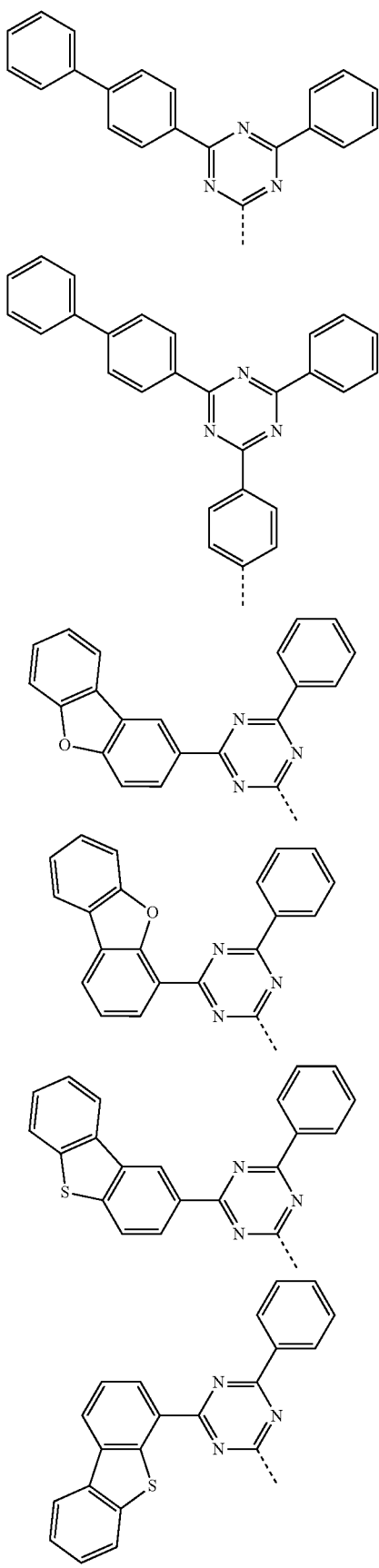

[A-4]
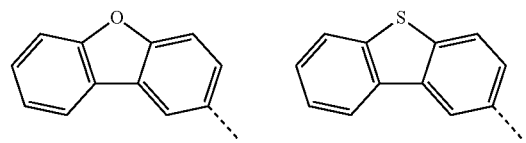
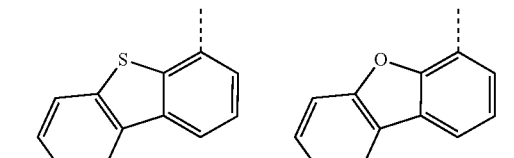
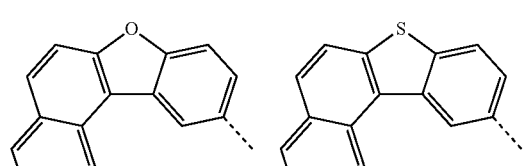
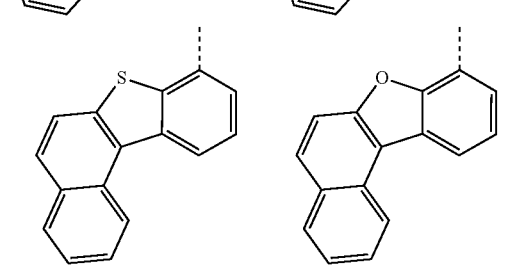
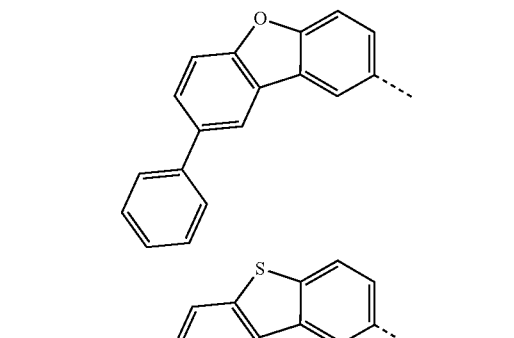
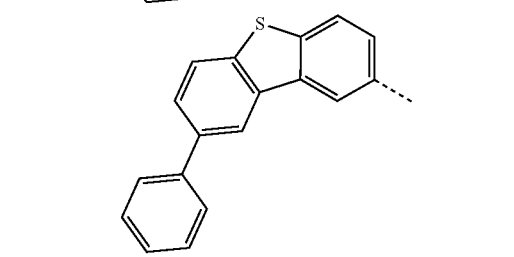
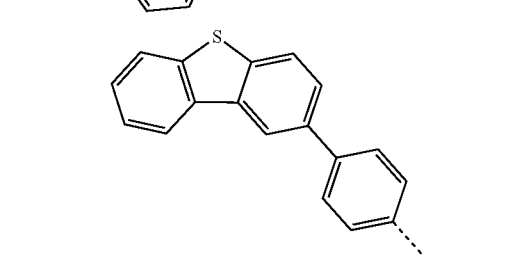
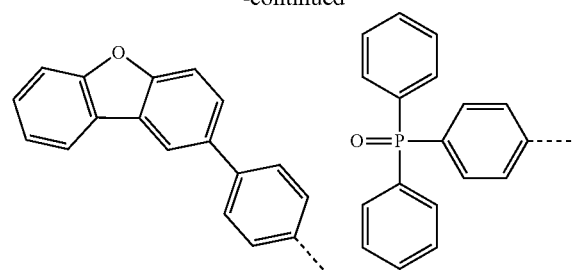
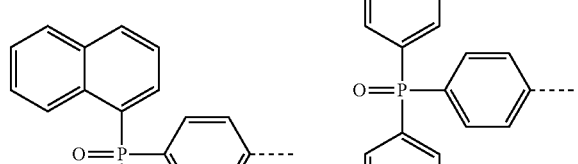
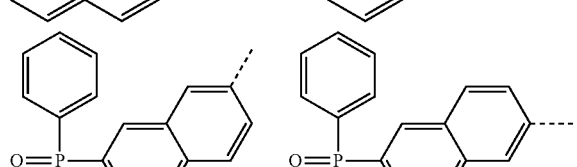
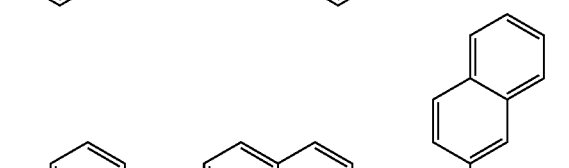
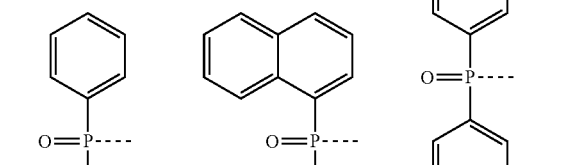
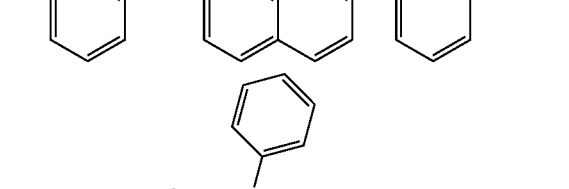
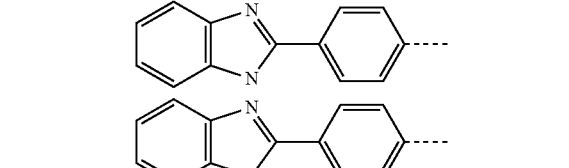
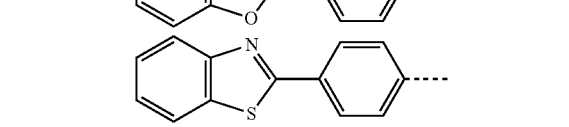

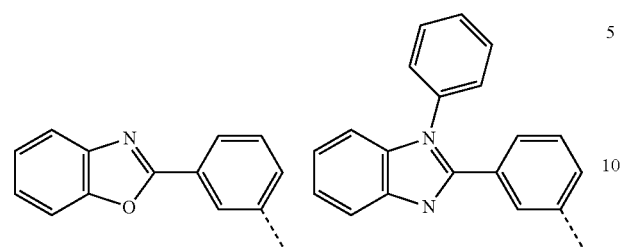
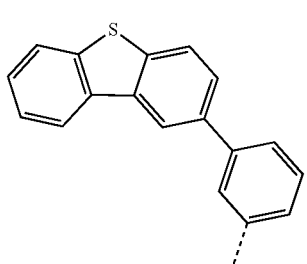
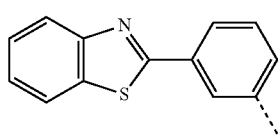
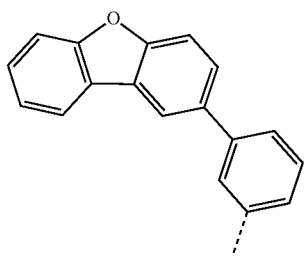
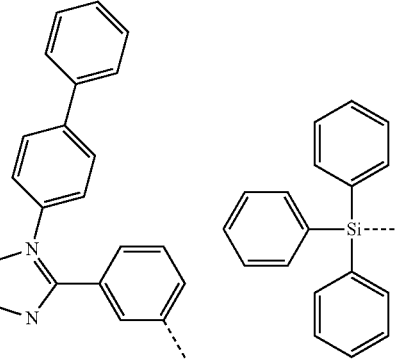
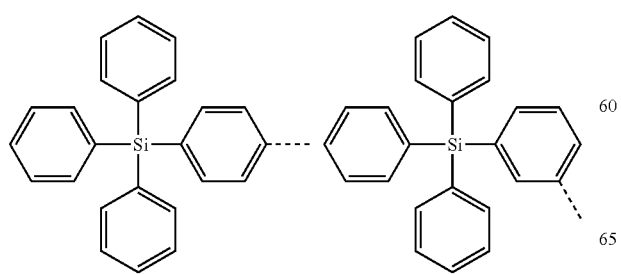
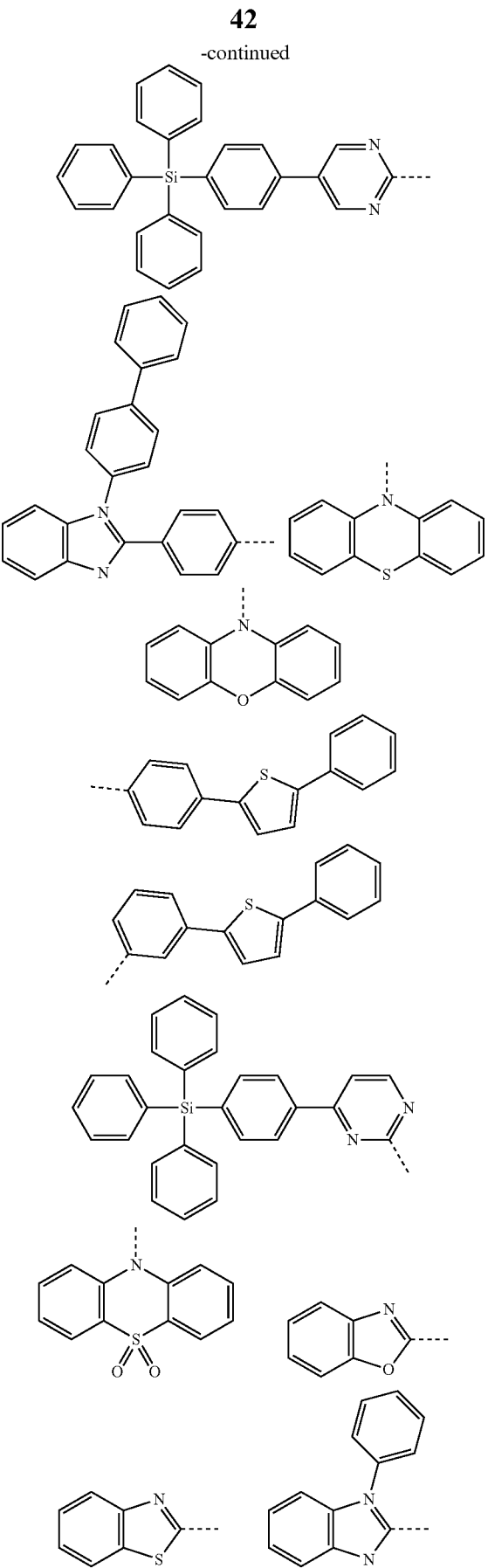

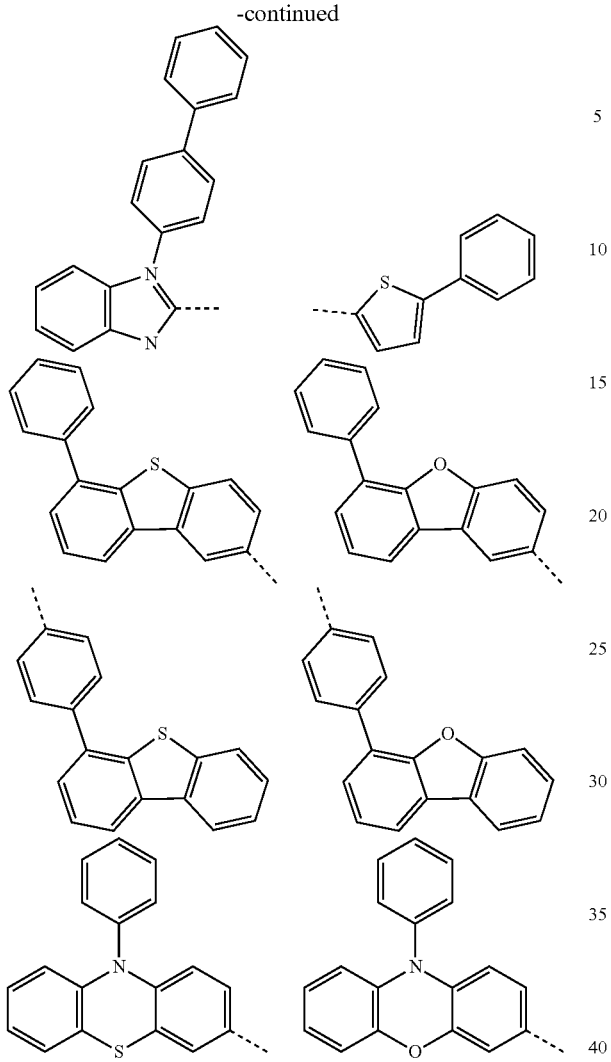

In the structural formulae, ---- means a moiety bonded to Chemical Formula 1 via L1.

According to an exemplary embodiment of the present specification, in Chemical Formula 1, Ar1 is a phosphine oxide group which is substituted with an aryl group; an aryl group which is unsubstituted or substituted with an alkyl group or an aryl group; or a heteroaryl group which is unsubstituted or substituted with an aryl group, which is unsubstituted or substituted with an alkyl group, or a heteroaryl group.

According to an exemplary embodiment of the present specification, in Chemical Formula 1, Ar1 is a phosphine oxide group which is substituted with an aryl group; a phenyl group; a naphthyl group; a fluorenyl group which is substituted with an alkyl group; a pyridyl group which is unsubstituted or substituted with an aryl group; a pyrimidyl group which is unsubstituted or substituted with an aryl group; a triazinyl group which is unsubstituted or substituted with an aryl group, which is unsubstituted or substituted with an alkyl group, or a heteroaryl group; a dibenzofuranyl group; a dibenzothiophene group; a quinazolyl group which is unsubstituted or substituted with an aryl group; a benzocarbazolyl group; a carbazolyl group which is unsubstituted or substituted with an aryl group; a triphenylenyl group; a phenanthrenyl group; or a benzimidazolyl group which is unsubstituted or substituted with an aryl group.

According to an exemplary embodiment of the present specification, in Chemical Formula 1, Ar1 is a phosphine oxide group which is substituted with a phenyl group; a phenyl group; a naphthyl group; a fluorenyl group which is substituted with a methyl group; a pyridyl group which is unsubstituted or substituted with a phenyl group; a pyrimidyl group which is unsubstituted or substituted with one or more selected from the group consisting of a phenyl group and a biphenyl group; a triazinyl group which is unsubstituted or substituted with one or more selected from the group consisting of a phenyl group, a biphenyl group, a fluorenyl group, which is substituted with a methyl group, a dibenzofuranyl group, and a dibenzothiophene group; a dibenzofuranyl group; a dibenzothiophene group; a quinazolyl group which is unsubstituted or substituted with a biphenyl group or a naphthyl group; a benzocarbazolyl group; a carbazolyl group which is unsubstituted or substituted with a phenyl group, a biphenyl group, or a naphthyl group; a triphenylenyl group; a phenanthrenyl group; or a benzimidazolyl group which is unsubstituted or substituted with a phenyl group.

According to an exemplary embodiment of the present specification, Chemical Formula 1 is any one selected from the following compounds.

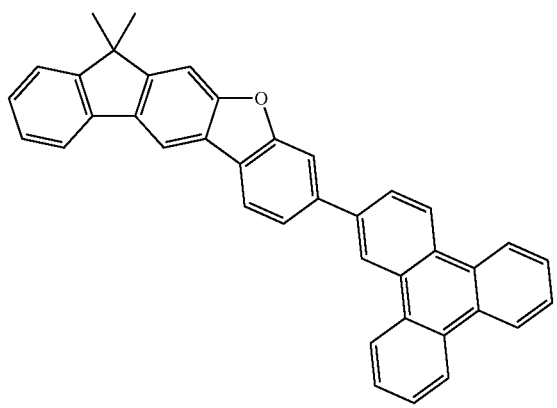

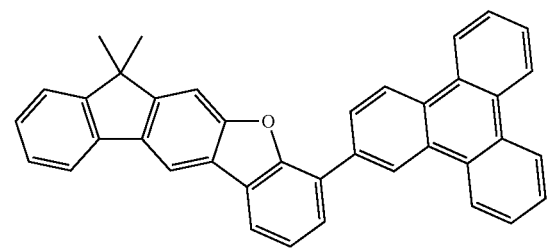

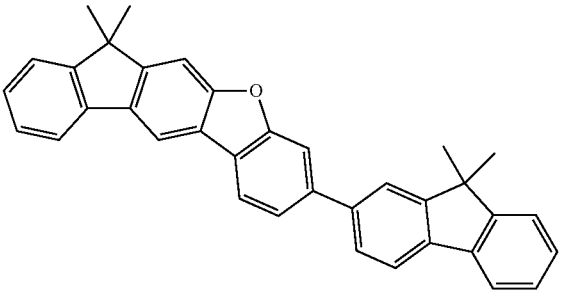

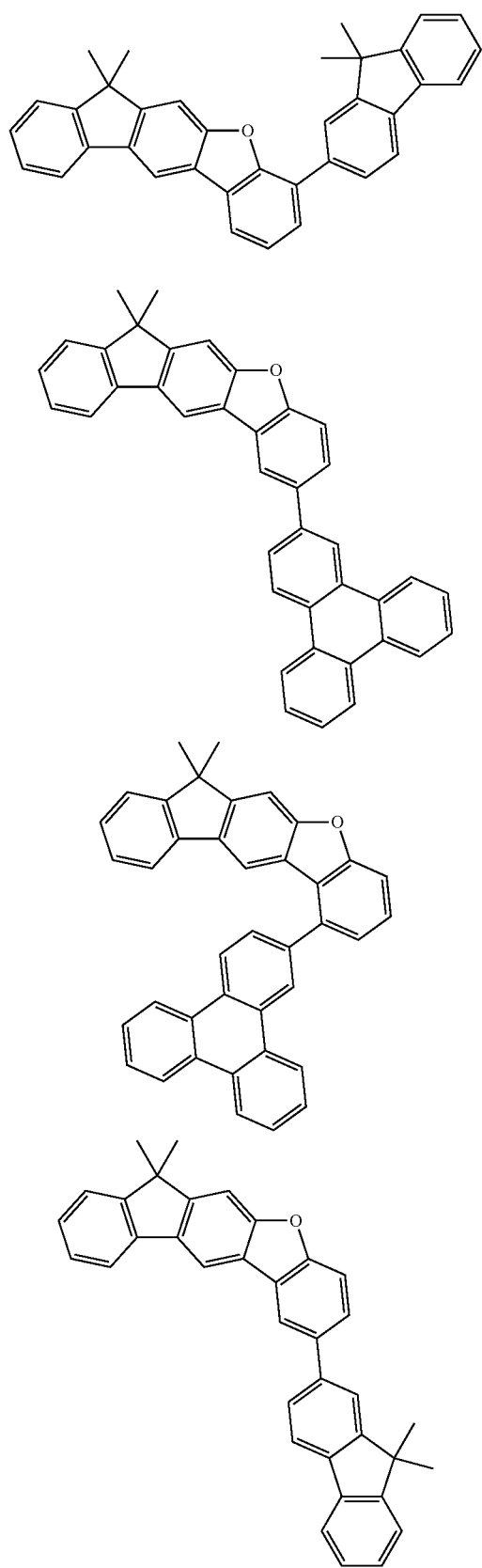
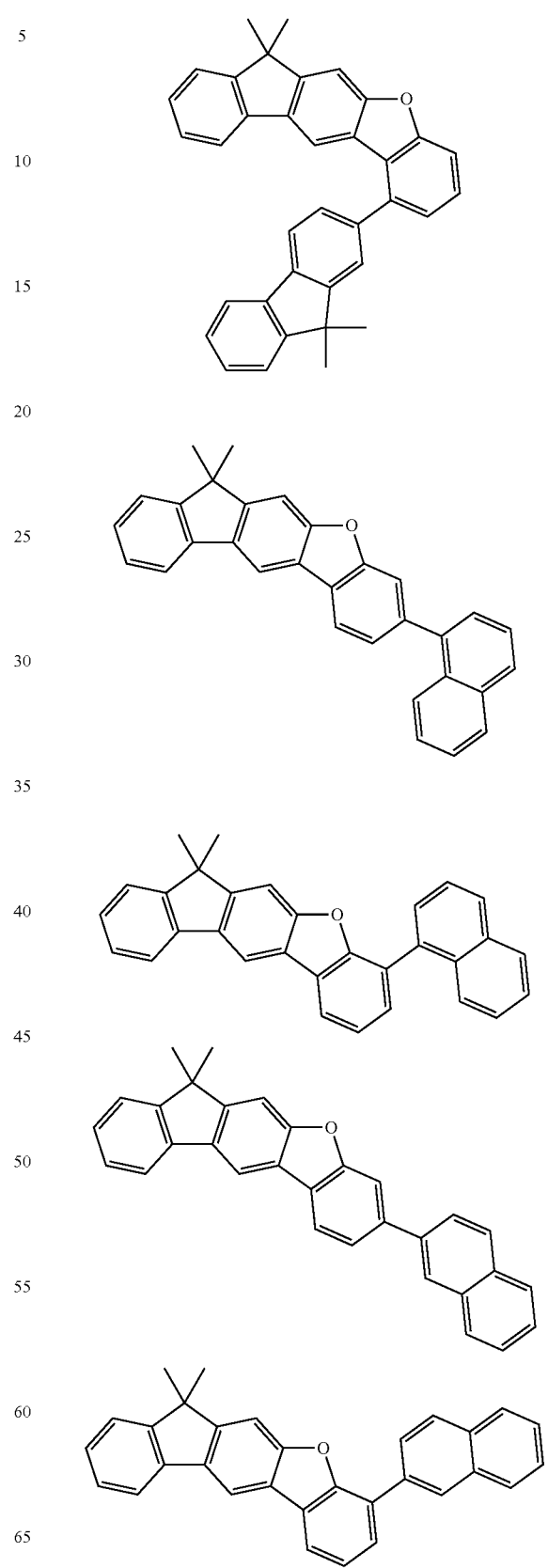

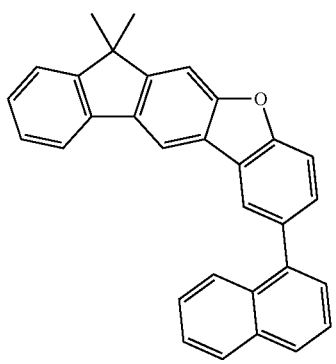
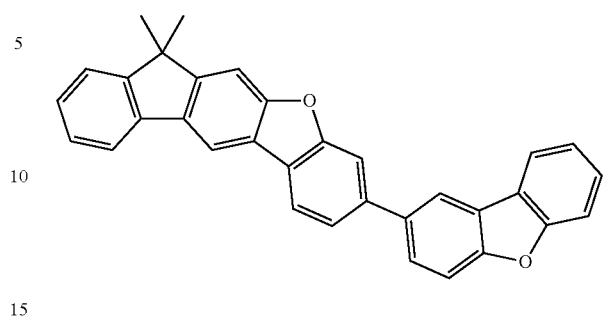
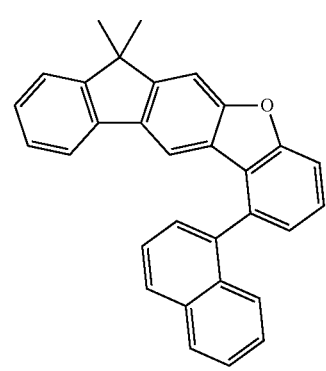
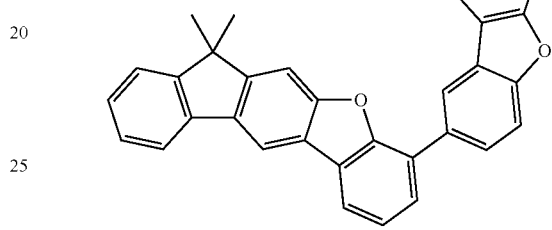
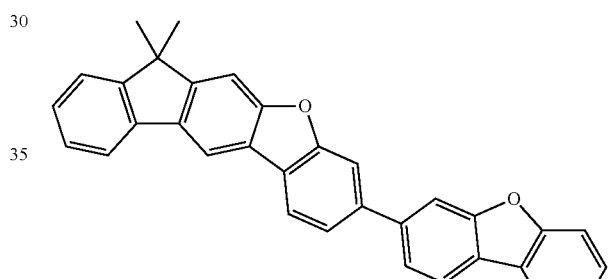
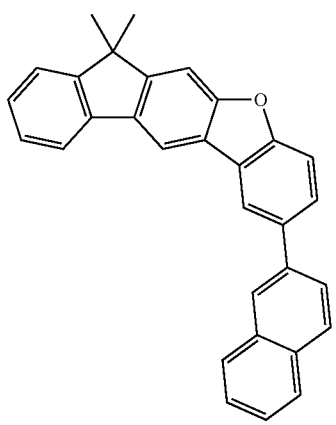
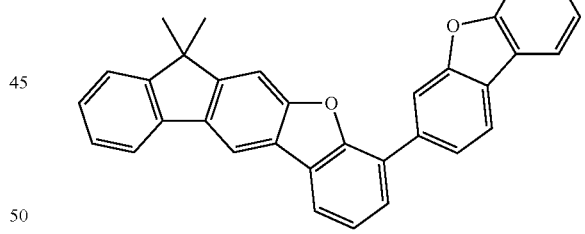
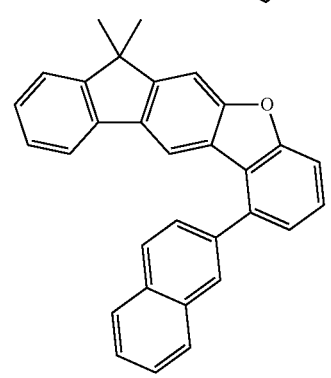
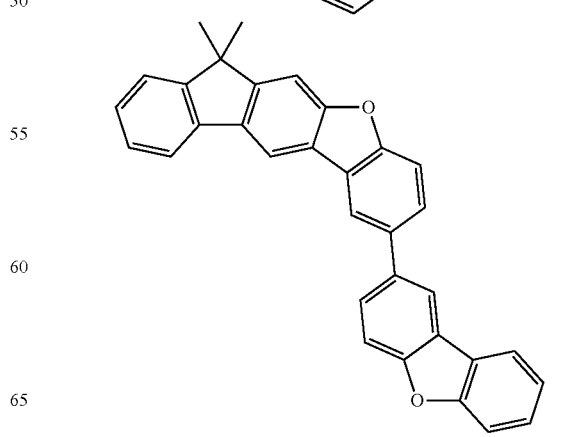

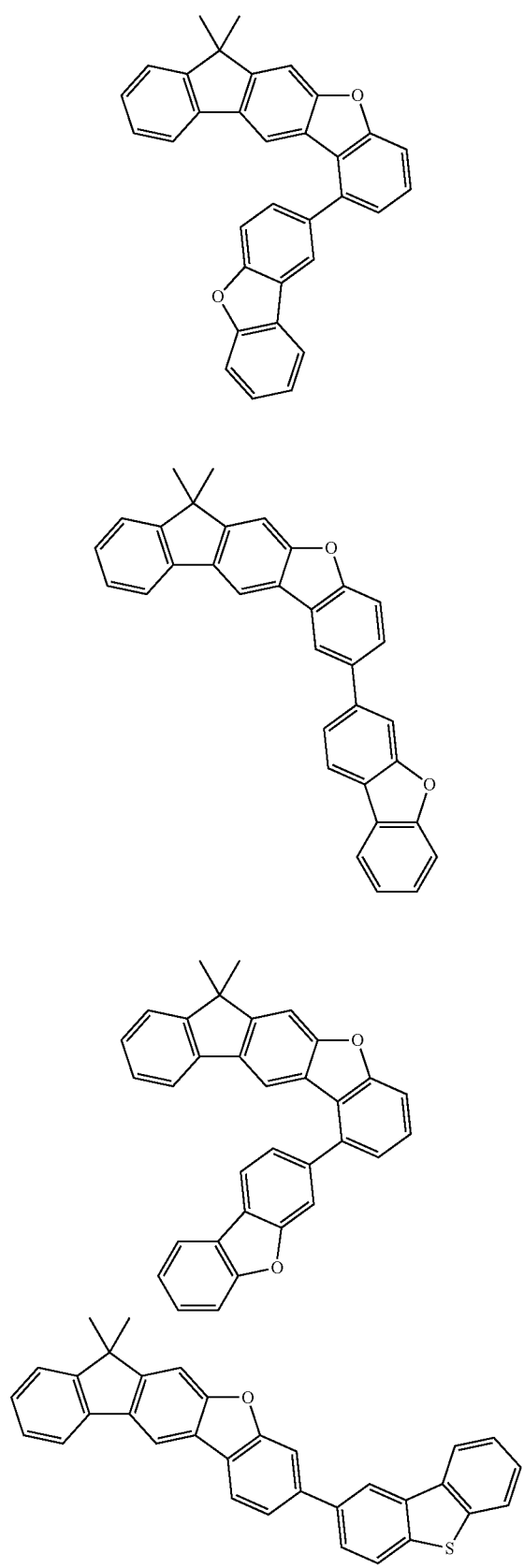
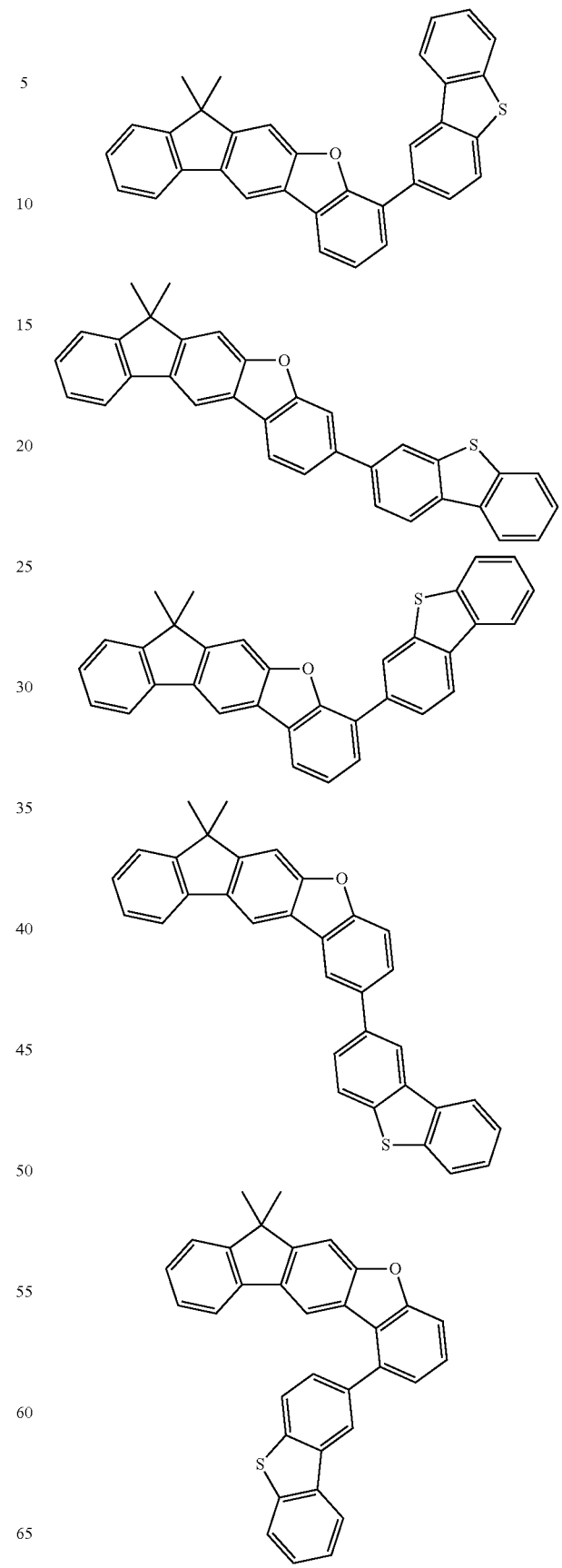

51
-continued
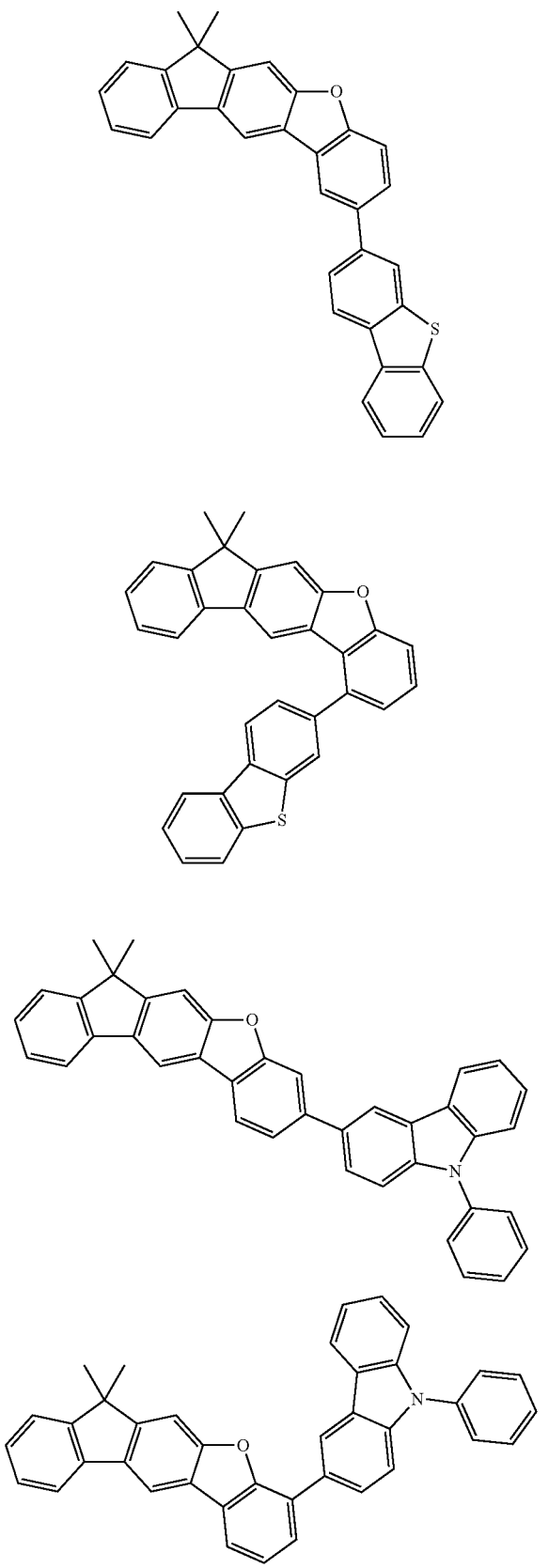
52
-continued
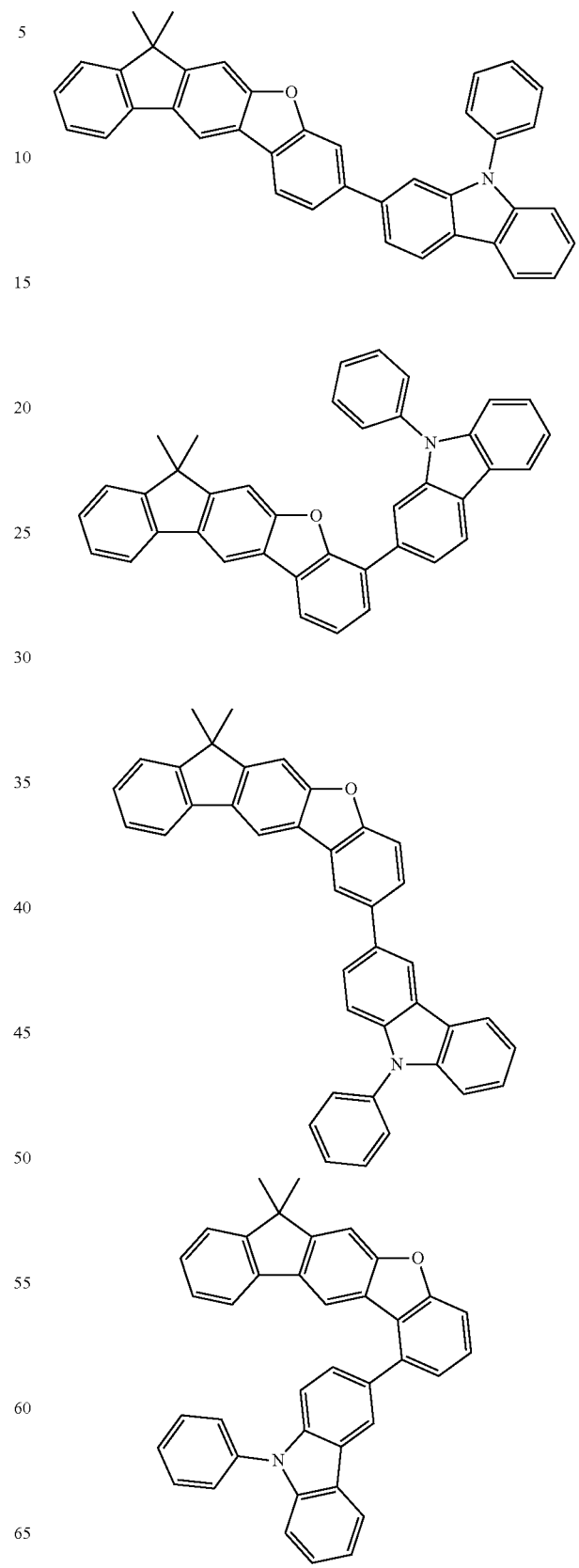

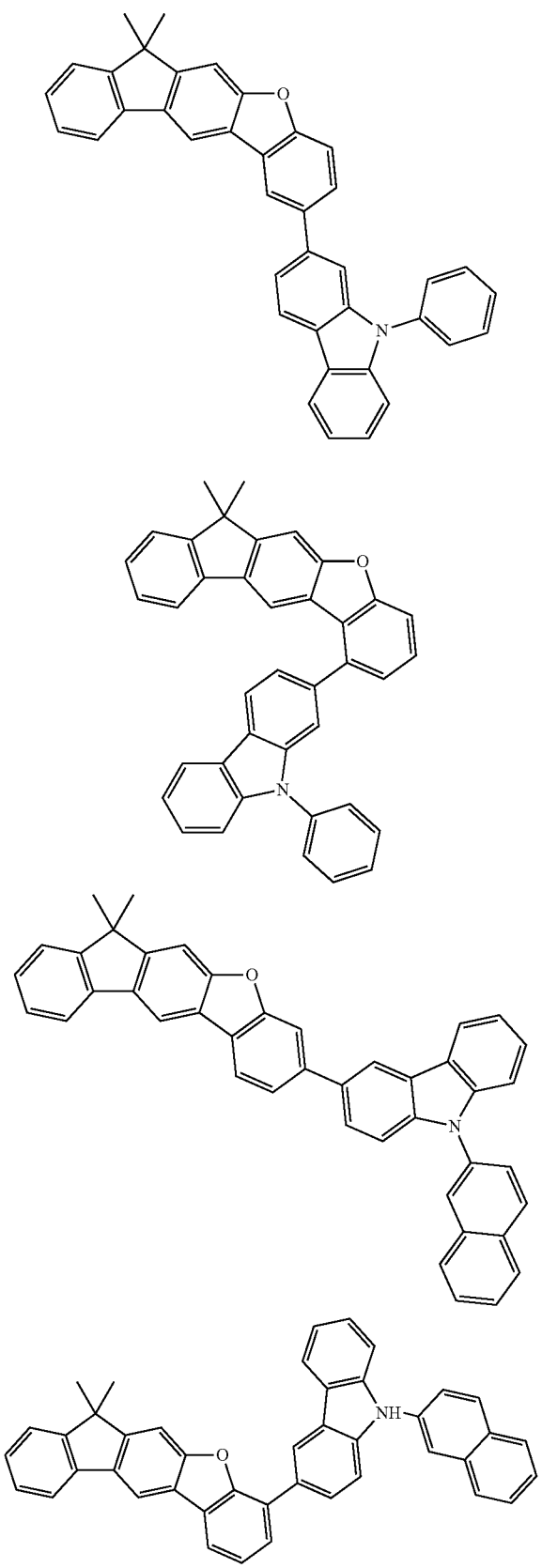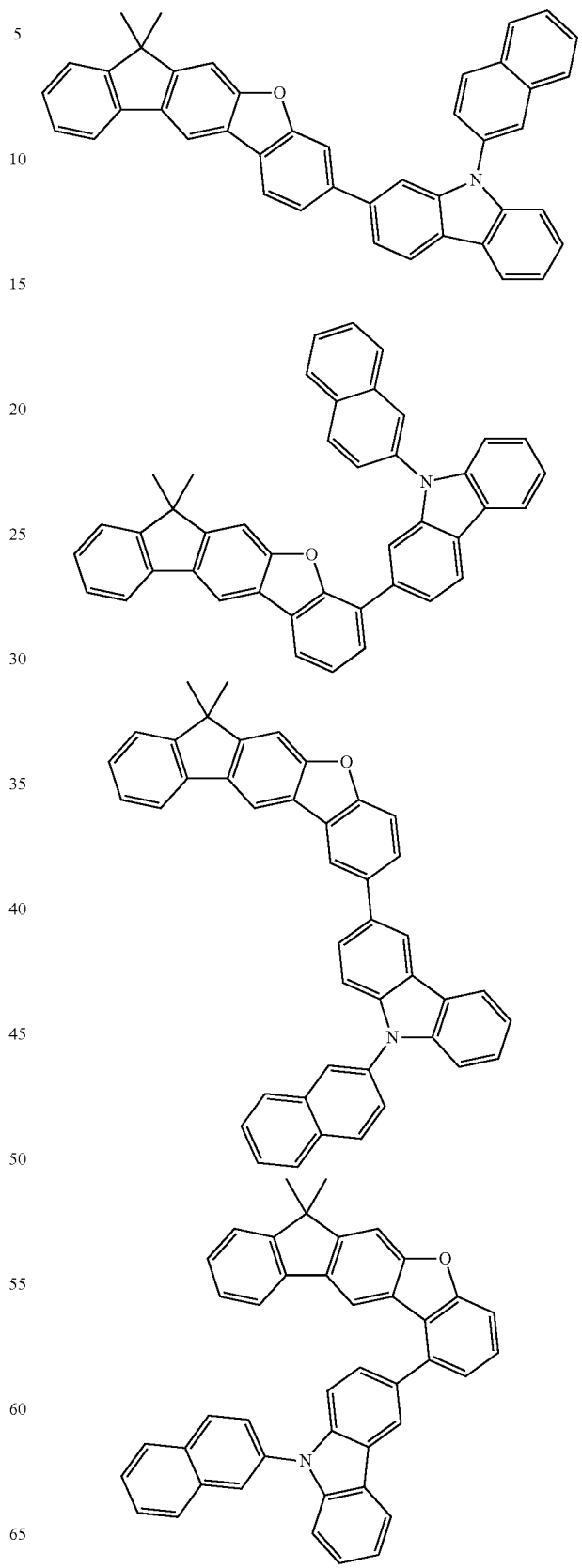

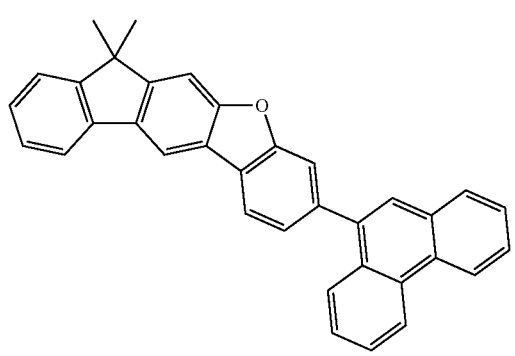
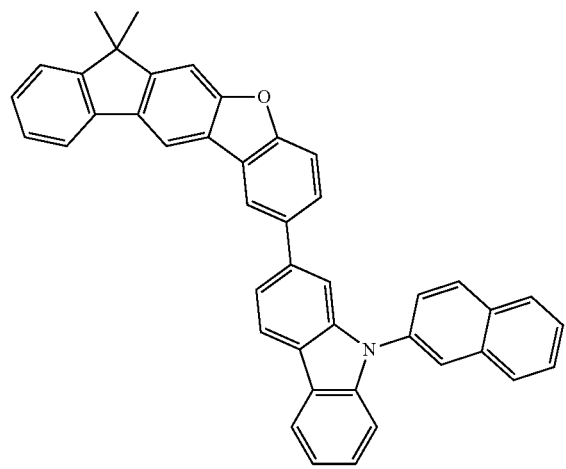
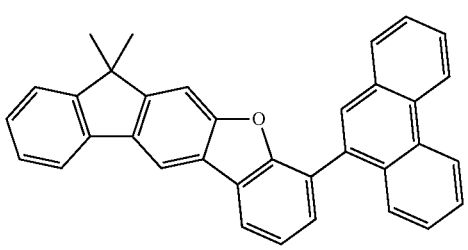
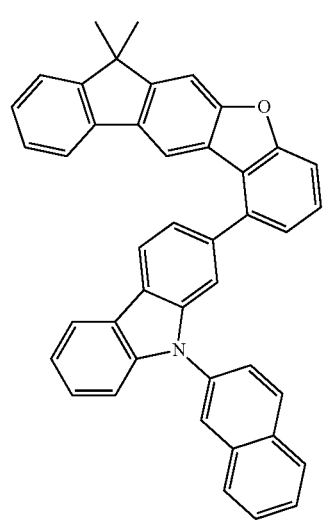
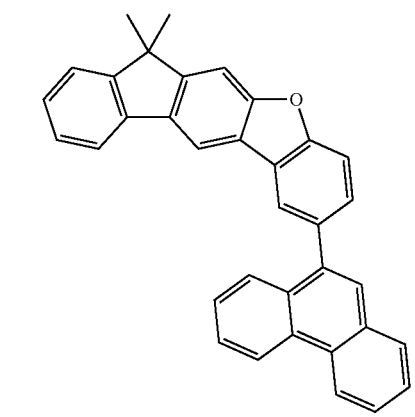
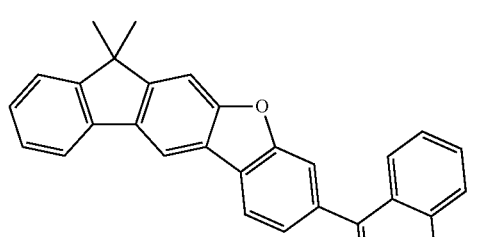
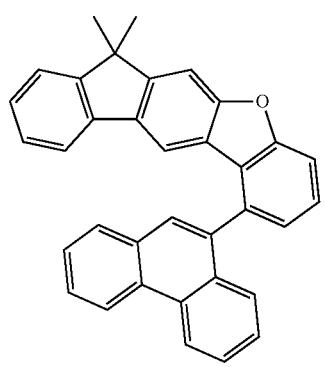
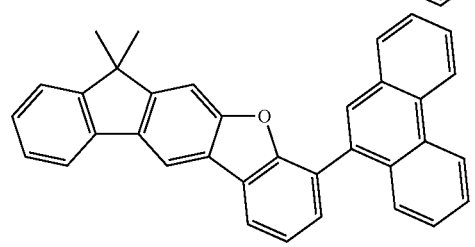

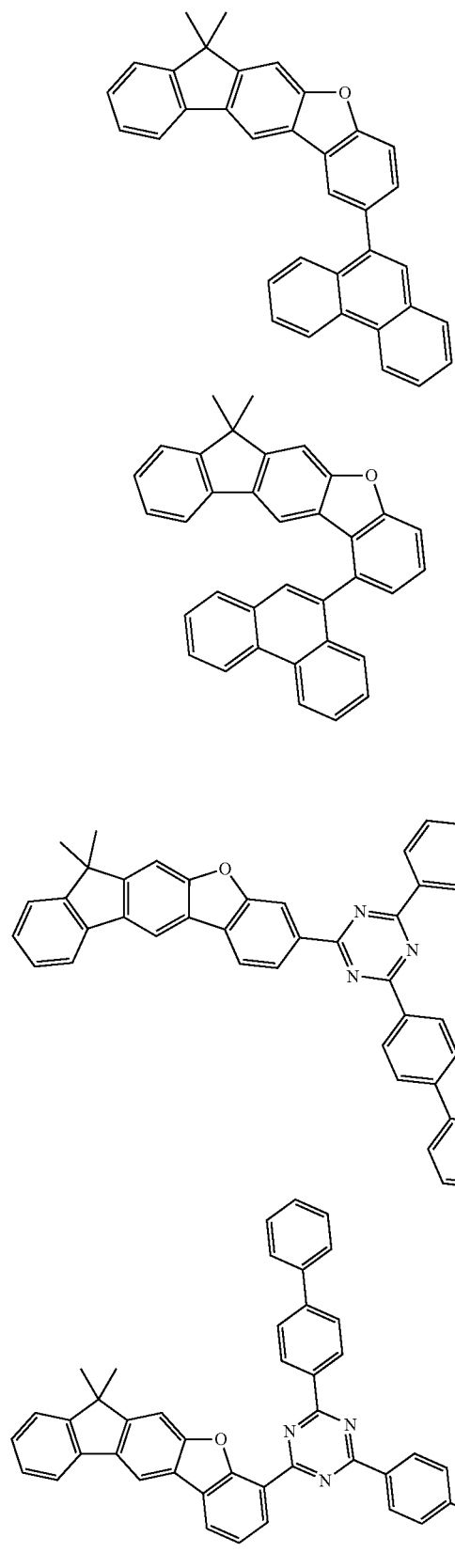
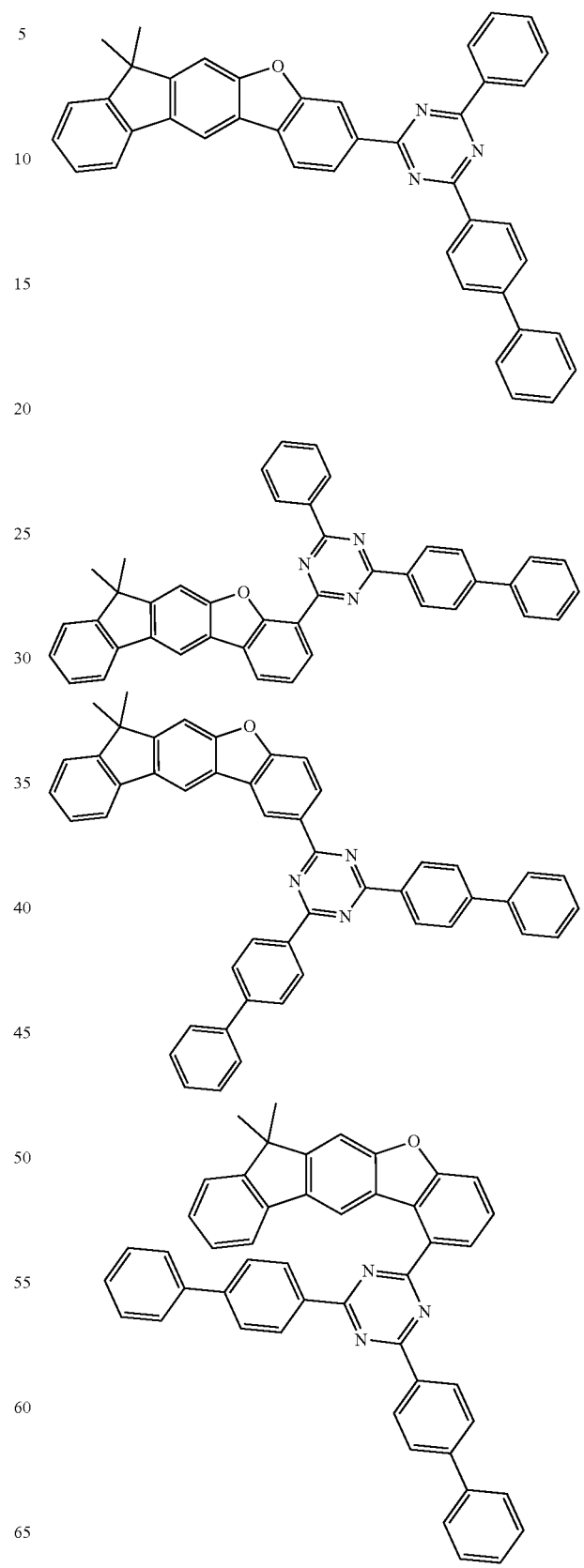

-continued
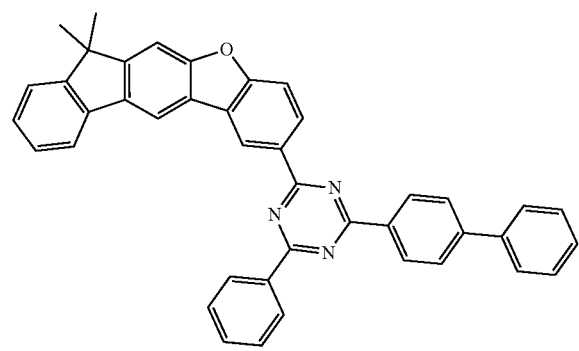
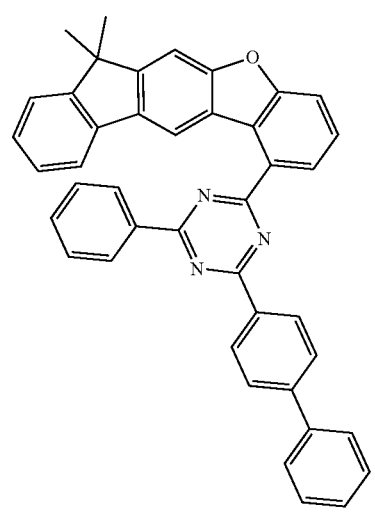
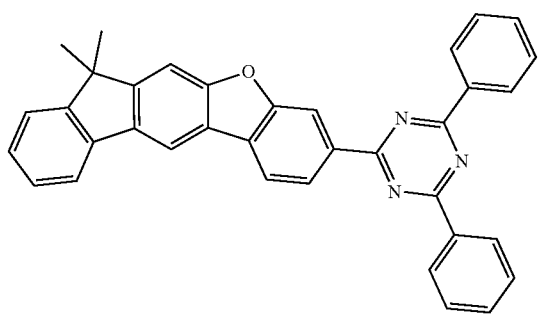
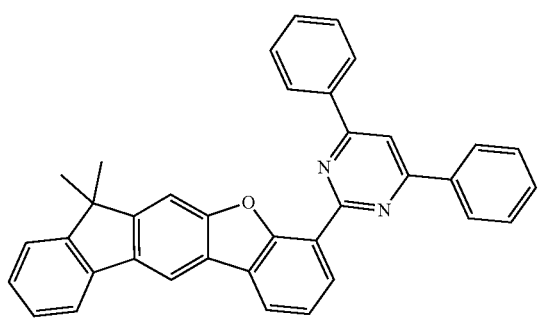
-continued
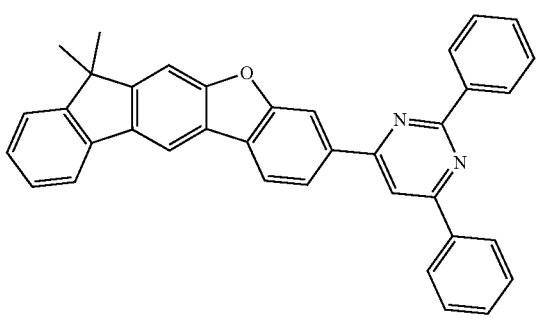
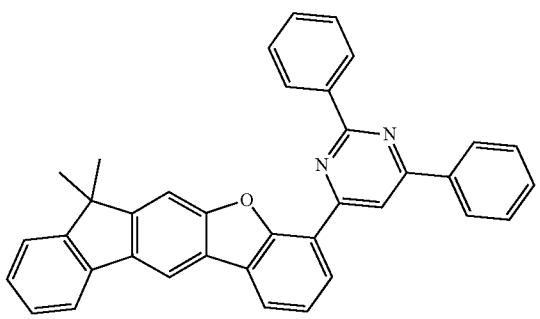
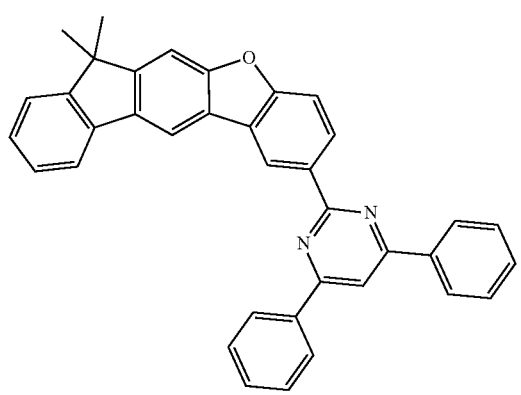
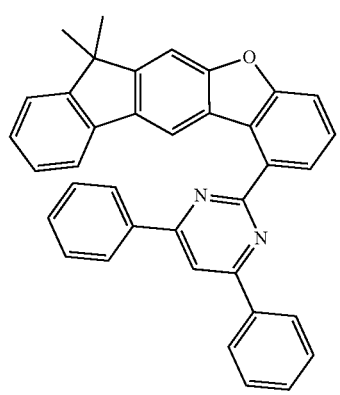

61
-continued
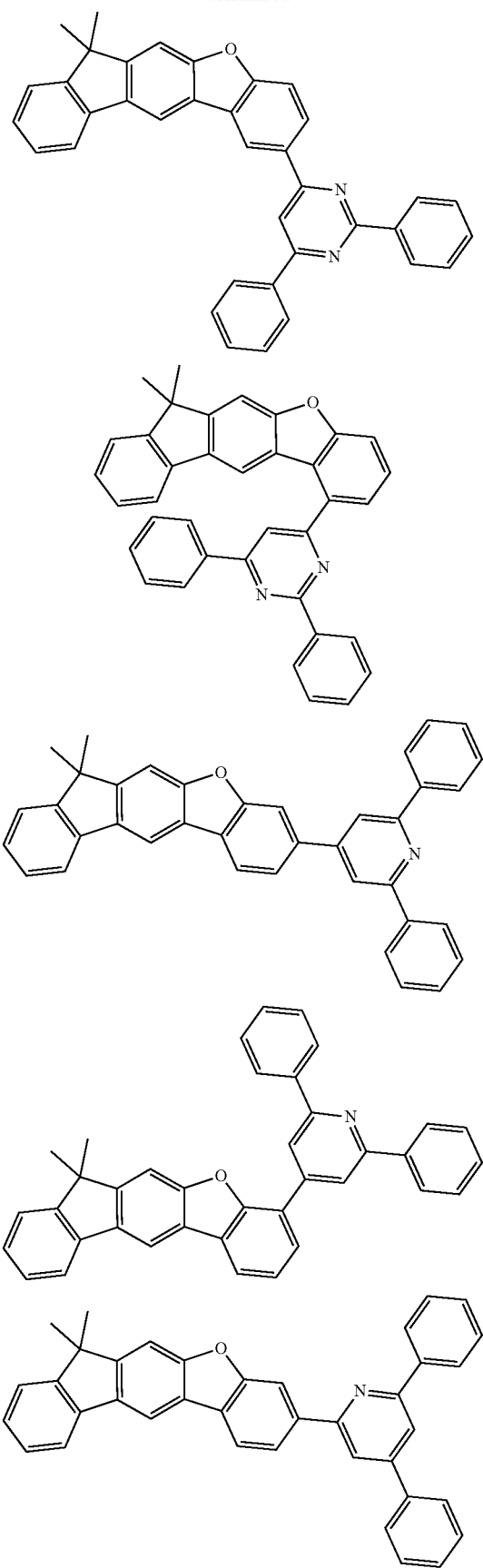
62
-continued
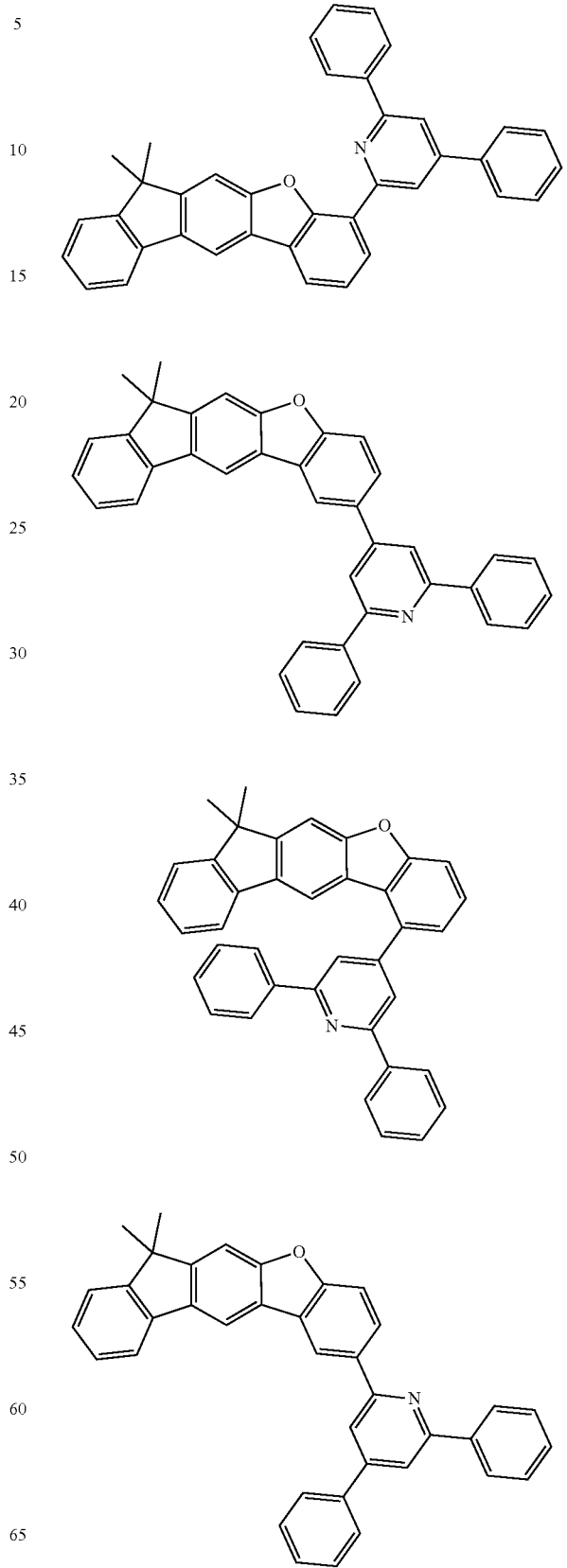

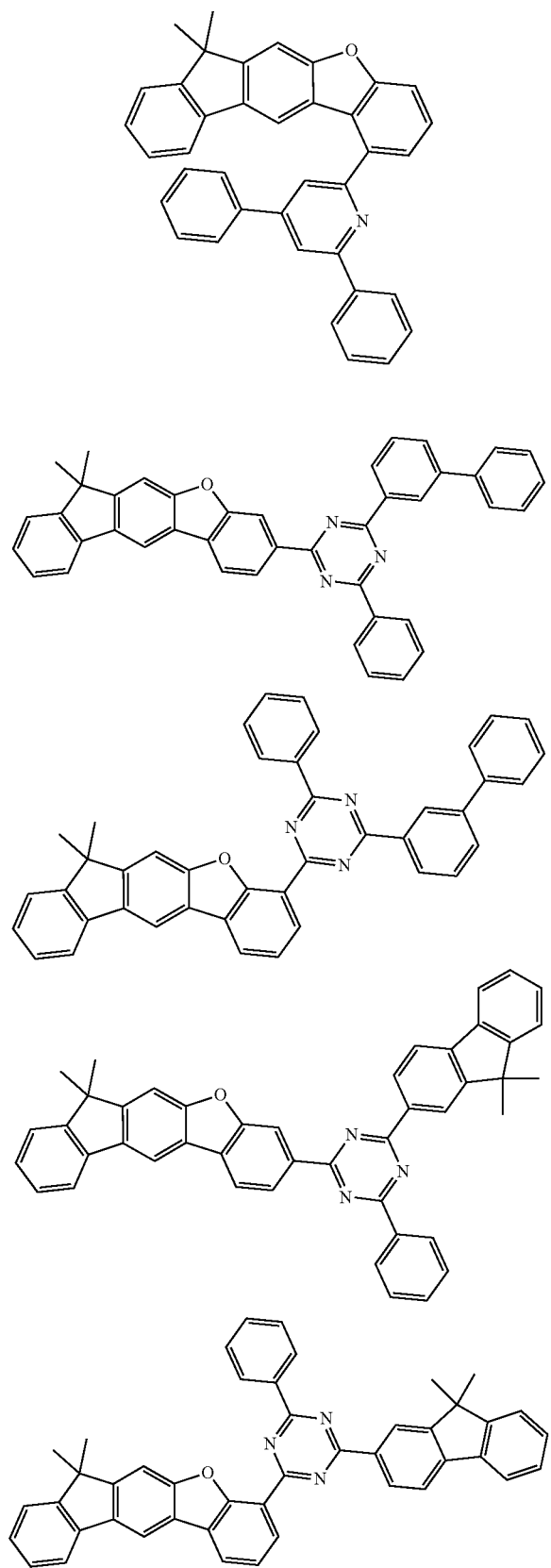
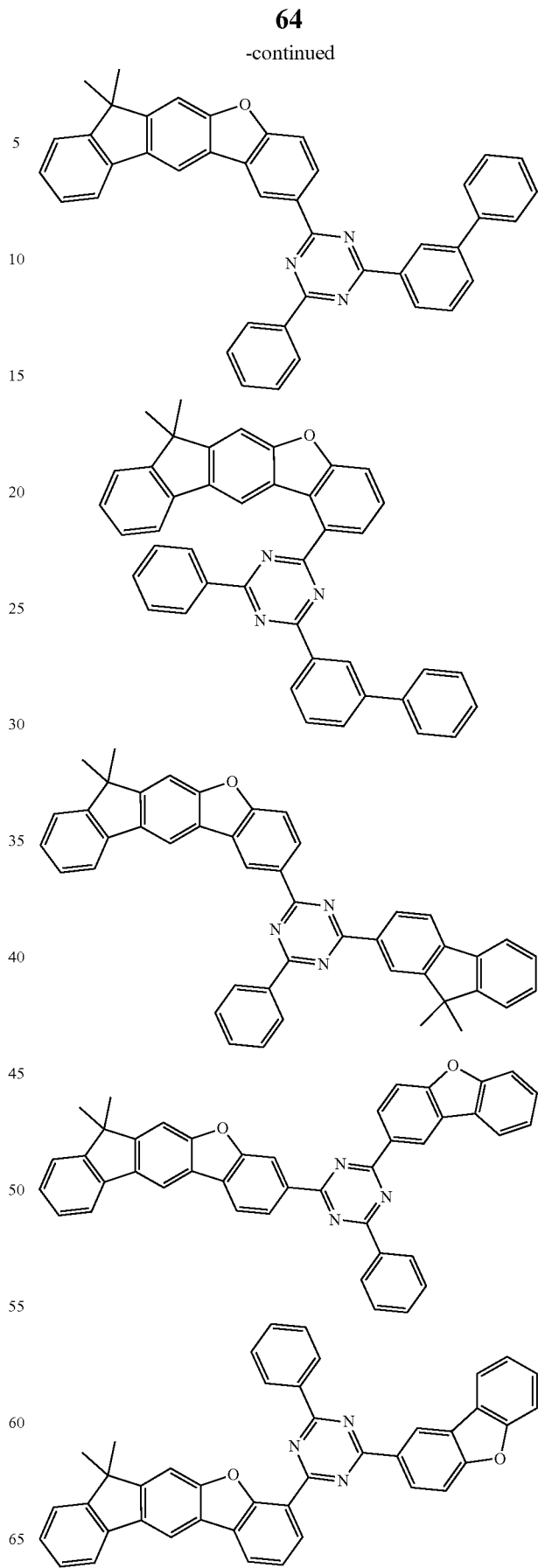

-continued
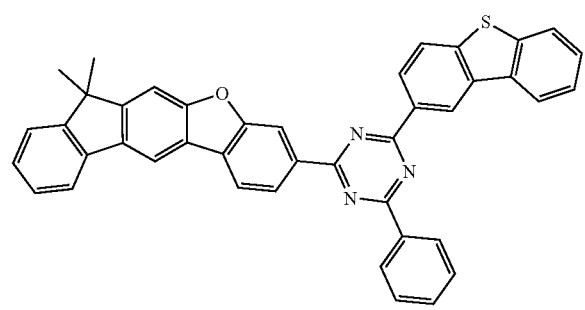
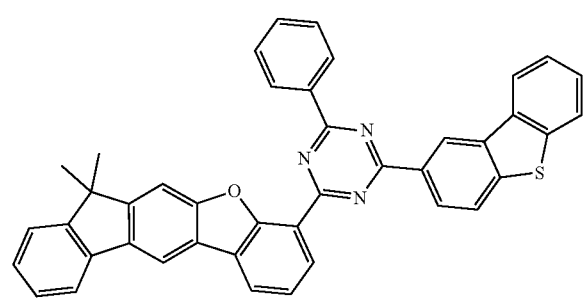
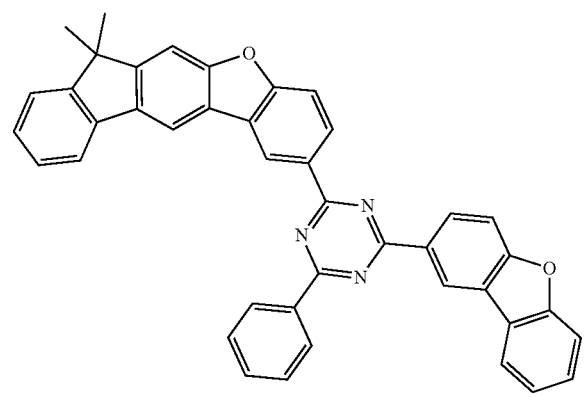
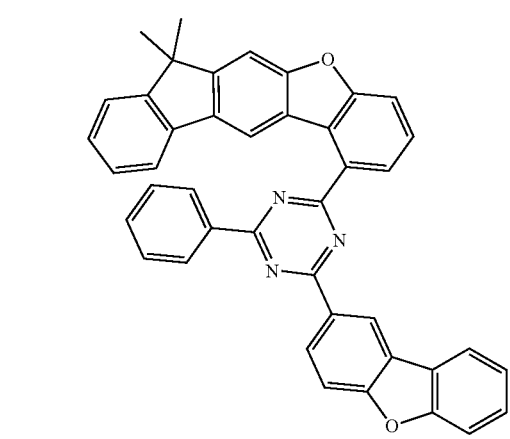
-continued
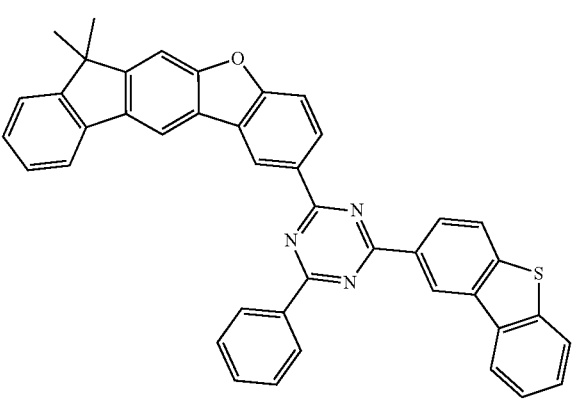
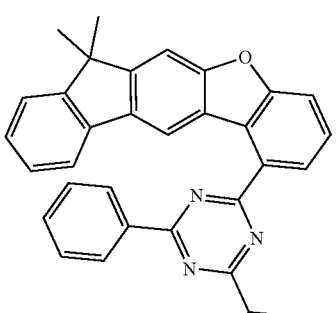
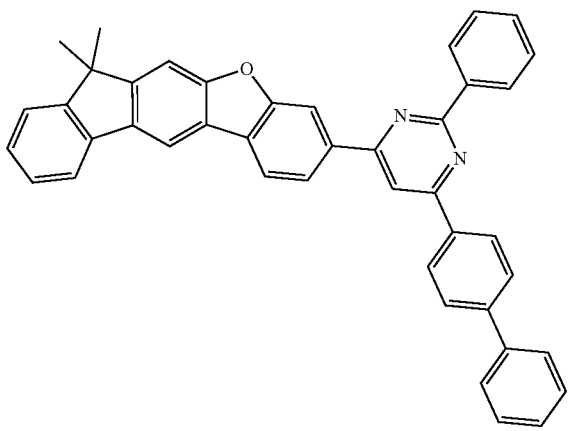
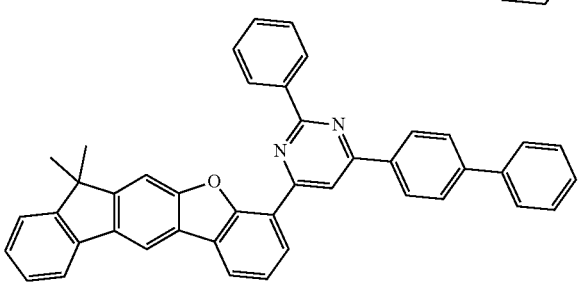

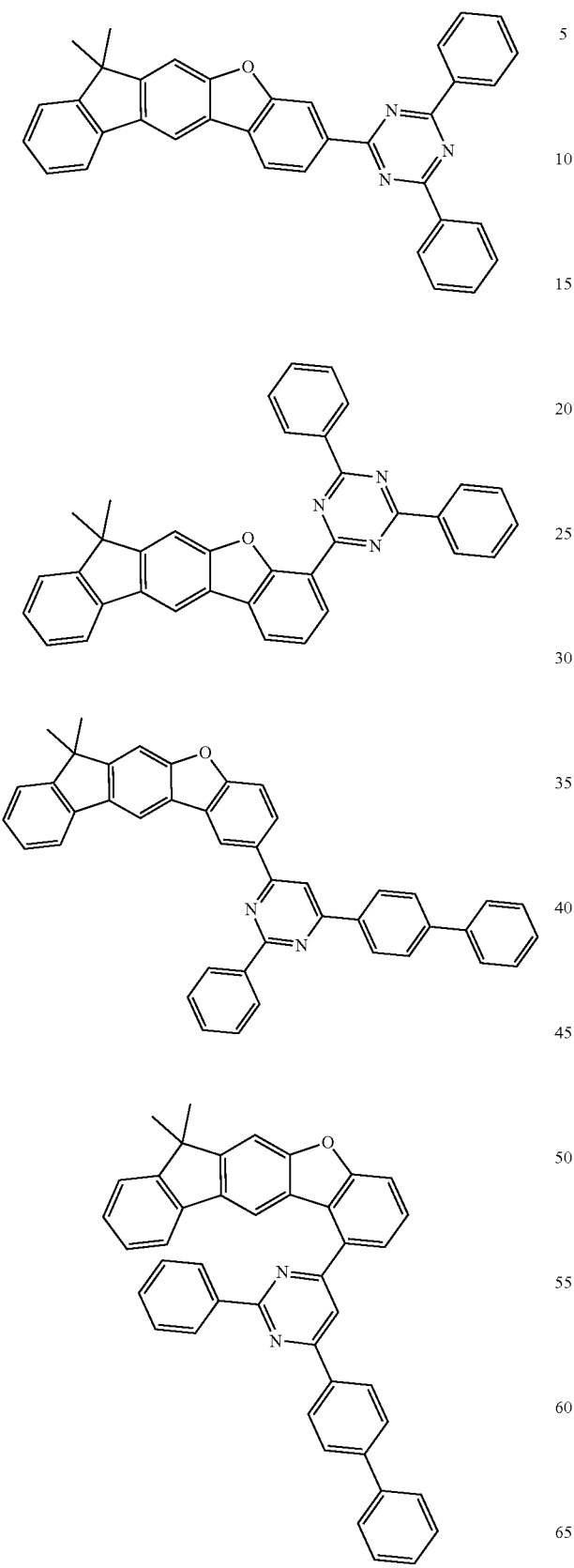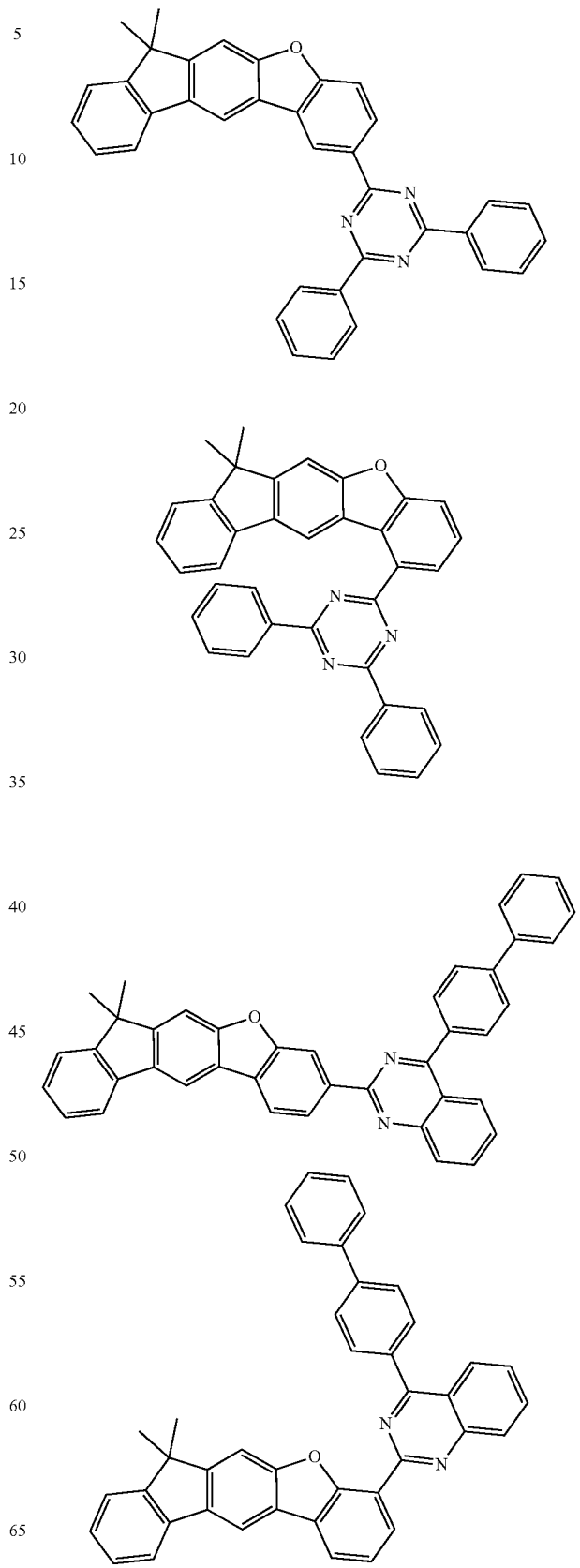

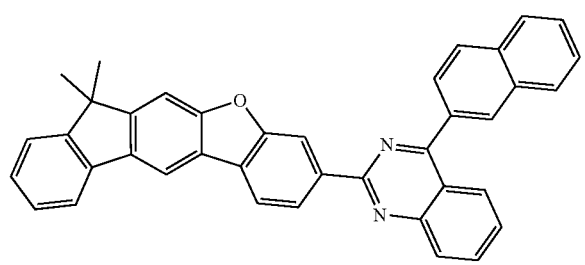
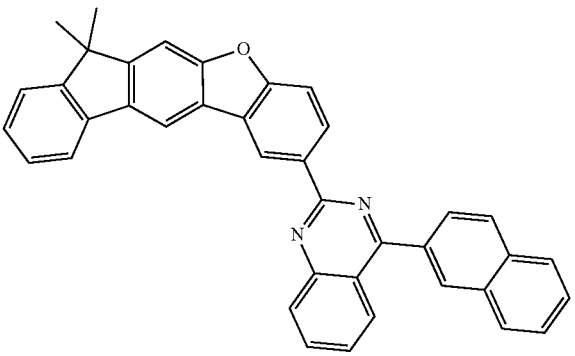
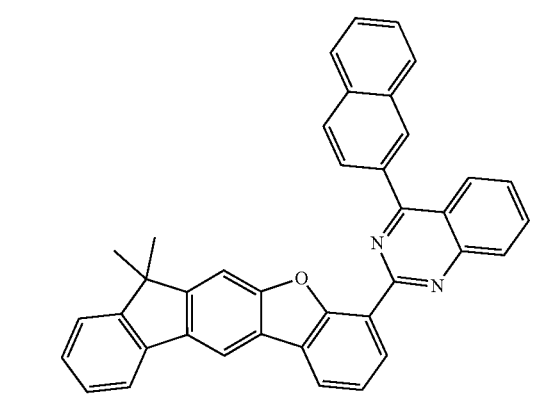
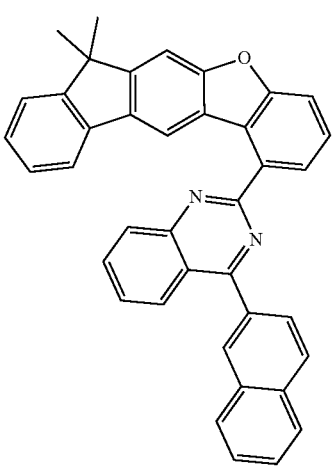
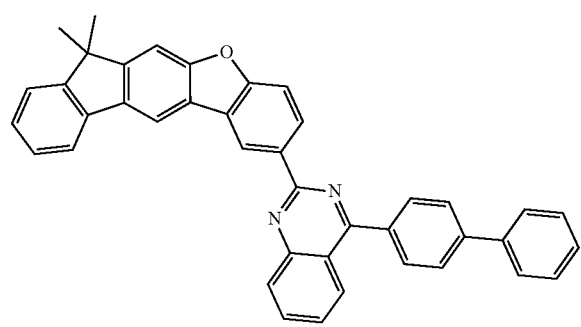
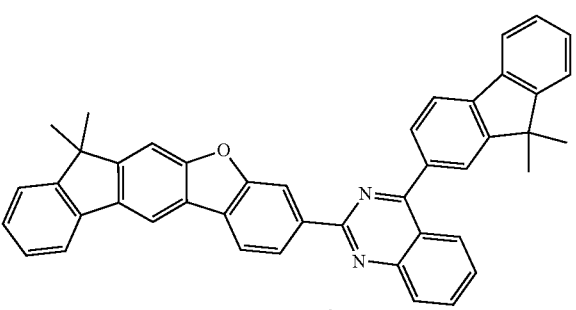
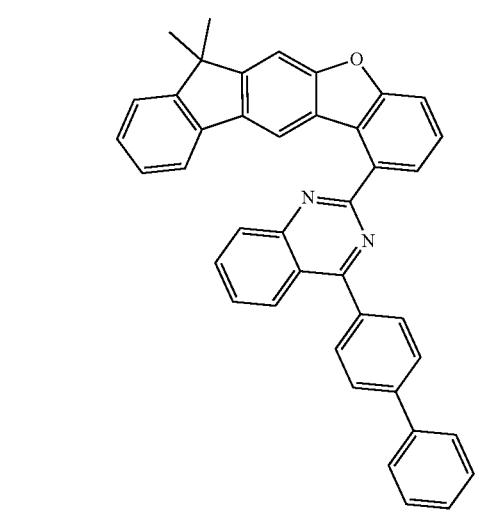
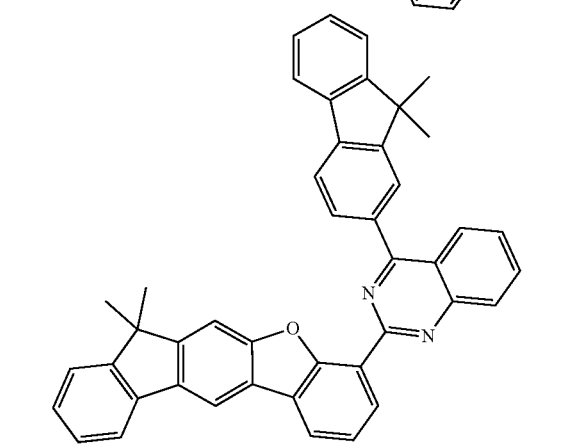

71
-continued
72
-continued
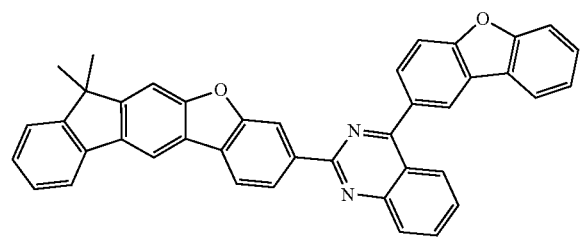
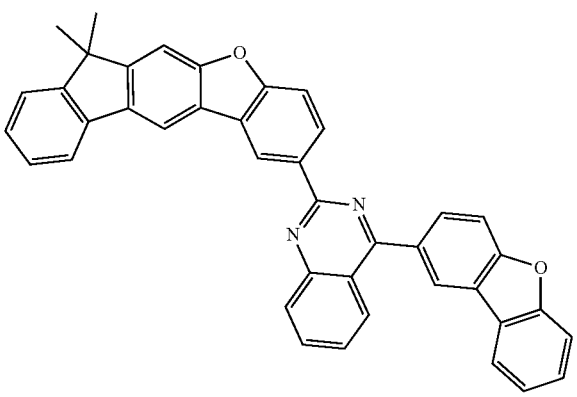
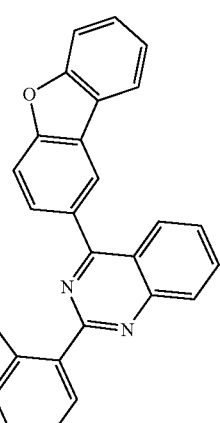
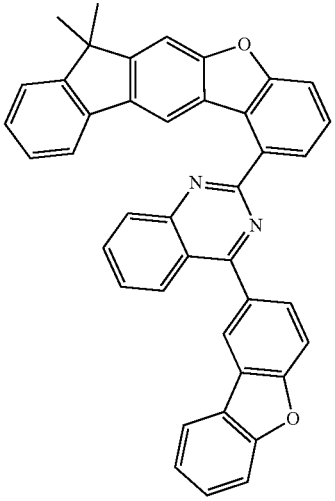
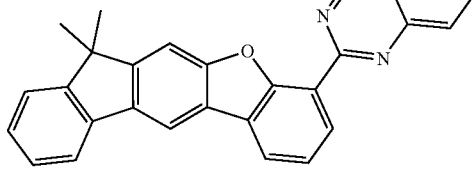
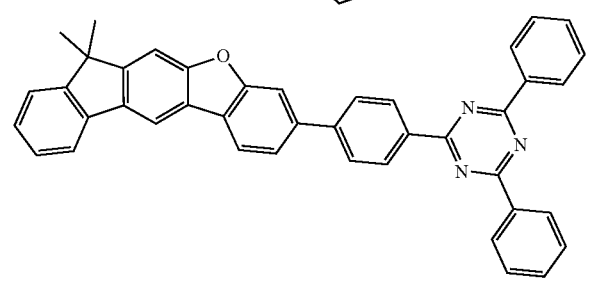
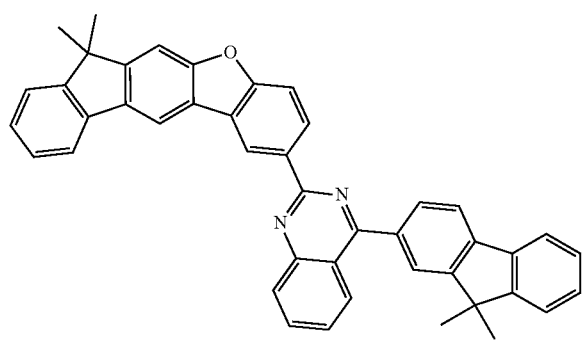
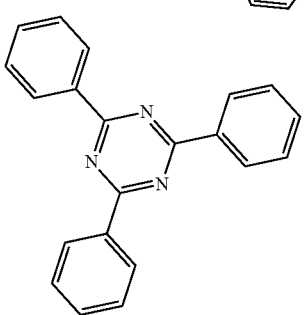
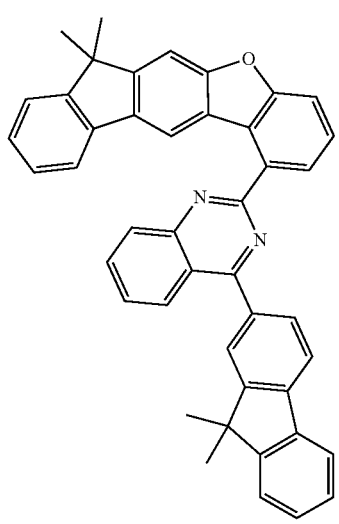
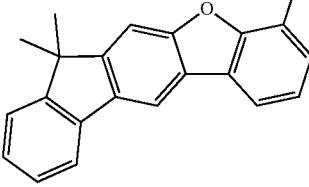

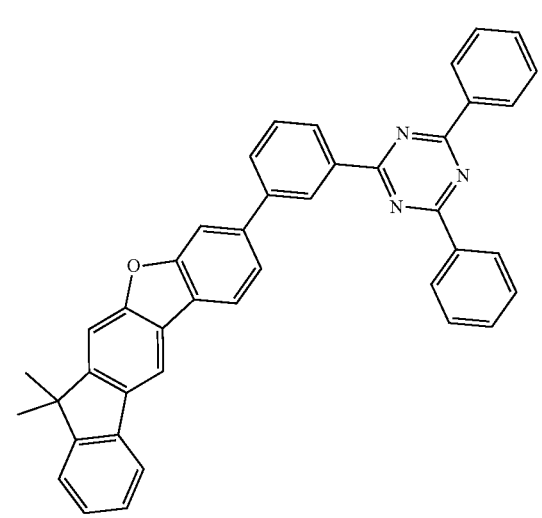
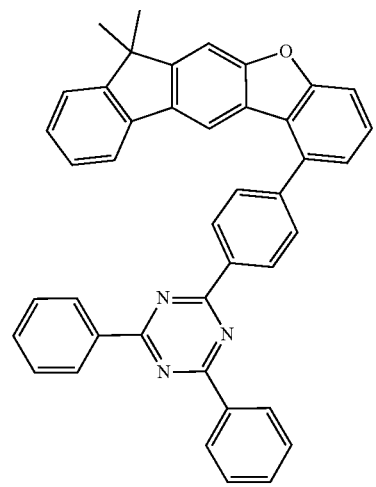
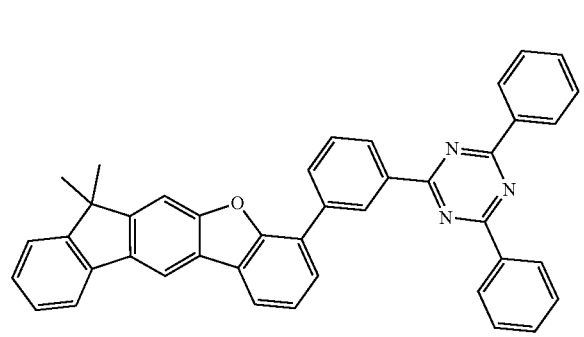
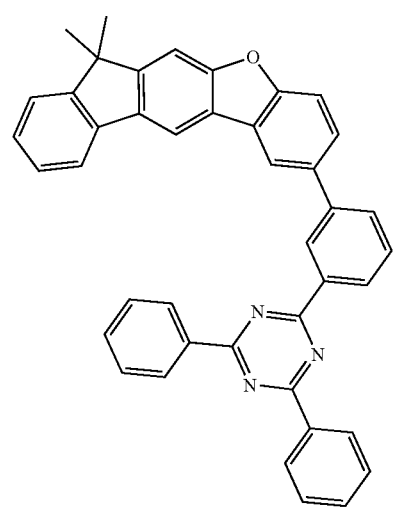
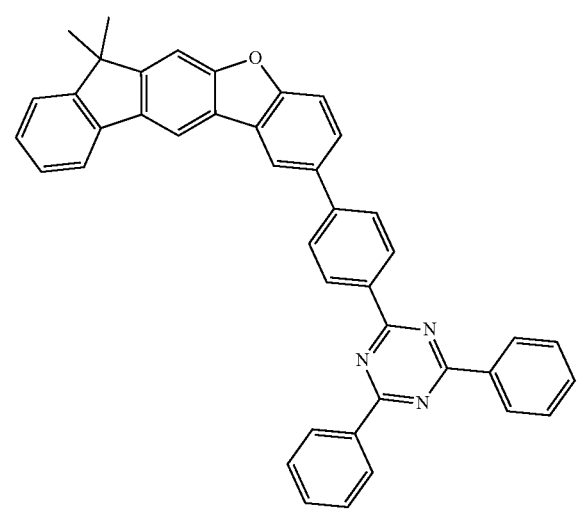
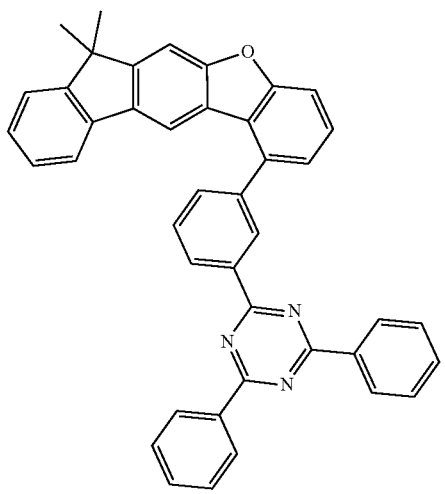

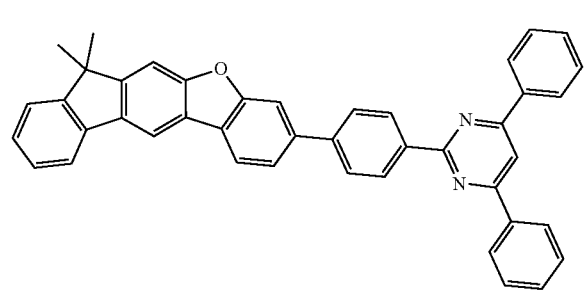
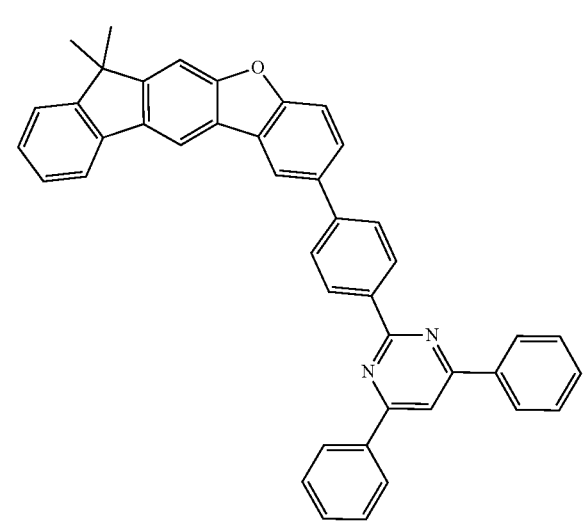
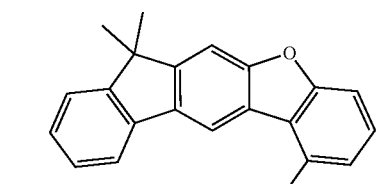
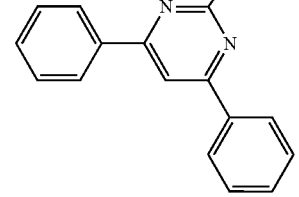
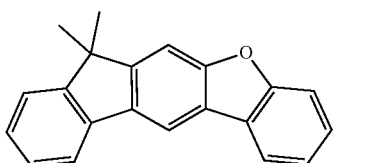
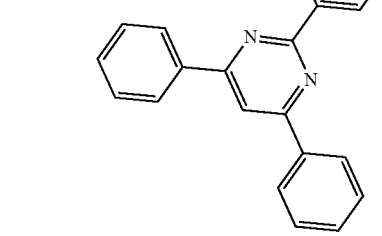

77
-continued
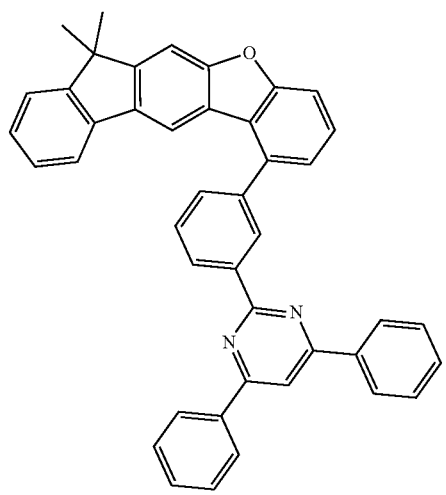
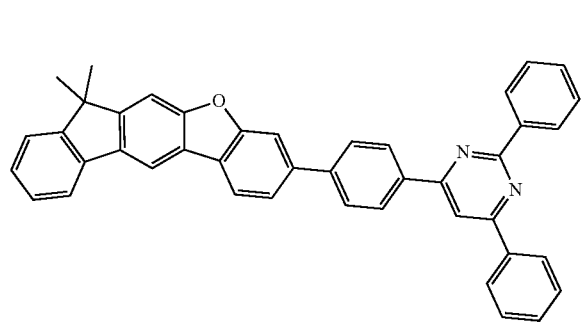
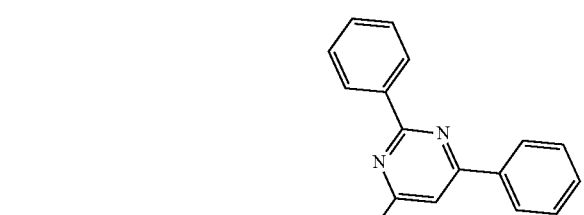
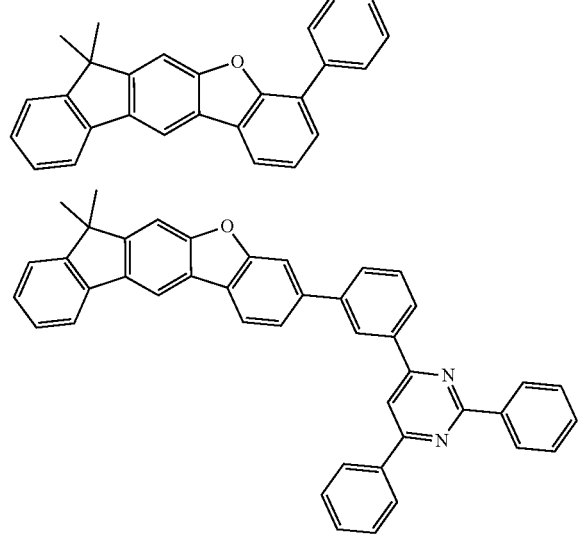
78
-continued
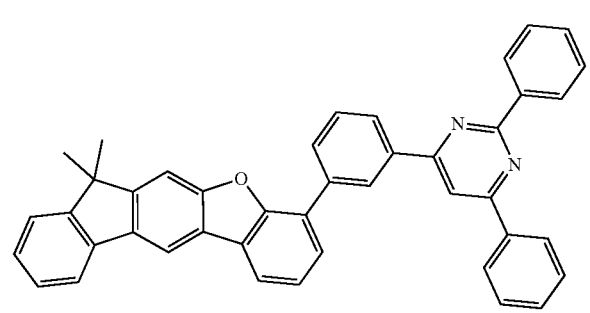
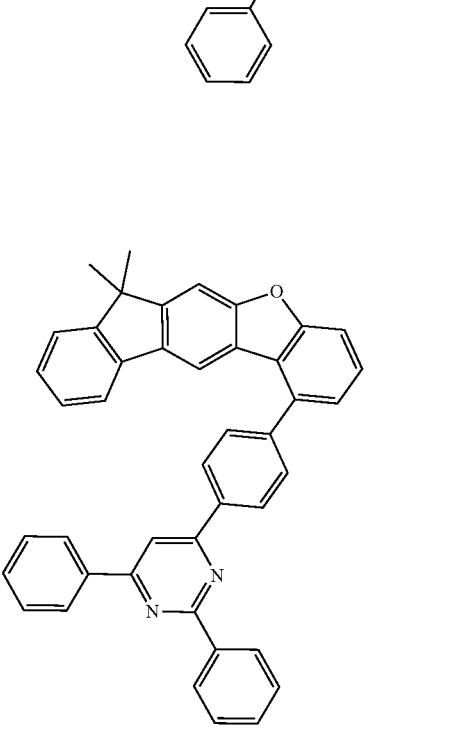

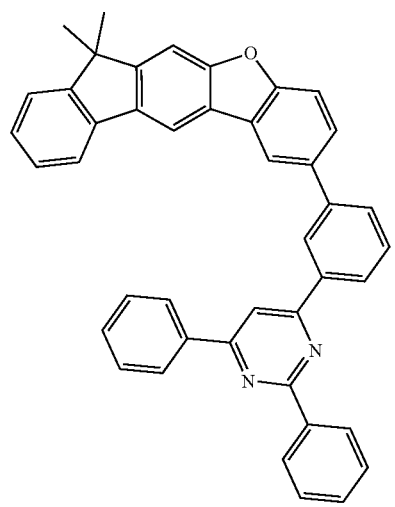
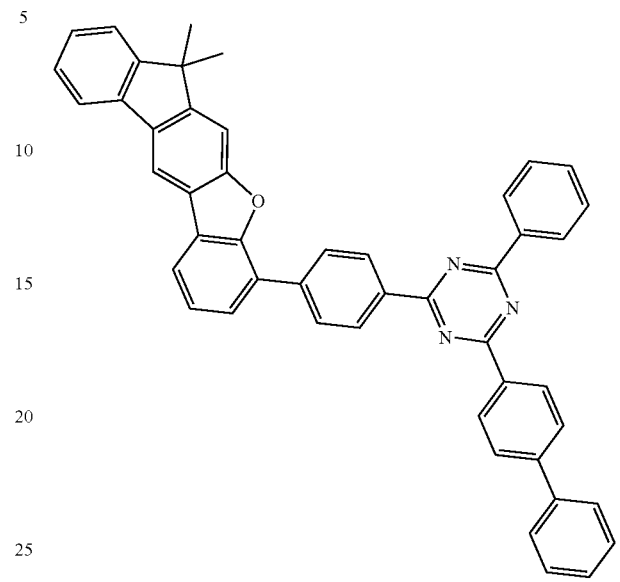
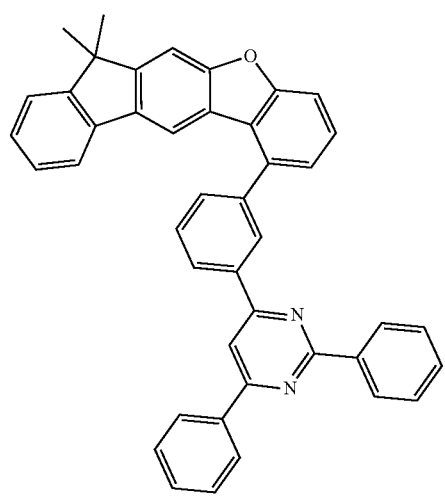
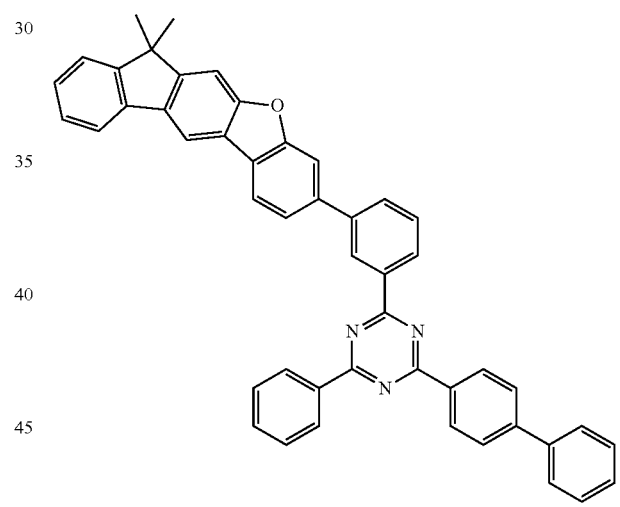
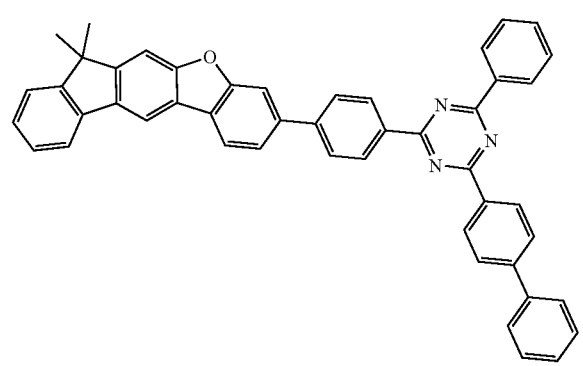

81
-continued
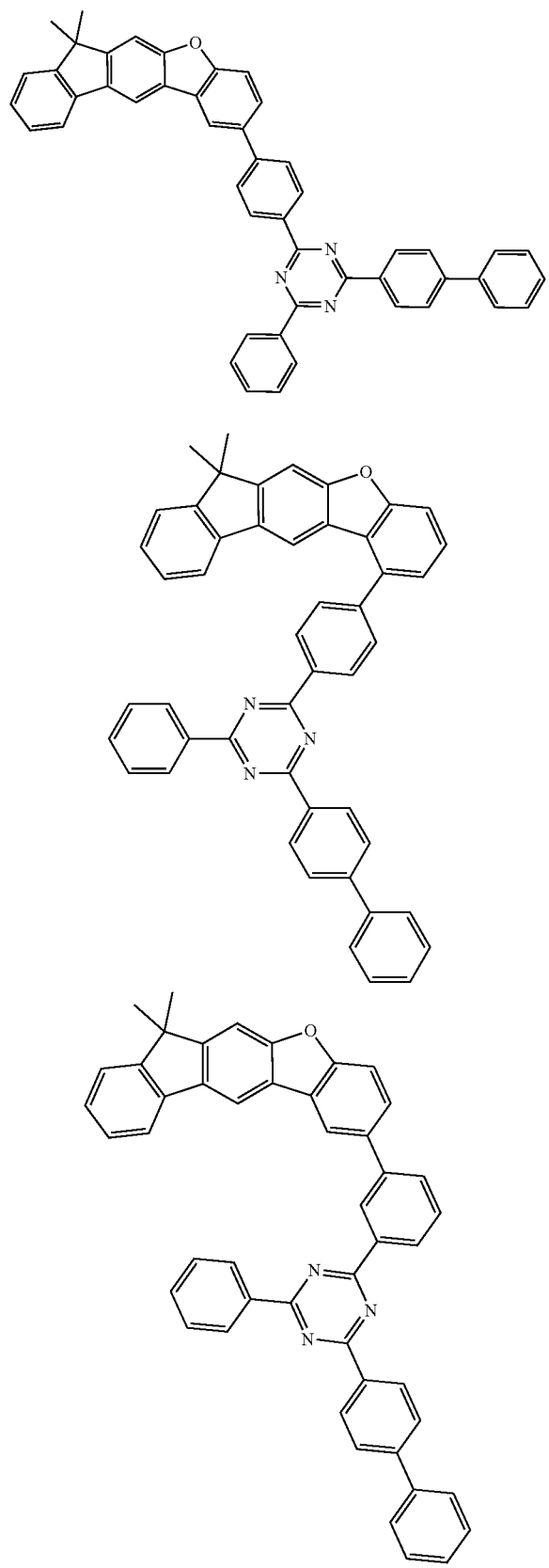
82
-continued
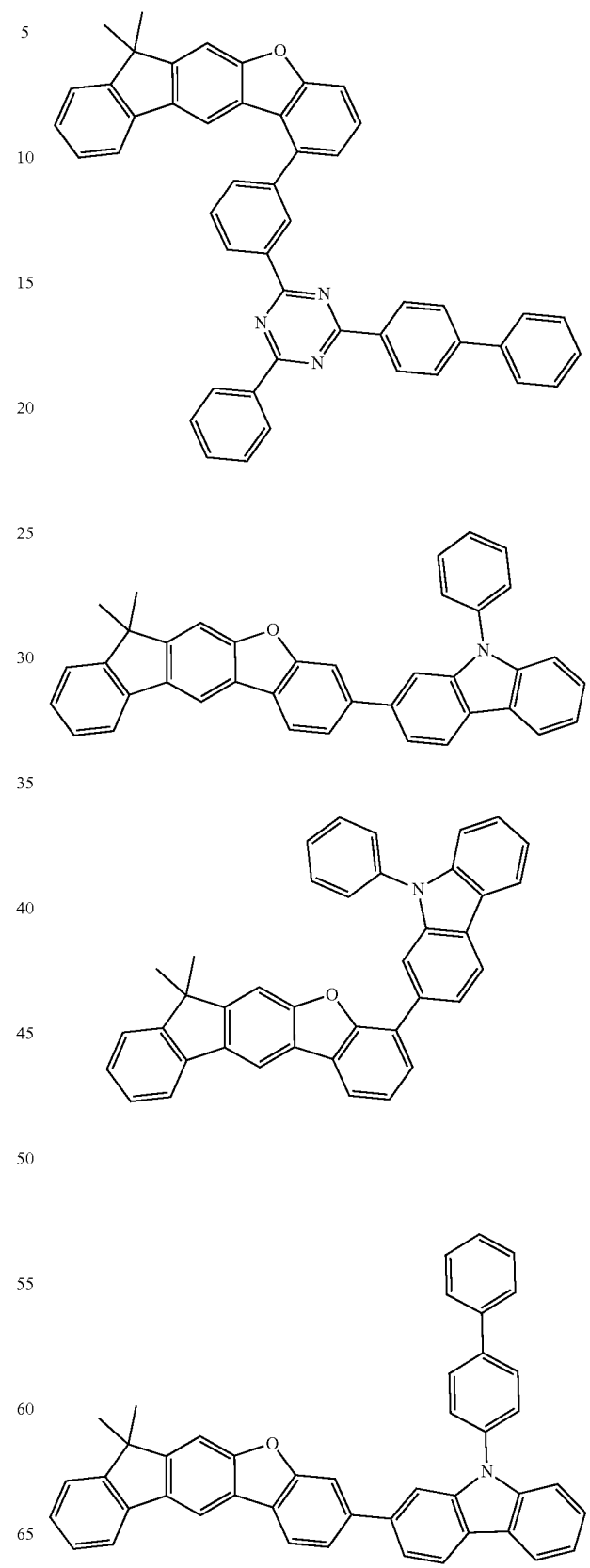

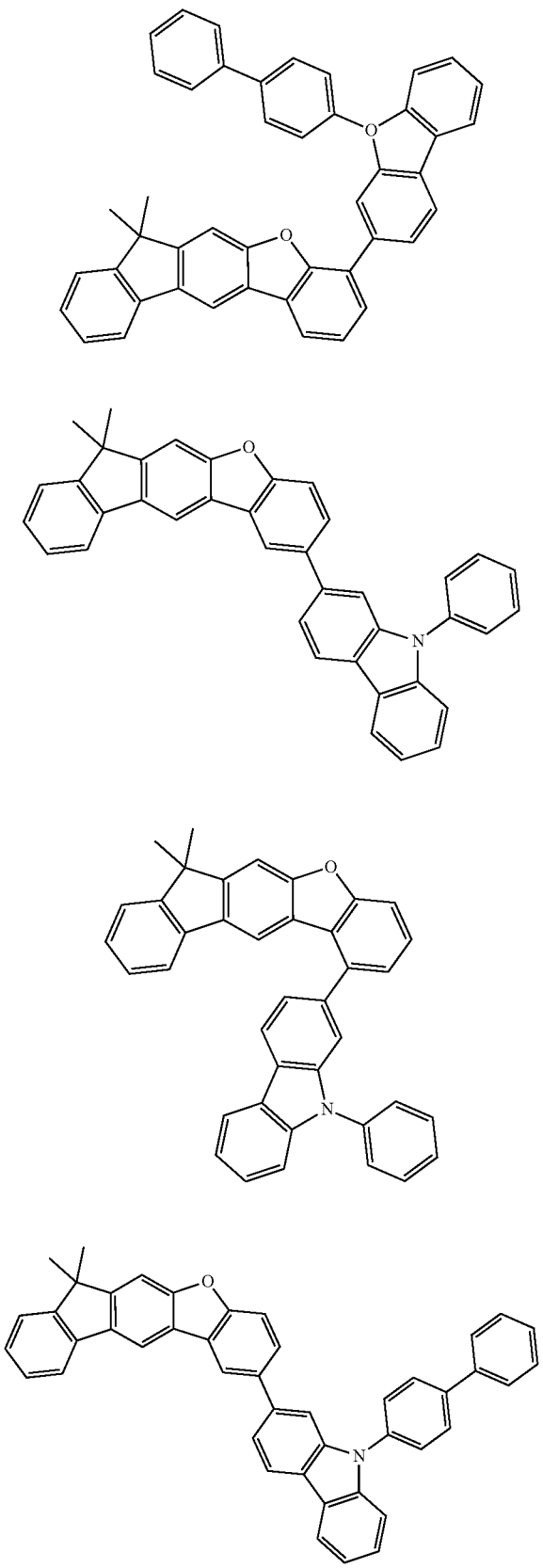
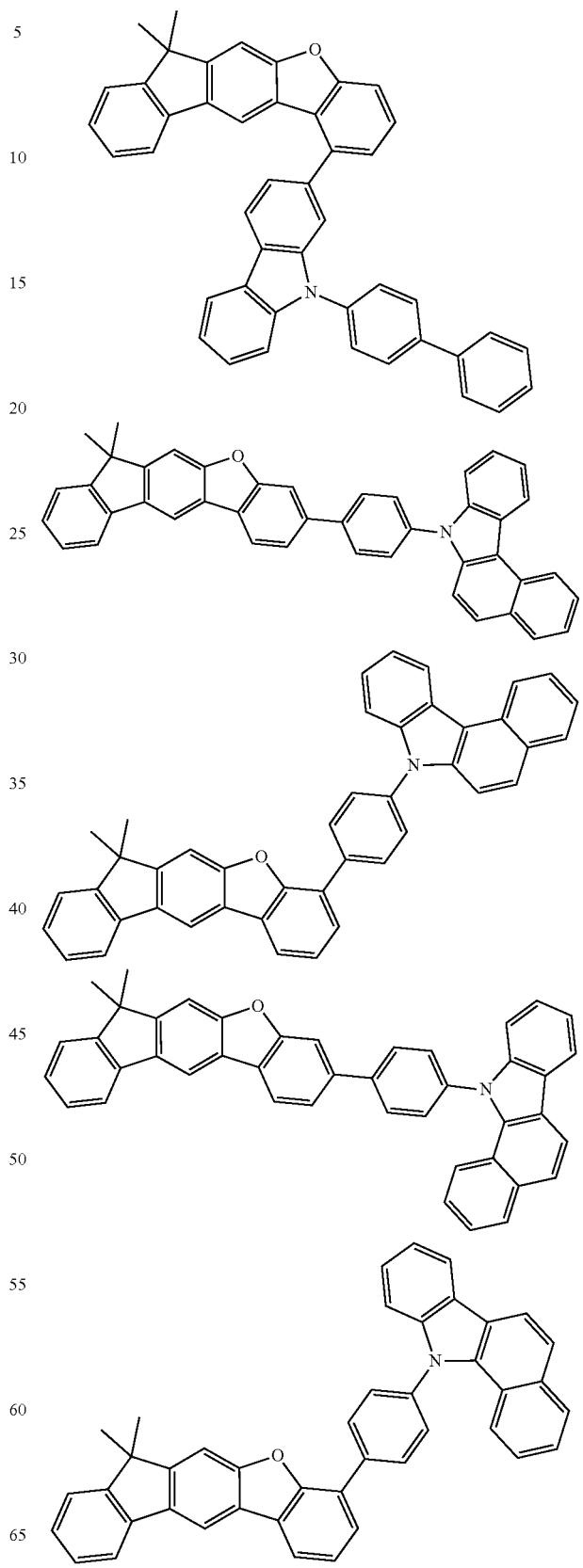

85
-continued
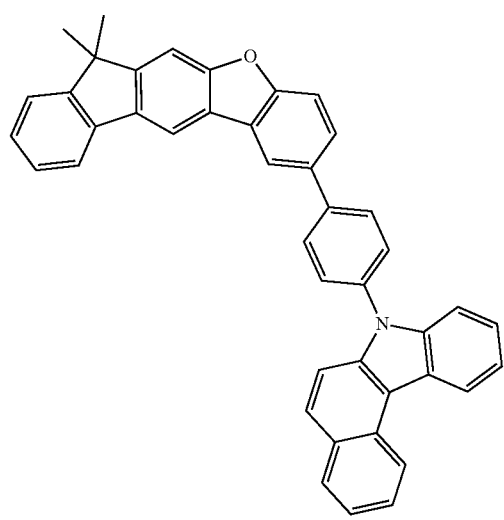
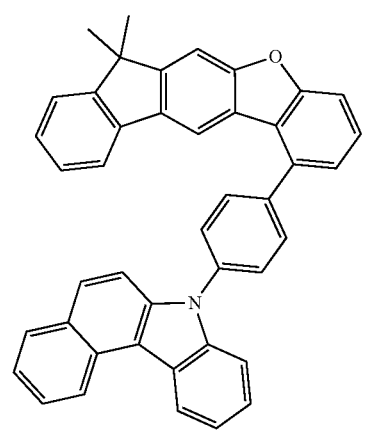
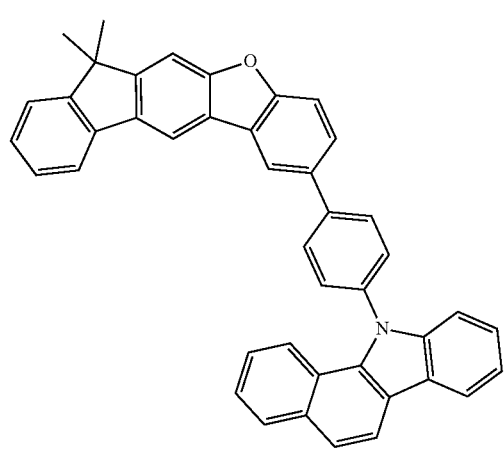
86
-continued
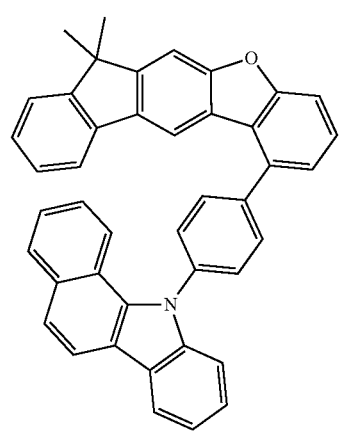
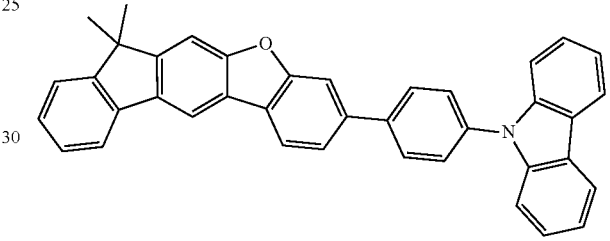
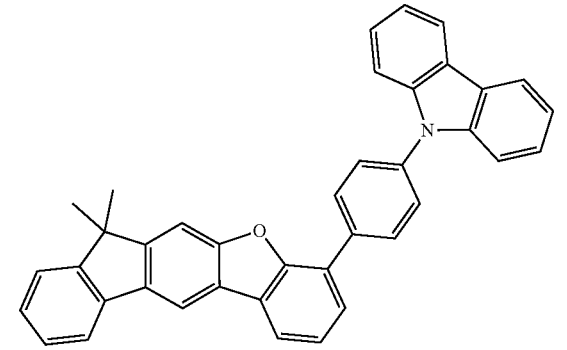
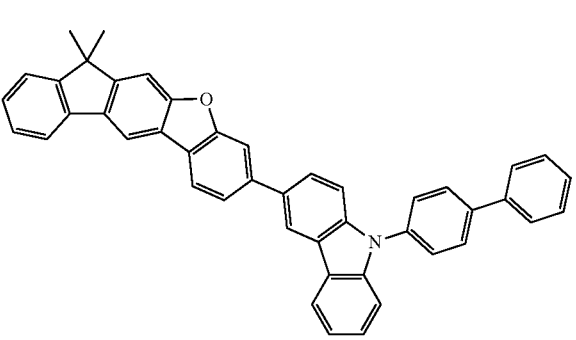

87
-continued
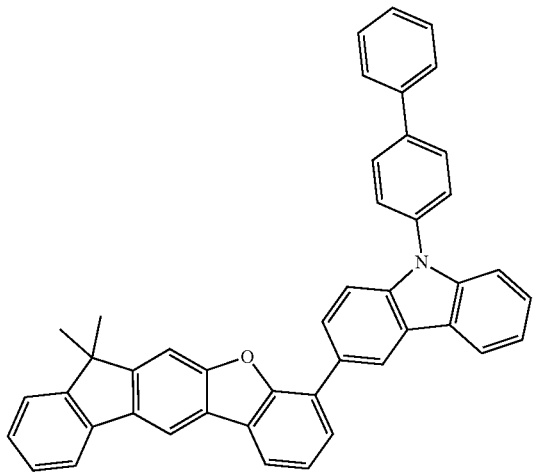
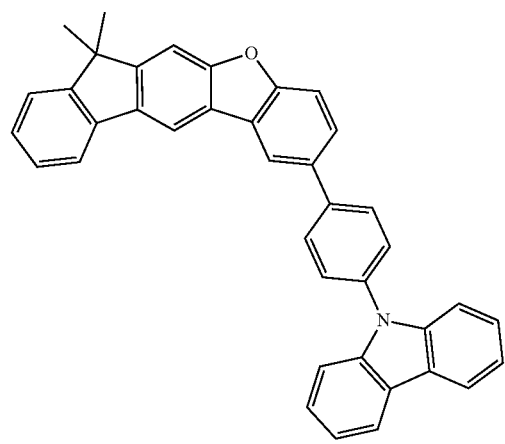
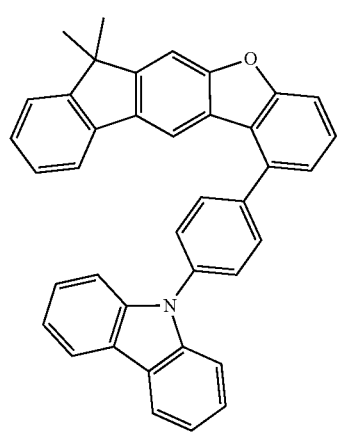
88
-continued
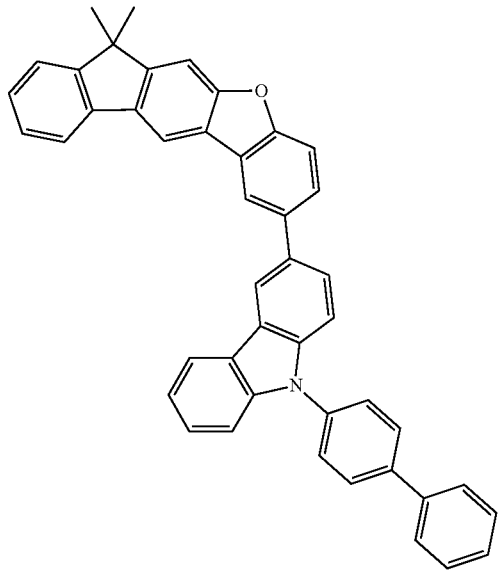
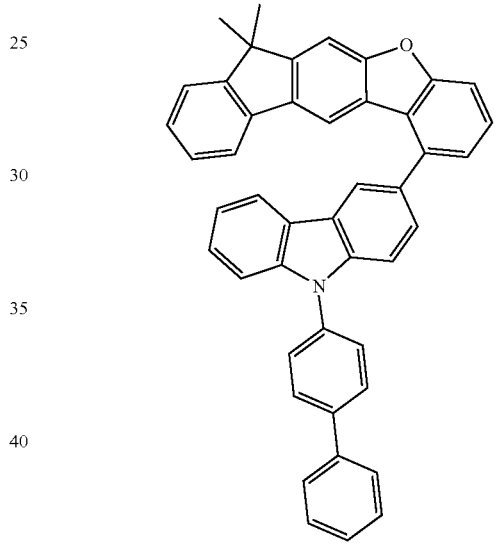
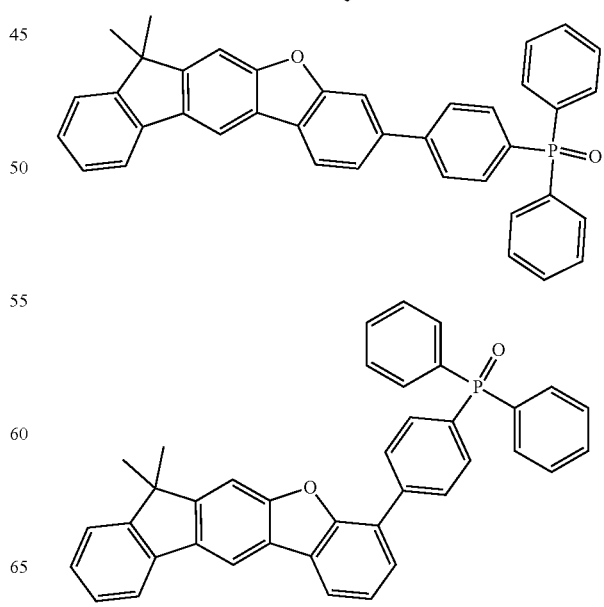

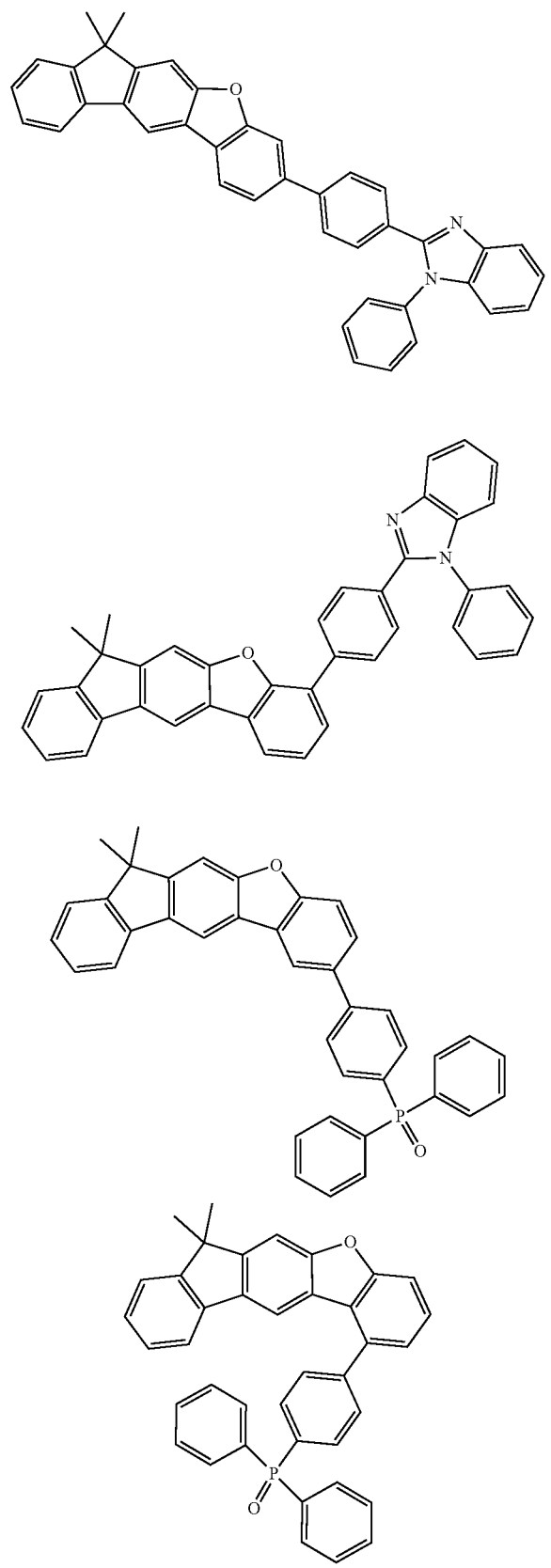
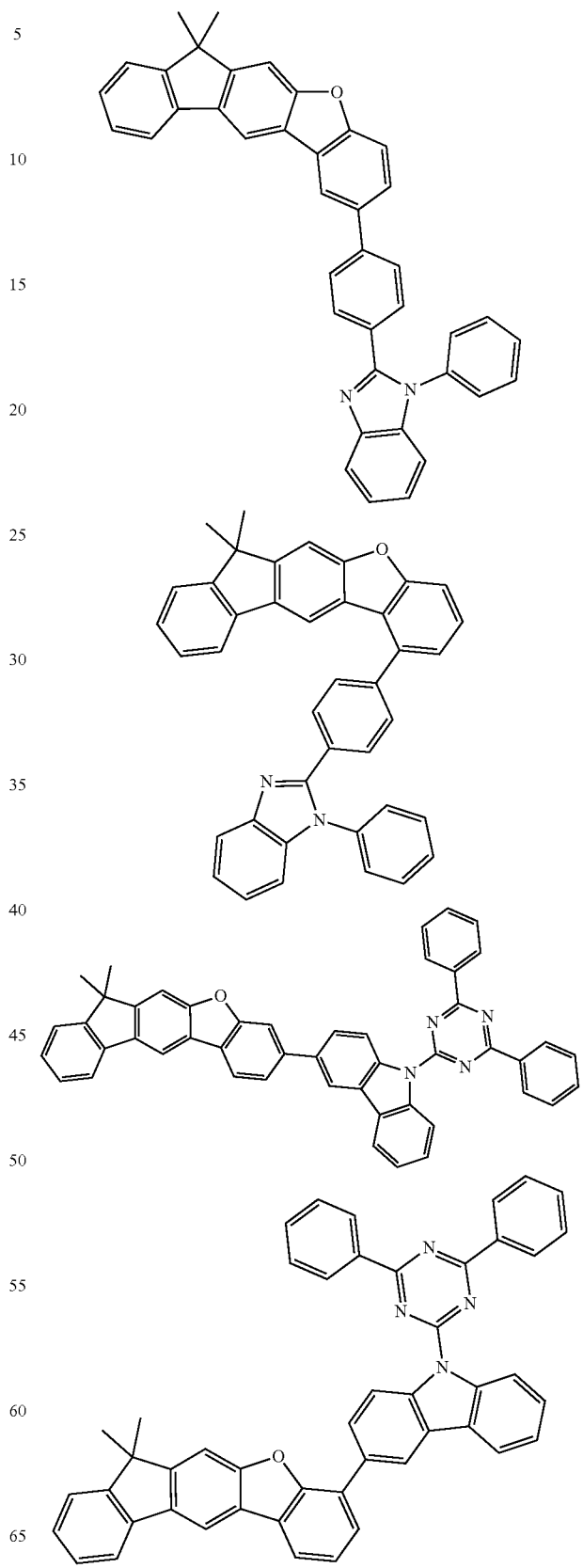

91
-continued
92
-continued
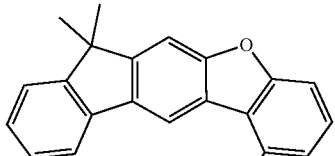
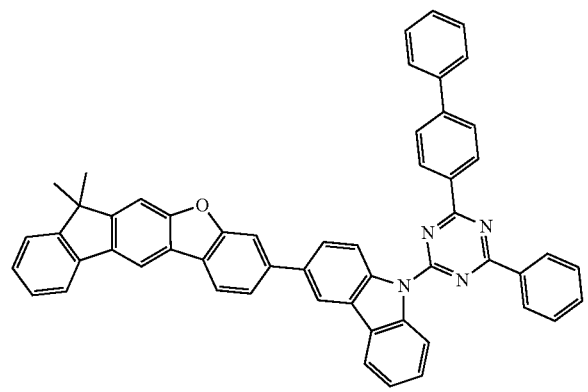
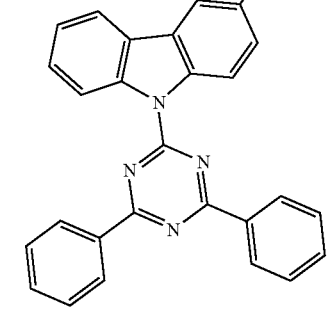
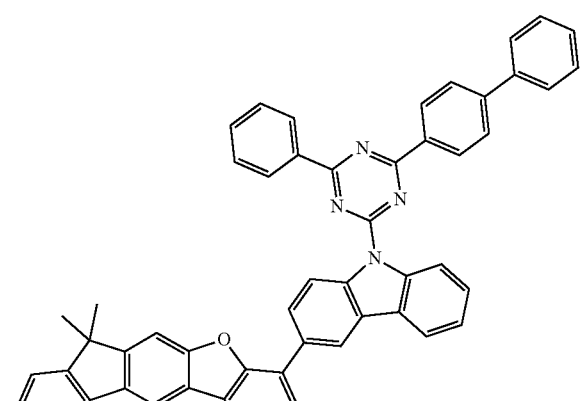
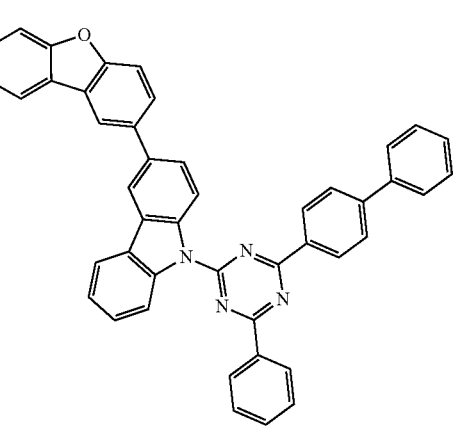
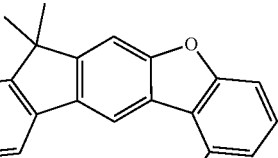
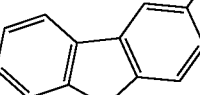
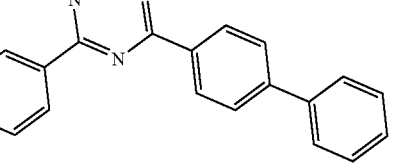
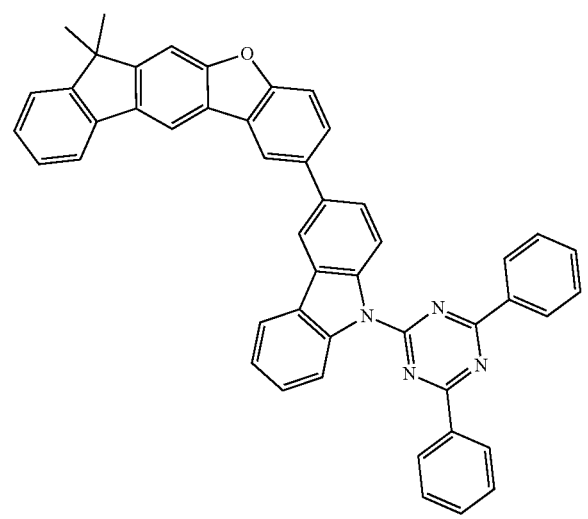
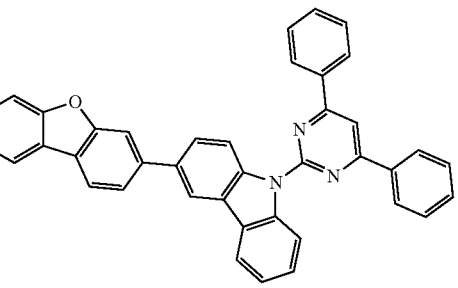

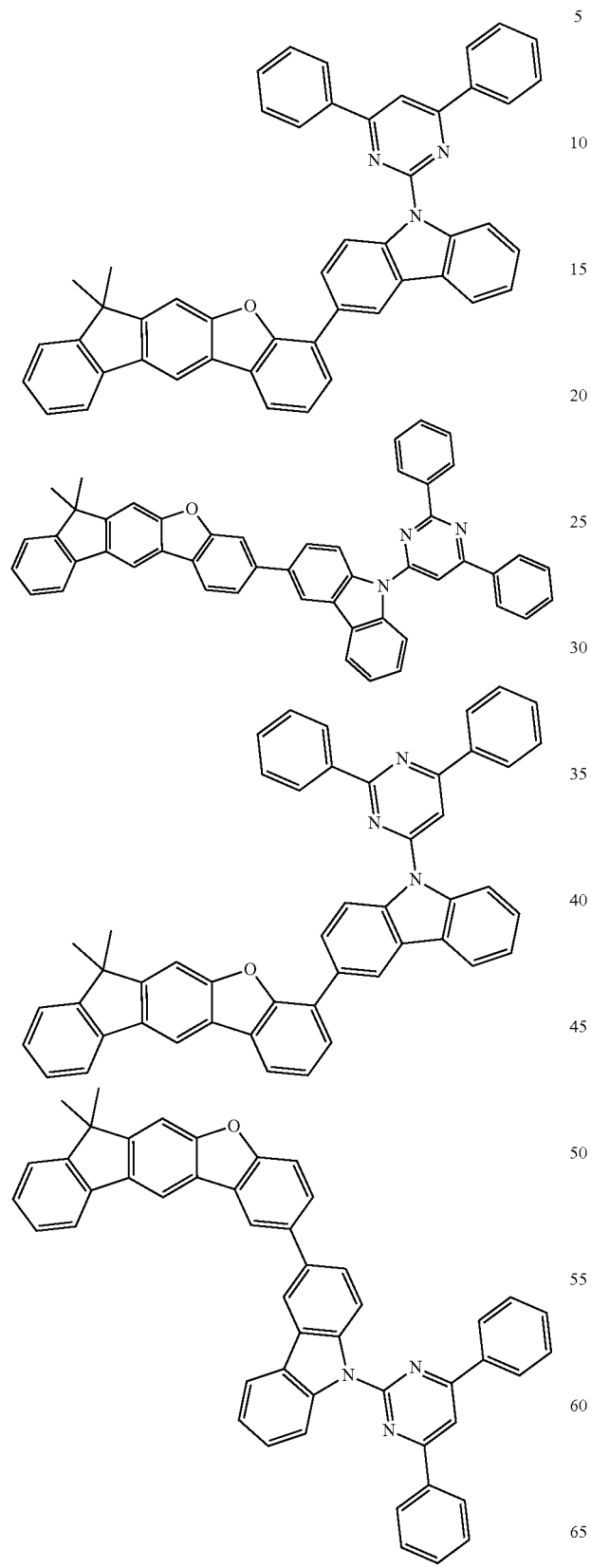
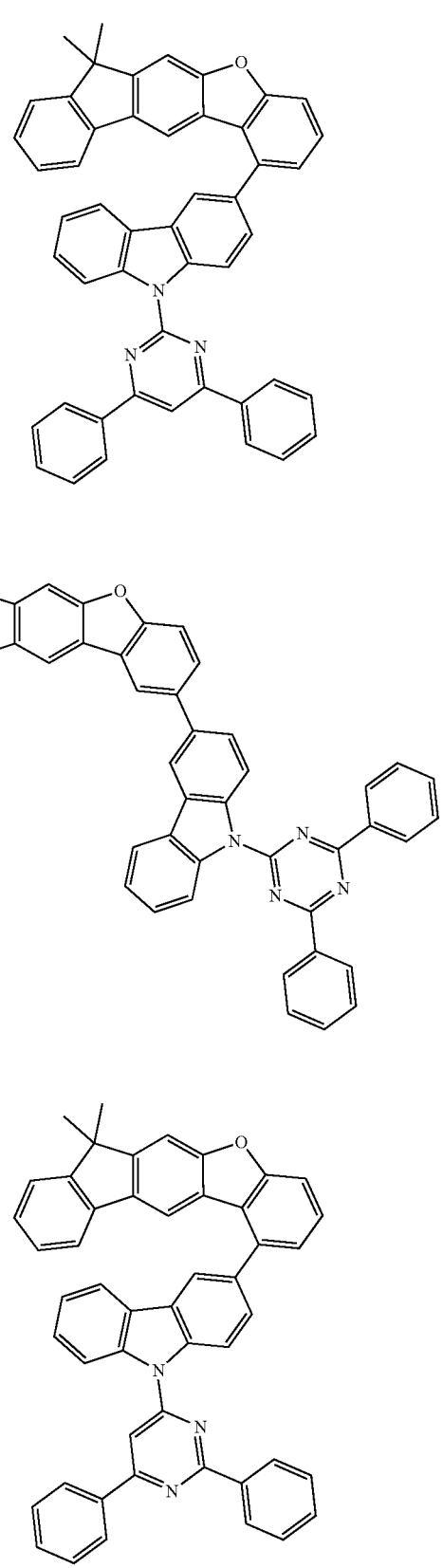

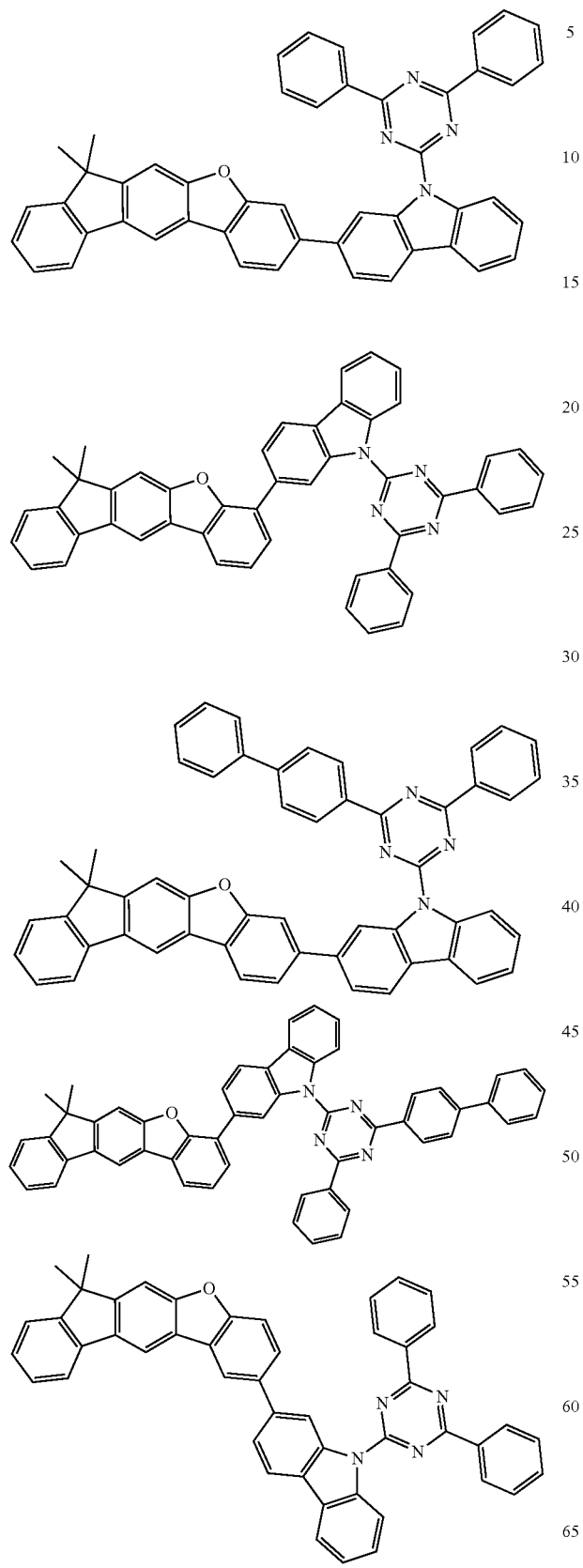
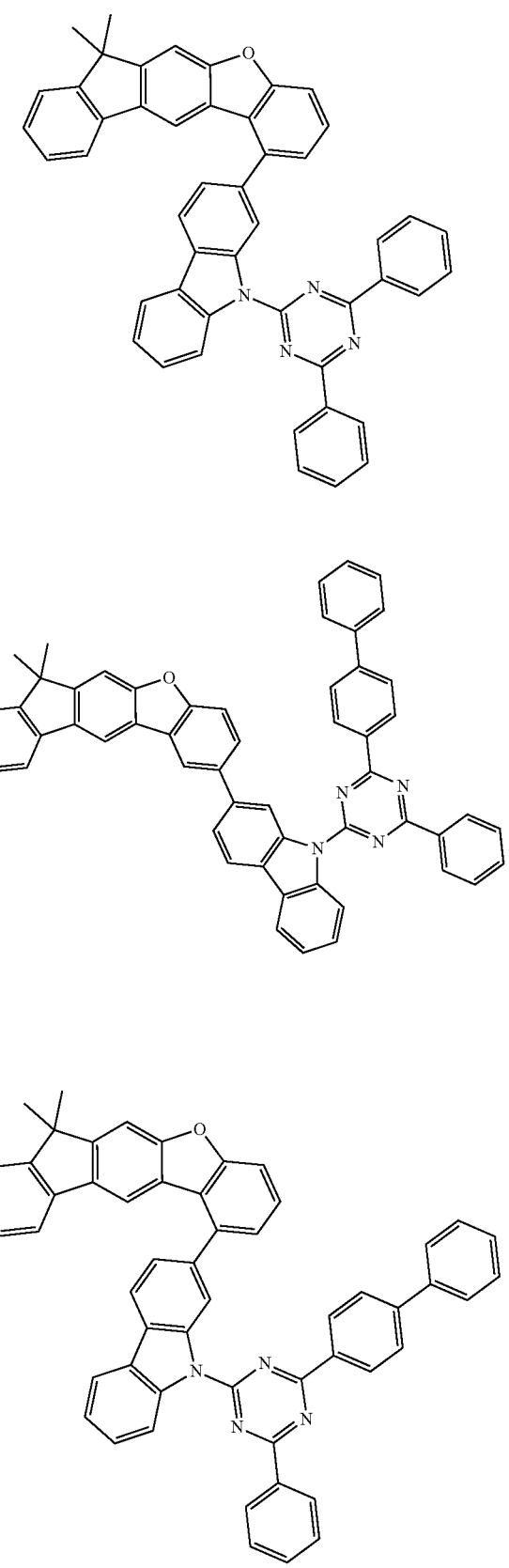

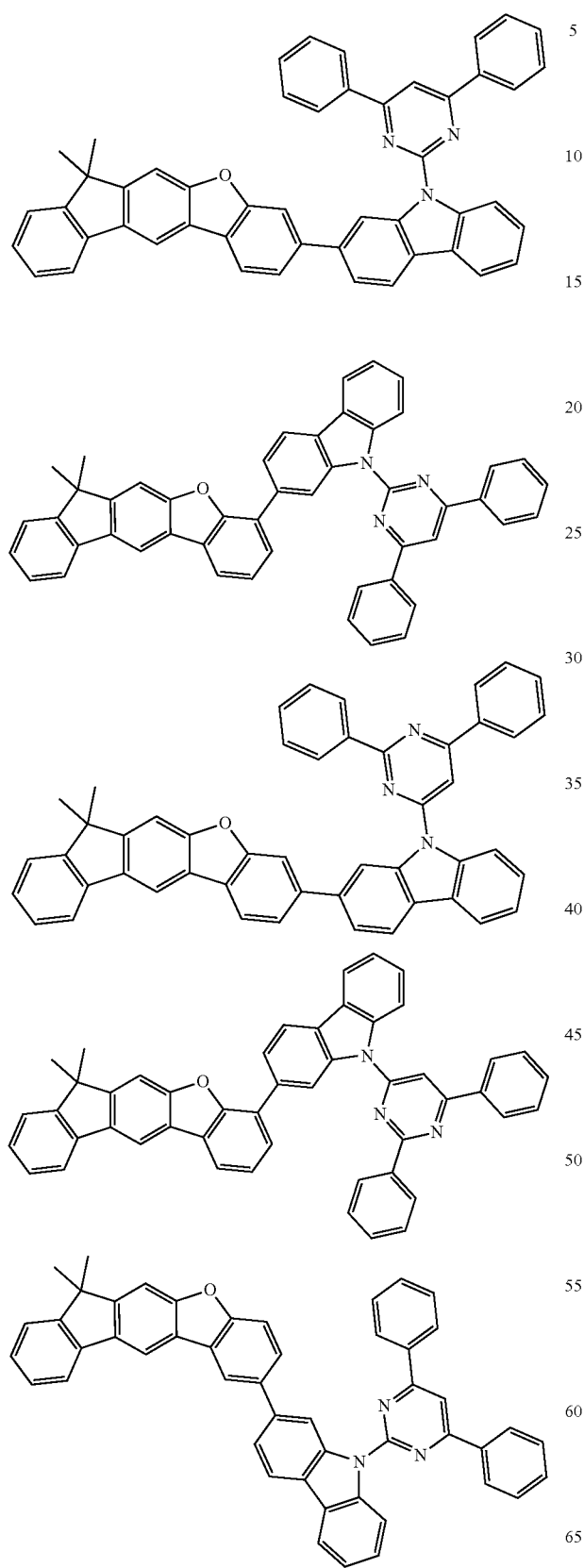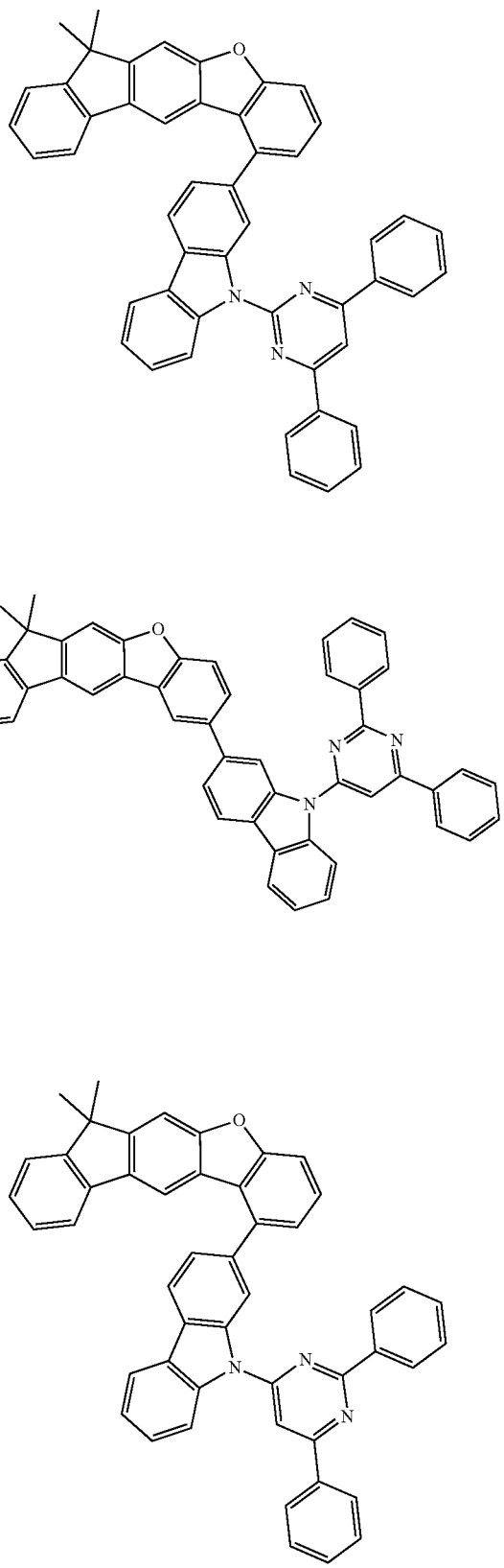

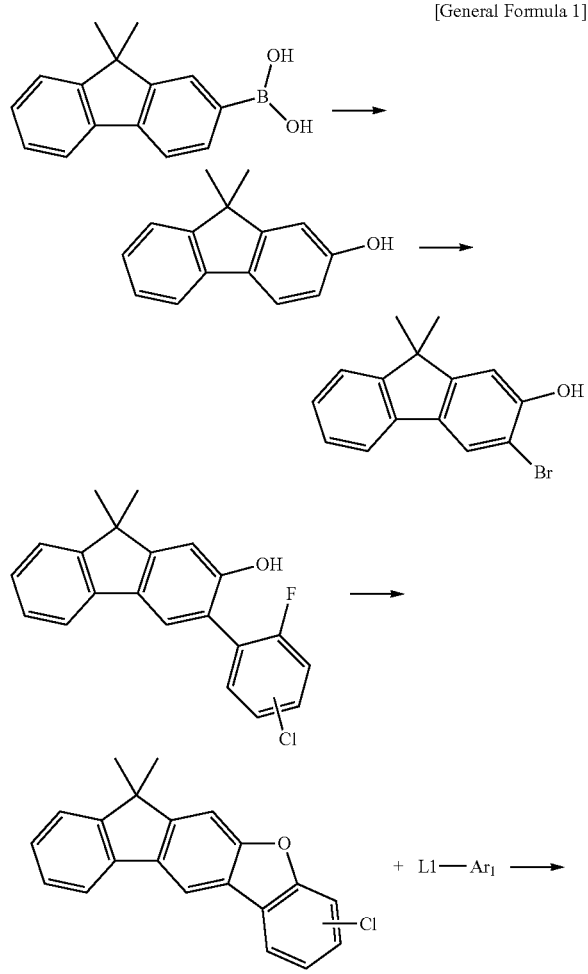

According to an exemplary embodiment of the present specification, a core structure of the hetero-cyclic compound represented by Chemical Formula 1 may be prepared by the following General Formula 1, but the preparation method thereof is not limited thereto.

[General Formula 1]

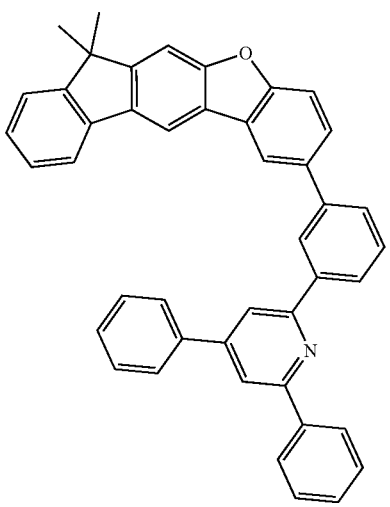

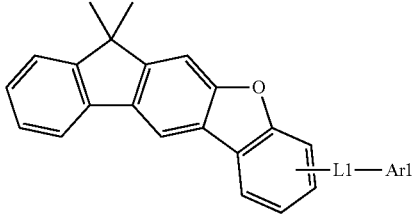

In General Formula 1, the definitions of L1 and Ar1 are the same as those in Chemical Formula 1.

An exemplary embodiment of the present specification provides an organic light emitting device including: a first electrode; a second electrode disposed to face the first electrode; and an organic material layer having one or more layers disposed between the first electrode and the second electrode, in which one or more layers of the organic material layer include the above-described hetero-cyclic compound.

According to an exemplary embodiment of the present specification, the organic material layer of the organic light emitting device of the present specification may be composed of a mono layer structure, but may be composed of a multi-layer structure in which two or more organic material layers are stacked. For example, the organic light emitting device of the present invention may have a structure including a hole injection layer, a hole transporting layer, an electron blocking layer, a light emitting layer, a hole blocking layer, an electron transporting layer, an electron injection layer, and the like as organic material layers. However, the structure of the organic light emitting device is not limited thereto, and may include fewer or more organic layers.

For example, the structure of the organic light emitting device of the present specification may have a structure as illustrated in FIGS. 1 and 2, but is not limited thereto.

FIG. 1 exemplifies the structure of an organic light emitting device 10 in which a first electrode 30, a light emitting layer 40, and a second electrode 50 are sequentially stacked on a substrate 20. FIG. 1 is an exemplified structure of the organic light emitting device according to an exemplary embodiment of the present specification, and may further include other organic material layers.

FIG. 2 exemplifies the structure of an organic light emitting device in which a first electrode 30, a hole injection layer 60, a hole transporting layer 70, a light emitting layer 40, an electron transporting layer 80, an electron injection layer 90, and a second electrode 50 are sequentially stacked on a substrate 20. FIG. 2 is an exemplified structure according to another exemplary embodiment of the present specification, and may further include other organic material layers.

According to an exemplary embodiment of the present specification, the organic material layer includes a hole transporting layer, and the hole transporting layer includes the hetero-cyclic compound represented by Chemical Formula 1.

According to an exemplary embodiment of the present specification, the organic material layer includes an electron blocking layer, and the electron blocking layer includes the hetero-cyclic compound represented by Chemical Formula 1.

According to an exemplary embodiment of the present specification, the organic material layer includes an electron transporting layer, and the electron transporting layer includes the hetero-cyclic compound represented by Chemical Formula 1.

According to an exemplary embodiment of the present specification, the organic material layer includes a light emitting layer, and the light emitting layer includes the hetero-cyclic compound represented by Chemical Formula 1.

According to an exemplary embodiment of the present specification, the organic material layer includes a light emitting layer, and the light emitting layer includes the hetero-cyclic compound represented by Chemical Formula 1 as a host of the light emitting layer.

In an exemplary embodiment of the present specification, the organic material layer may include the hetero-cyclic compound represented by Chemical Formula 1 as a host, and may include another organic compound, a metal or a metal compound as a dopant.

The dopant may be one or more selected from the following exemplified compounds, but is not limited thereto.

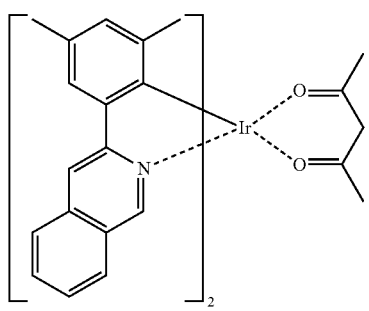
Dp-1

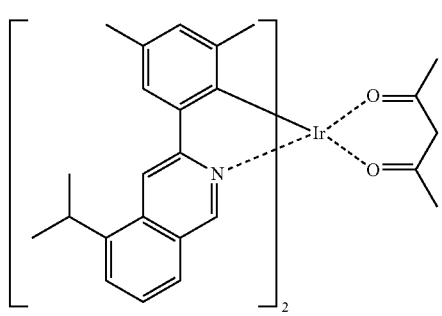
Dp-2

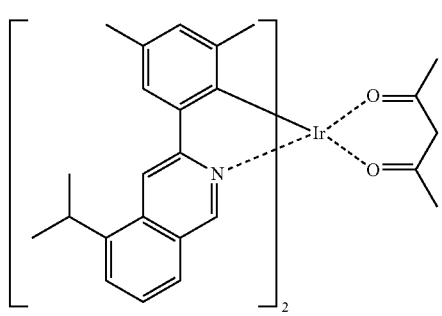
Dp-3

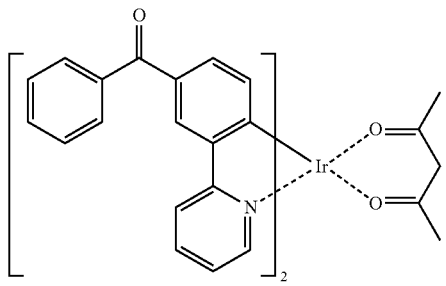
Dp-4

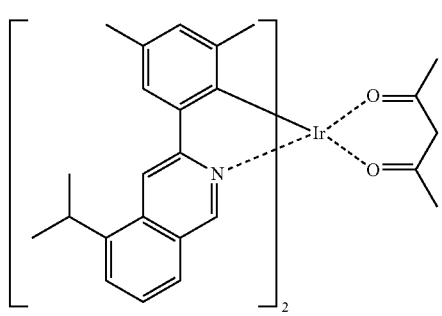
Dp-5

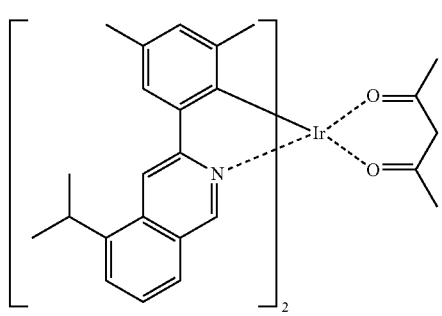
Dp-6

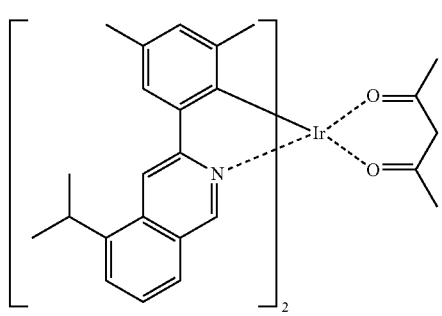
Dp-7

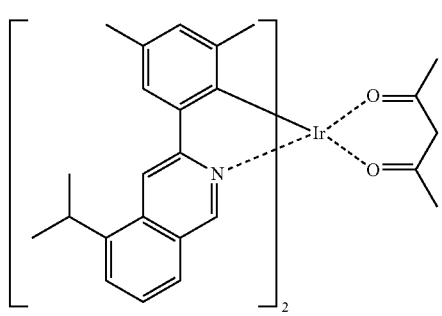
Dp-8

-continued
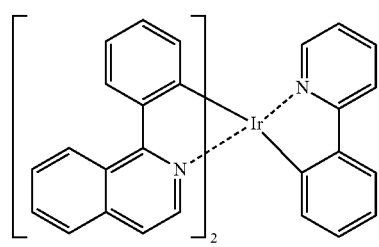
Dp-9
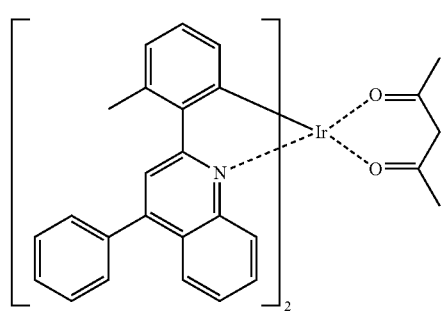
Dp-10
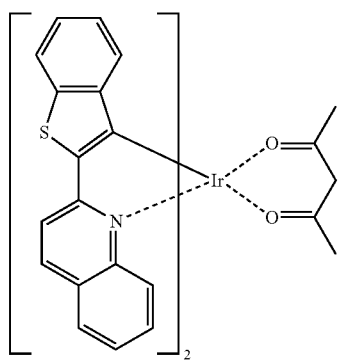
Dp-11
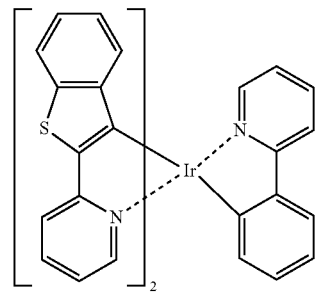
Dp-12
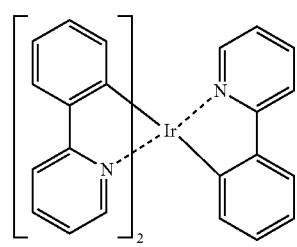
Dp-13
-continued
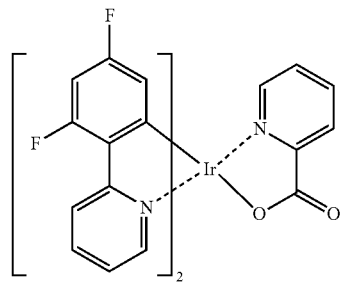
Dp-14
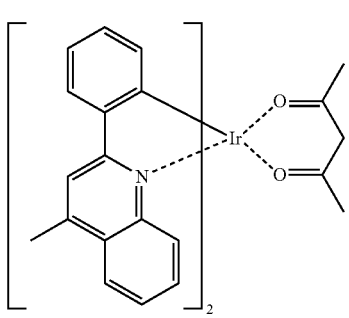
Dp-15
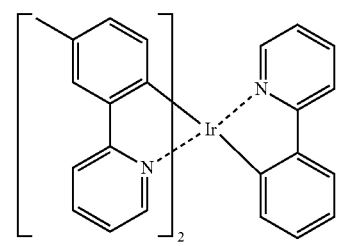
Dp-16
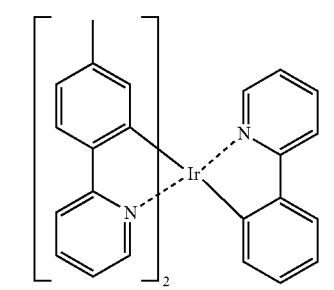
Dp-17
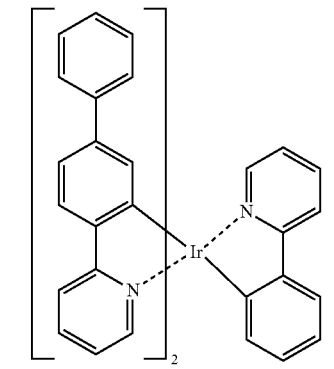
Dp-18

Dp-19

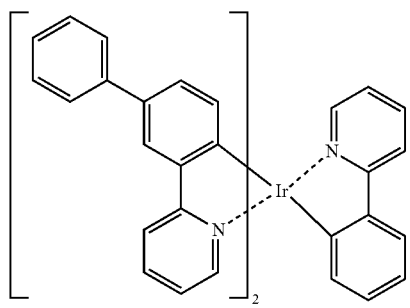

Dp-20

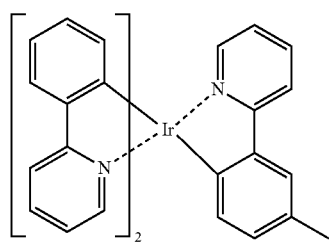

Dp-21

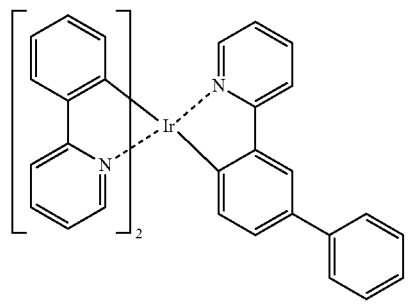

Dp-22

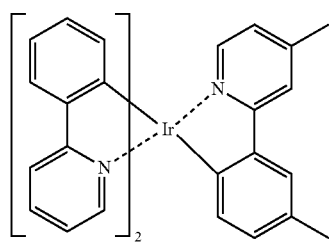

Dp-23

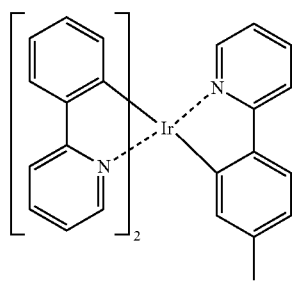

Dp-24

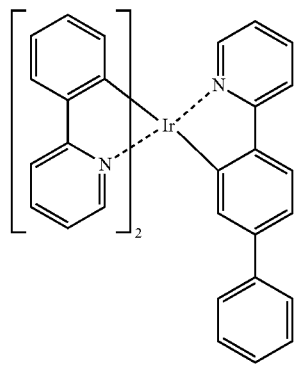

Dp-25

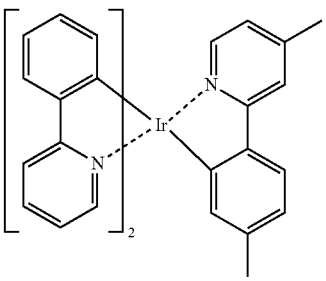

Dp-26

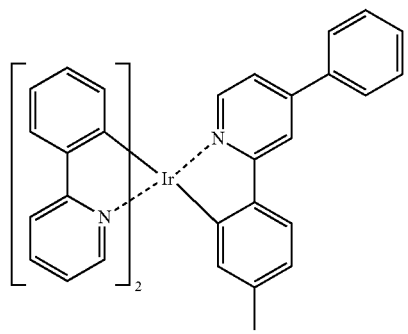

Dp-27

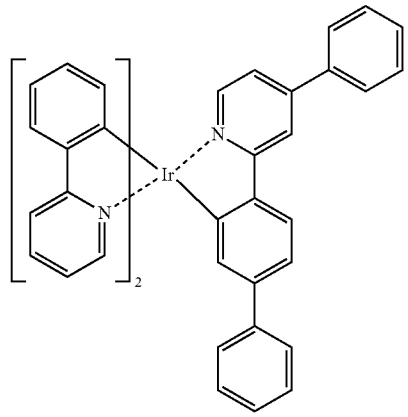

According to an exemplary embodiment of the present specification, the organic material layer may further include one or more layers selected from the group consisting of a hole injection layer, a hole transporting layer, a light emitting layer, an electron transporting layer, and an electron injection layer.

According to an exemplary embodiment of the present specification, the organic material layer includes an electron blocking layer, an electron transporting layer, or a light emitting layer.

The organic light emitting device of the present specification may be manufactured by the materials and methods known in the art, except that one or more layers of the organic material layer include the hetero-cyclic compound of the present specification, that is, the hetero-cyclic compound represented by Chemical Formula 1.

When the organic light emitting device includes a plurality of organic material layers, the organic material layers may be formed of the same material or different materials.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a first electrode, forming an organic material layer including a hole injection layer, a hole transporting layer, a light emitting layer, and an electron transporting layer thereon, and then depositing a material, which may be used as a second electrode, thereon, by using a physical vapor deposition (PVD) method such as sputtering or e-beam evaporation. In addition to the method described above, an organic light emitting device may be made by sequentially depositing a second electrode material, an organic material layer, and a first electrode material on a substrate. Further, the hetero-cyclic compound represented by Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

According to an exemplary embodiment of the present specification, the first electrode is a positive electrode, and the second electrode is a negative electrode.

According to another exemplary embodiment of the present specification, the first electrode is a negative electrode, and the second electrode is a positive electrode.

As the positive electrode material, materials having a high work function are usually preferred so as to facilitate the injection of holes into an organic material layer. Specific examples of the positive electrode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or SnO$_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

As the negative electrode material, materials having a low work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or LiO$_2$/Al and Mg/Ag, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transporting layer is a layer which accepts holes from a hole injection layer and transports the holes to a light emitting layer, and a hole transporting material is suitably a material having high hole mobility which may accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

A light emitting material for the light emitting layer is a material which may emit light in a visible light region by accepting and combining holes and electrons from a hole transporting layer and an electron transporting layer, respectively, and is preferably a material having high quantum efficiency for fluorescence or phosphorescence. Specific examples thereof include: an 8-hydroxy-quinoline aluminum complex (Alq$_3$); carbazole-based compounds; dimerized styryl compounds; BAlq; 10-hydroxybenzoquinoline-metal compounds; benzoxazole-based, benzothiazole-based and benzimidazole-based compounds; poly(p-phenylenevinylene) (PPV)-based polymers; spiro compounds; polyfluorene, lubrene, and the like, but are not limited thereto.

The light emitting layer may include a host material and a dopant material. Examples of the host material include a fused aromatic ring derivative, or a hetero ring-containing compound, and the like. Specifically, examples of the fused aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting layer is a layer which accepts electrons from an electron injection layer and transports the electrons to a light emitting layer, and an electron transporting material is suitably a material having high electron mobility which may proficiently accept electrons from a negative electrode and transfer the electrons to a light emitting layer. Specific examples thereof include: Al complexes of 8-hydroxyquinoline; complexes including Alq$_3$; organic radical compounds; hydroxyflavone-metal complexes, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The organic light emitting device according to the present specification may be a top emission type, a bottom emission type, or a dual emission type according to the materials to be used.

According to an exemplary embodiment of the present specification, the hetero-cyclic compound represented by Chemical Formula 1 may be included in an organic solar cell or an organic transistor in addition to the organic light emitting device.

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

By the following Reaction Formula 1, Compounds A to H were prepared.

[Reaction Formula 1]

<Preparation Example 1> Preparation of Compound 1

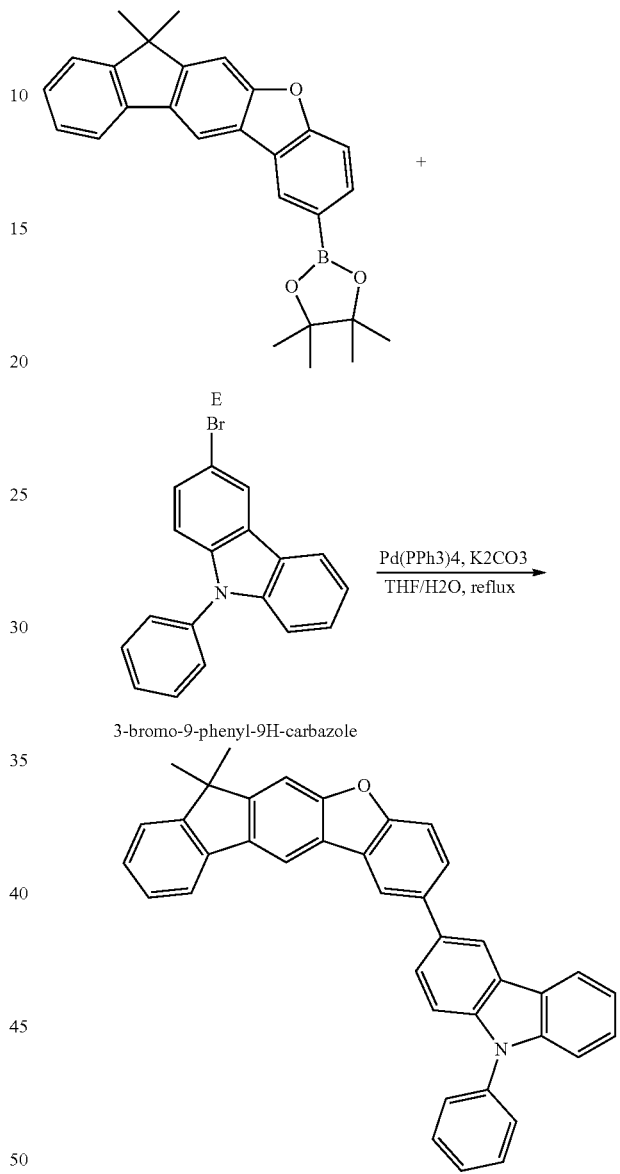

Compound E (12.13 g, 29.60 mmol) and 3-bromo-9-phenyl-9H-carbazole (10.0 g, 31.15 mmol) were completely dissolved in 240 ml of tetrahydrofuran in a 500-ml round bottom flask under a nitrogen atmosphere, and then an aqueous 2 M potassium carbonate solution (120 ml) was added thereto, tetrakis-(triphenylphosphine)palladium (0.65 g, 0.59 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 170 ml of ethyl acetate to prepare Compound 1 (16.66 g, 82%).

MS[M+H]$^+$=526

<Preparation Example 2> Preparation of Compound 2

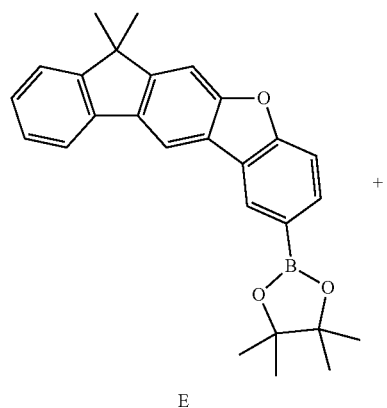

E

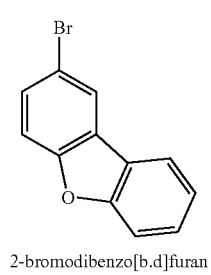

2-bromodibenzo[b,d]furan

Pd(PPh3)4, K2CO3
THF/H2O, reflux

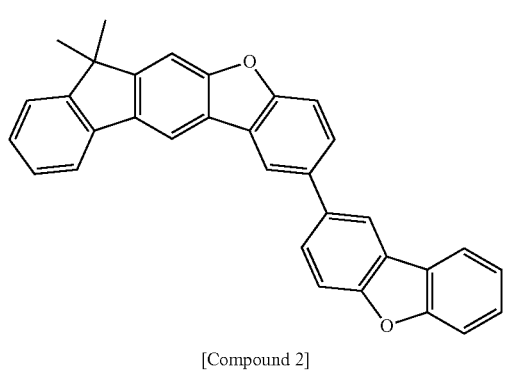

[Compound 2]

Compound E (15.90 g, 38.78 mmol) and 2-bromodibenzo[b,d]furan (10.0 g, 40.80 mmol) were completely dissolved in 200 ml of tetrahydrofuran in a 500-ml round bottom flask under a nitrogen atmosphere, and then an aqueous 2 M potassium carbonate solution (100 ml) was added thereto, tetrakis-(triphenylphosphine)palladium (0.75 g, 0.67 mmol) was put thereinto, and then the resulting mixture was heated and stirred for 2 hours. The temperature was lowered to room temperature, the aqueous layer was removed, and the residue was dried over anhydrous magnesium sulfate, and then concentrated under reduced pressure, and recrystallized with 150 ml of ethyl acetate to prepare Compound 2 (19.45 g, 83%).

MS[M+H]$^+$=451

<Preparation Example 3> Preparation of Compound 3

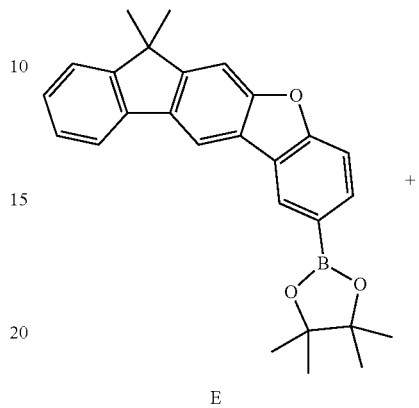

E

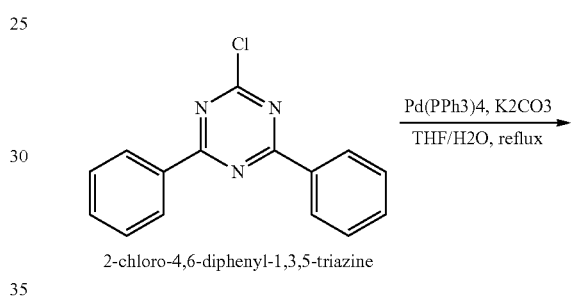

2-chloro-4,6-diphenyl-1,3,5-triazine

Pd(PPh3)4, K2CO3
THF/H2O, reflux

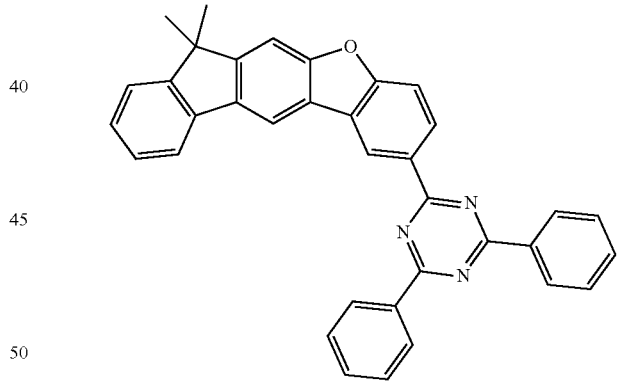

[Compound 3]

Compound E (14.59 g, 35.58 mmol) and 2-chloro-4,6-diphenyl-1,3,5-triazine (10.0 g, 37.45 mmol) were completely dissolved in 300 ml of tetrahydrofuran in a 500-ml round bottom flask under a nitrogen atmosphere, and then an aqueous 2 M potassium carbonate solution (150 ml) was added thereto, tetrakis-(triphenylphosphine)palladium (0.87 g, 0.75 mmol) was put thereinto, and then the resulting mixture was heated and stirred for 2 hours. The temperature was lowered to room temperature, the aqueous layer was removed, and the residue was dried over anhydrous magnesium sulfate, and then concentrated under reduced pressure, and recrystallized with 340 ml of ethyl acetate to prepare Compound 3 (19.45 g, 83%).

MS[M+H]$^+$=516

\<Preparation Example 4\> Preparation of Compound 4

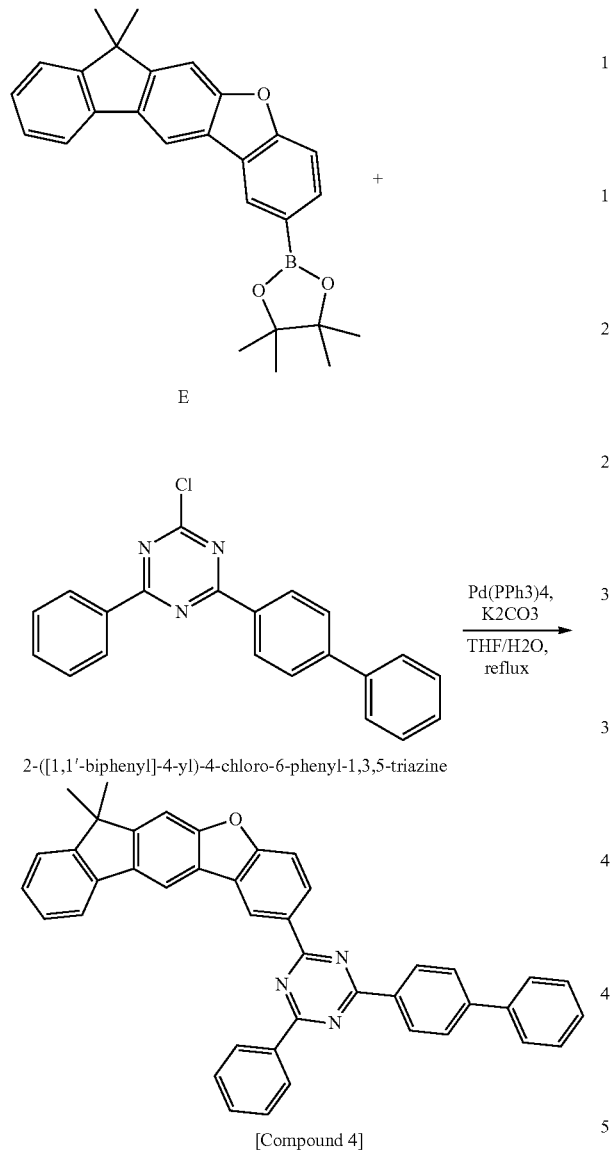

[Compound 4]

Compound E (11.36 g, 27.70 mmol) and 2-([1,1'-biphenyl]-4-yl)-4-chloro-6-phenyl-1,3,5-triazine (10.0 g, 29.15 mmol) were completely dissolved in 360 ml of tetrahydrofuran in a 500-ml round bottom flask under a nitrogen atmosphere, and then an aqueous 2 M potassium carbonate solution (180 ml) was added thereto, tetrakis-(triphenylphosphine)palladium (1.01 g, 0.87 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 340 ml of ethyl acetate to prepare Compound 4 (14.58 g, 84%).

MS [M+H]$^+$=592

\<Preparation Example 5\> Preparation of Compound 5

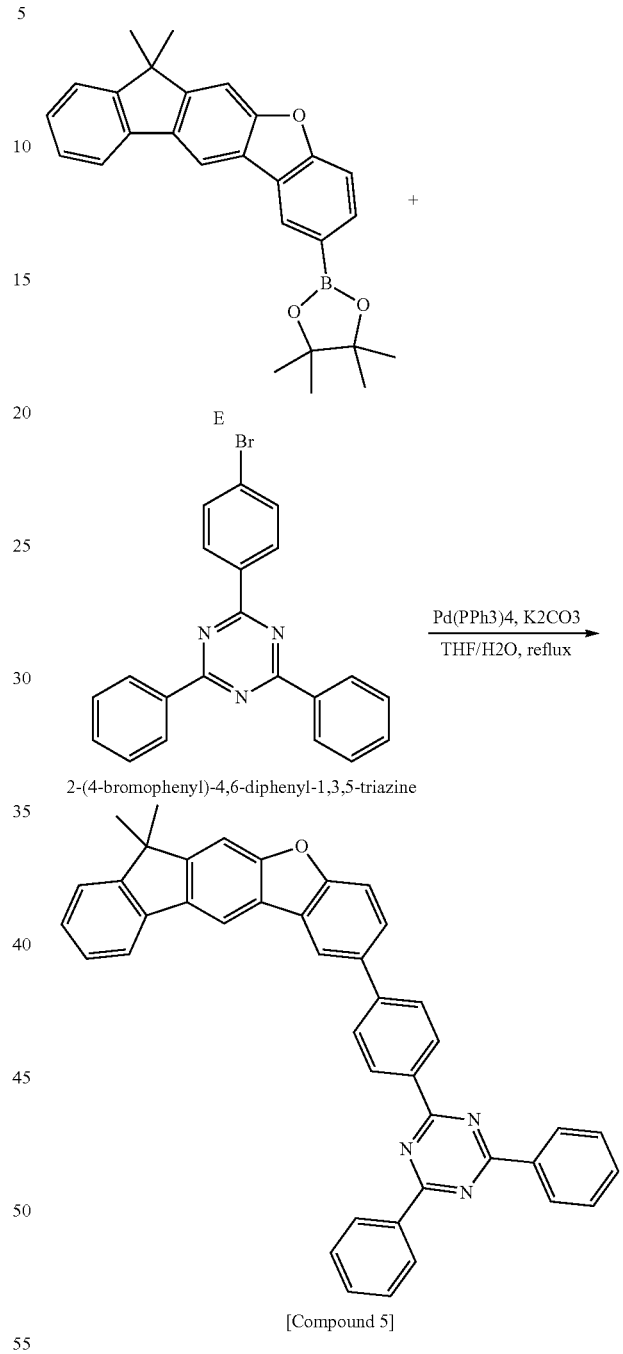

[Compound 5]

Compound E (10.06 g, 24.55 mmol) and 2-(4-bromophenyl)-4,6-diphenyl-1,3,5-triazine (10.0 g, 25.84 mmol) were completely dissolved in 400 ml of tetrahydrofuran in a 500-ml round bottom flask under a nitrogen atmosphere, and then an aqueous 2 M potassium carbonate solution (200 ml) was added thereto, tetrakis-(triphenylphosphine)palladium (0.91 g, 0.79 mmol) was put thereinto, and then the resulting mixture was heated and stirred for 6 hours. The temperature was lowered to room temperature, the aqueous layer was removed, and the residue was dried over anhydrous magnesium sulfate, and then concentrated under reduced pressure, and recrystallized with 190 ml of tetrahydrofuran to prepare Compound 5 (13.47 g, 87%).

MS [M+H]⁺=592

<Preparation Example 6> Preparation of Compound 6

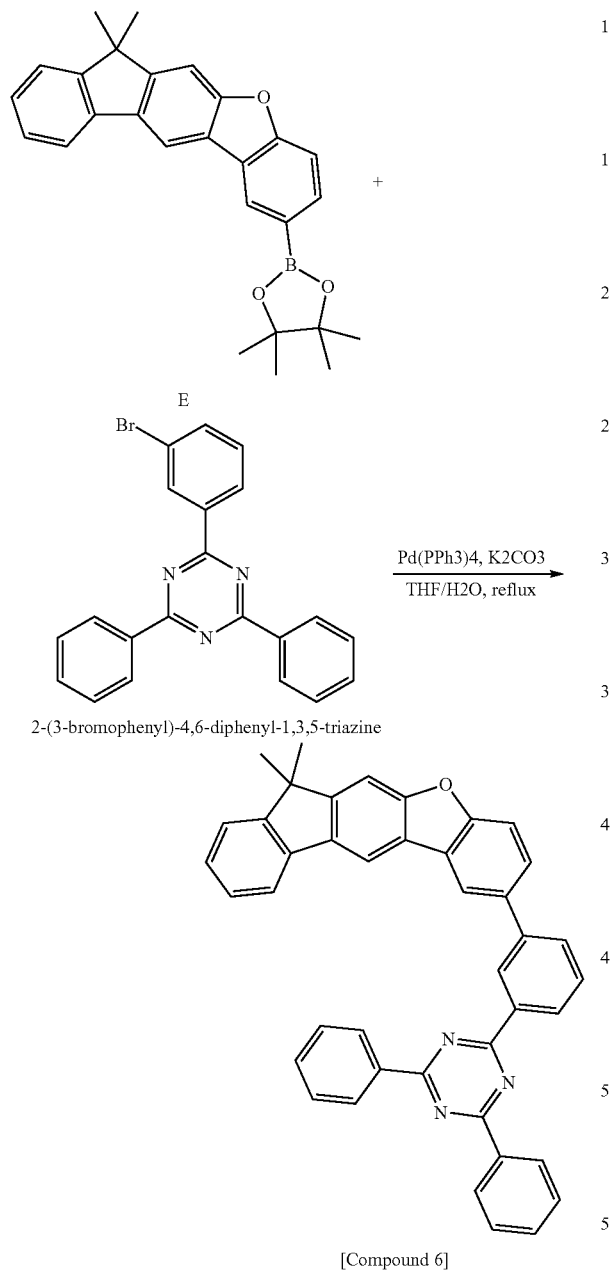

[Compound 6]

Compound E (10.06 g, 24.55 mmol) and 2-(3-bromophenyl)-4,6-diphenyl-1,3,5-triazine (10.0 g, 25.84 mmol) were completely dissolved in 400 ml of tetrahydrofuran in a 500-ml round bottom flask under a nitrogen atmosphere, and then an aqueous 2 M potassium carbonate solution (200 ml) was added thereto, tetrakis-(triphenylphosphine)palladium (0.91 g, 0.79 mmol) was put thereinto, and then the resulting mixture was heated and stirred for 6 hours. The temperature was lowered to room temperature, the aqueous layer was removed, and the residue was dried over anhydrous magnesium sulfate, and then concentrated under reduced pressure, and recrystallized with 190 ml of tetrahydrofuran to prepare Compound 6 (11.08 g, 72%).

MS [M+H]⁺=592

<Preparation Example 7> Preparation of Compound 7

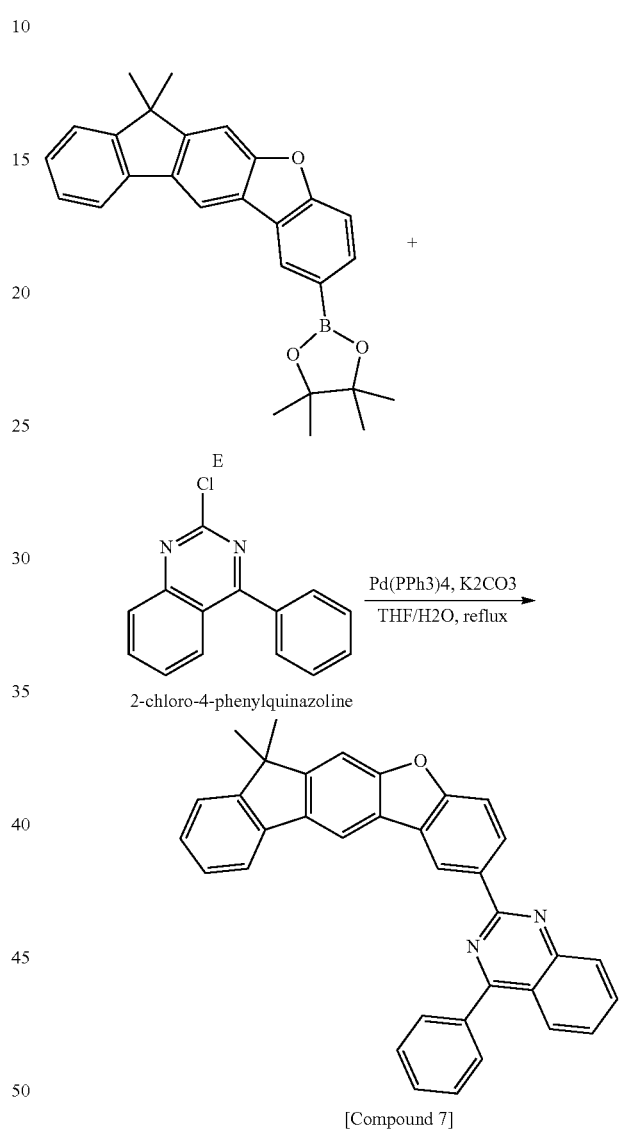

[Compound 7]

Compound E (16.23 g, 39.58 mmol) and 2-chloro-4-phenylquinazoline (10.0 g, 41.67 mmol) were completely dissolved in 220 ml of tetrahydrofuran in a 500-ml round bottom flask under a nitrogen atmosphere, and then an aqueous 2 M potassium carbonate solution (110 ml) was added thereto, tetrakis-(triphenylphosphine)palladium (0.96 g, 0.83 mmol) was put thereinto, and then the resulting mixture was heated and stirred for 2 hours. The temperature was lowered to room temperature, the aqueous layer was removed, and the residue was dried over anhydrous magnesium sulfate, and then concentrated under reduced pressure, and recrystallized with 230 ml of tetrahydrofuran to prepare Compound 7 (21.45 g, 67%).

MS[M+H]⁺=489

<Preparation Example 8> Preparation of Compound 8

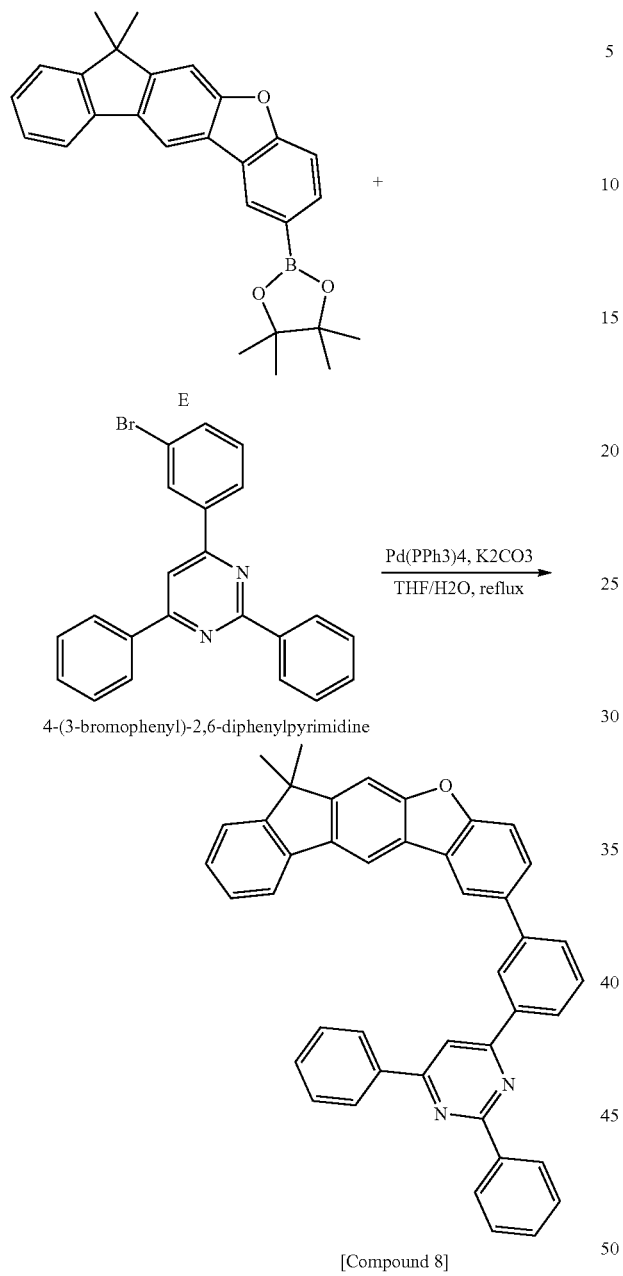

[Compound 8]

<Preparation Example 9> Preparation of Compound 9

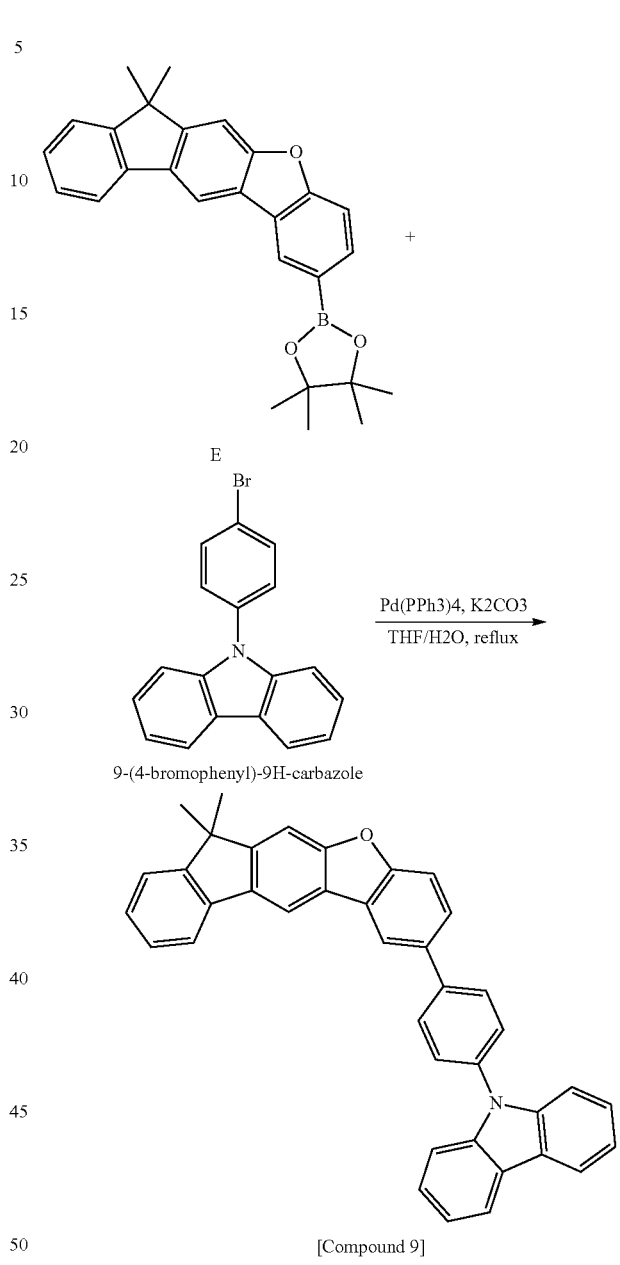

[Compound 9]

Compound E (10.06 g, 24.55 mmol) and 4-(3-bromophenyl)-2,6-diphenylpyrimidine (10.0 g, 25.84 mmol) were completely dissolved in 400 ml of tetrahydrofuran in a 500-ml round bottom flask under a nitrogen atmosphere, and then an aqueous 2 M potassium carbonate solution (200 ml) was added thereto, tetrakis-(triphenylphosphine) palladium (0.91 g, 0.79 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 120 ml of tetrahydrofuran to prepare Compound 8 (9.75 g, 65%).

MS[M+H]$^+$=591

Compound E (12.13 g, 29.60 mmol) and 9-(4-bromophenyl)-9H-carbazole (10.0 g, 31.15 mmol) were completely dissolved in 300 ml of tetrahydrofuran in a 500-ml round bottom flask under a nitrogen atmosphere, and then an aqueous 2 M potassium carbonate solution (150 ml) was added thereto, tetrakis-(triphenylphosphine)palladium (0.72 g, 0.62 mmol) was put thereinto, and then the resulting mixture was heated and stirred for 2 hours. The temperature was lowered to room temperature, the aqueous layer was removed, and the residue was dried over anhydrous magnesium sulfate, and then concentrated under reduced pressure, and recrystallized with 220 ml of ethyl acetate to prepare Compound 9 (12.11 g, 74%).

MS[M+H]$^+$=526

<Preparation Example 10> Preparation of Compound 10

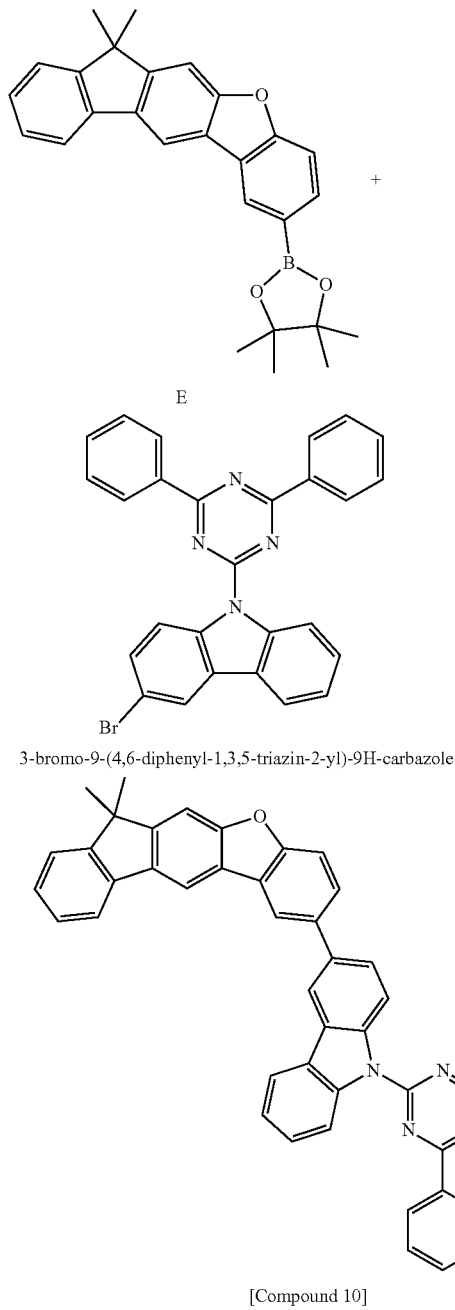

[Compound 10]

Compound E (8.18 g, 19.96 mmol) and 3-bromo-9-(4,6-diphenyl-1,3,5-triazin-2-yl)-9H-carbazole (10.0 g, 21.01 mmol) were completely dissolved in 480 ml of tetrahydrofuran in a 500-ml round bottom flask under a nitrogen atmosphere, and then an aqueous 2 M potassium carbonate solution (240 ml) was added thereto, tetrakis-(triphenylphosphine)palladium (0.49 g, 0.42 mmol) was put thereinto, and then the resulting mixture was heated and stirred for 9 hours. The temperature was lowered to room temperature, the aqueous layer was removed, and the residue was dried over anhydrous magnesium sulfate, and then concentrated under reduced pressure, and recrystallized with 310 ml of tetrahydrofuran to prepare Compound 10 (10.39 g, 73%).

MS[M+H]$^+$=681

<Preparation Example 11> Preparation of Compound 11

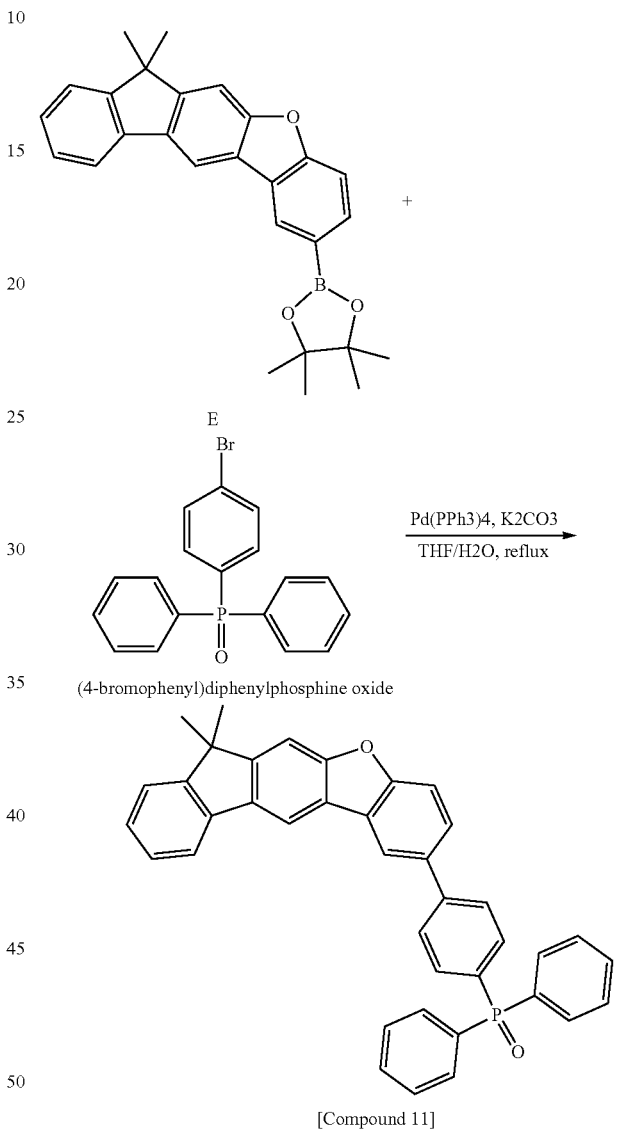

[Compound 11]

Compound E (10.94 g, 26.69 mmol) and (4-bromophenyl)diphenylphosphine oxide (10.0 g, 28.09 mmol) were completely dissolved in 300 ml of tetrahydrofuran in a 500-ml round bottom flask under a nitrogen atmosphere, and then an aqueous 2 M potassium carbonate solution (150 ml) was added thereto, tetrakis-(triphenylphosphine) palladium (0.72 g, 0.62 mmol) was put thereinto, and then the resulting mixture was heated and stirred for 2 hours. The temperature was lowered to room temperature, the aqueous layer was removed, and the residue was dried over anhydrous magnesium sulfate, and then concentrated under reduced pressure, and recrystallized with 220 ml of ethyl acetate to prepare Compound 11 (12.11 g, 74%).

MS[M+H]$^+$=561

<Preparation Example 12> Preparation of Compound 12

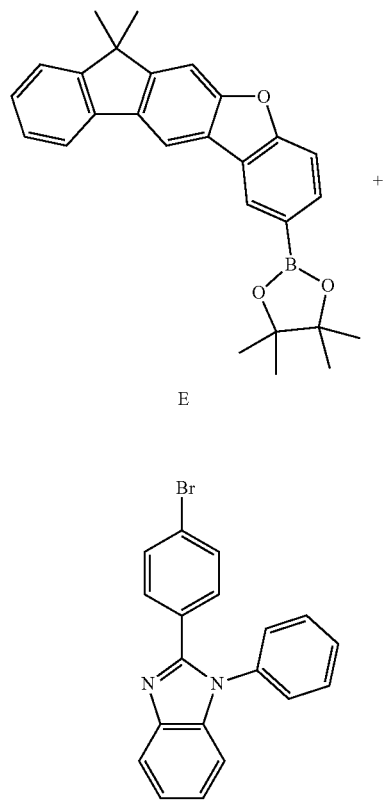

E 2-(4-bromophenyl)-1-phenyl-1H-benzo[d]imidazole

Pd(PPh3)4, K2CO3
———————→
THF/H2O, reflux

[Compound 12]

Compound E (11.19 g, 27.30 mmol) and 2-(4-bromophenyl)-1-phenyl-1H-benzo[d]imidazole (10.0 g, 28.74 mmol) were completely dissolved in 260 ml of tetrahydrofuran in a 500-ml round bottom flask under a nitrogen atmosphere, and then an aqueous 2 M potassium carbonate solution (130 ml) was added thereto, tetrakis-(triphenylphosphine)palladium (0.66 g, 0.57 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 260 ml of ethyl acetate to prepare Compound 12 (8.95 g, 56%).

MS[M+H]$^+$=553

<Preparation Examples 13 to 18> Preparation of Compounds 13 to 18

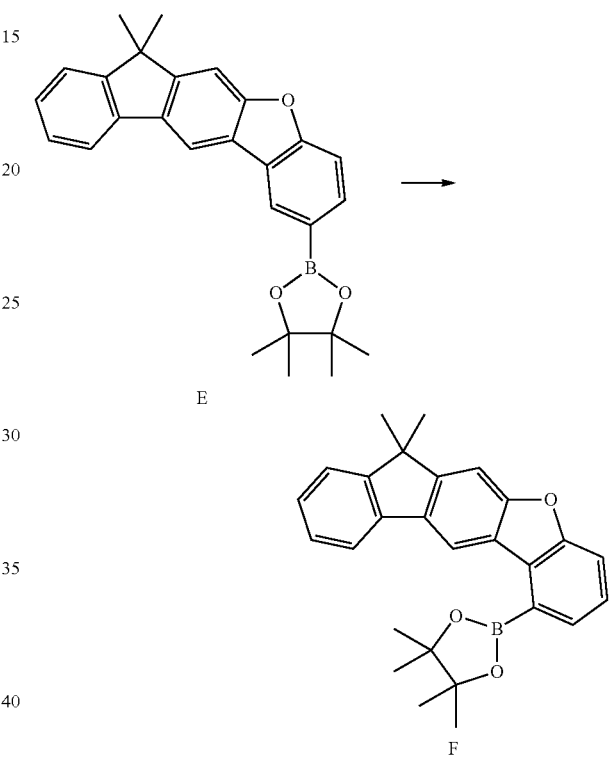

E

F

The following Compounds 13 to 18 were prepared in the same manner as in Preparation Examples 3 to 8, except that Compound F was used instead of Compound E as a starting material.

13

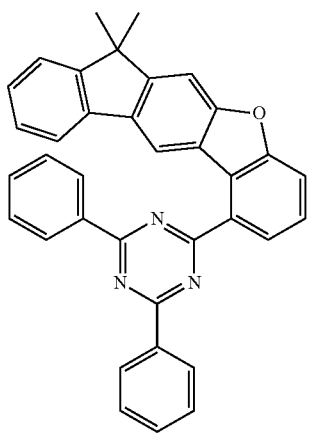

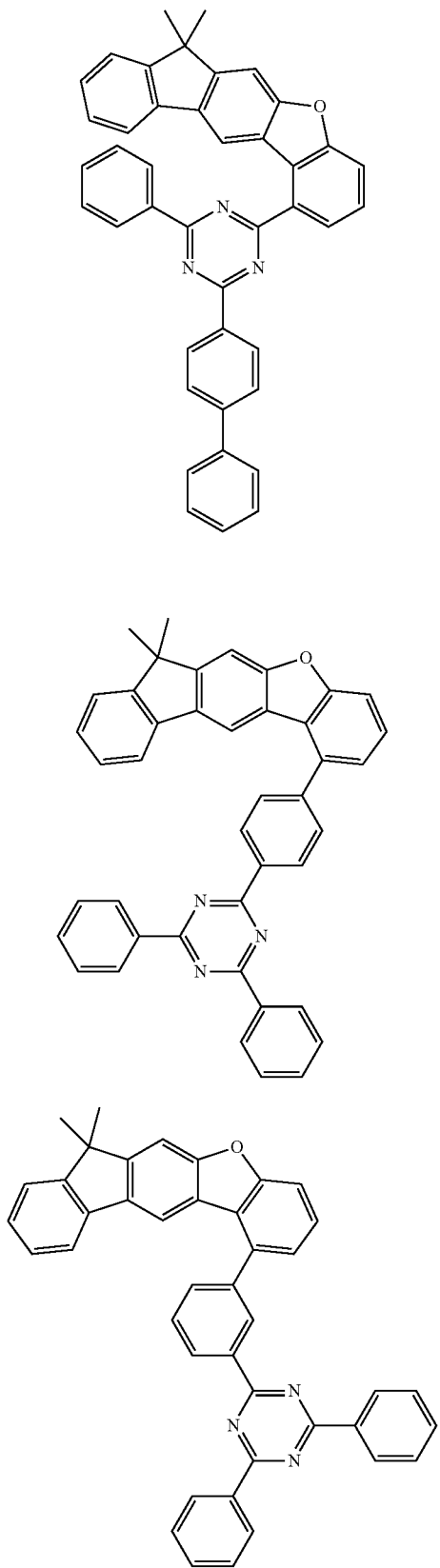
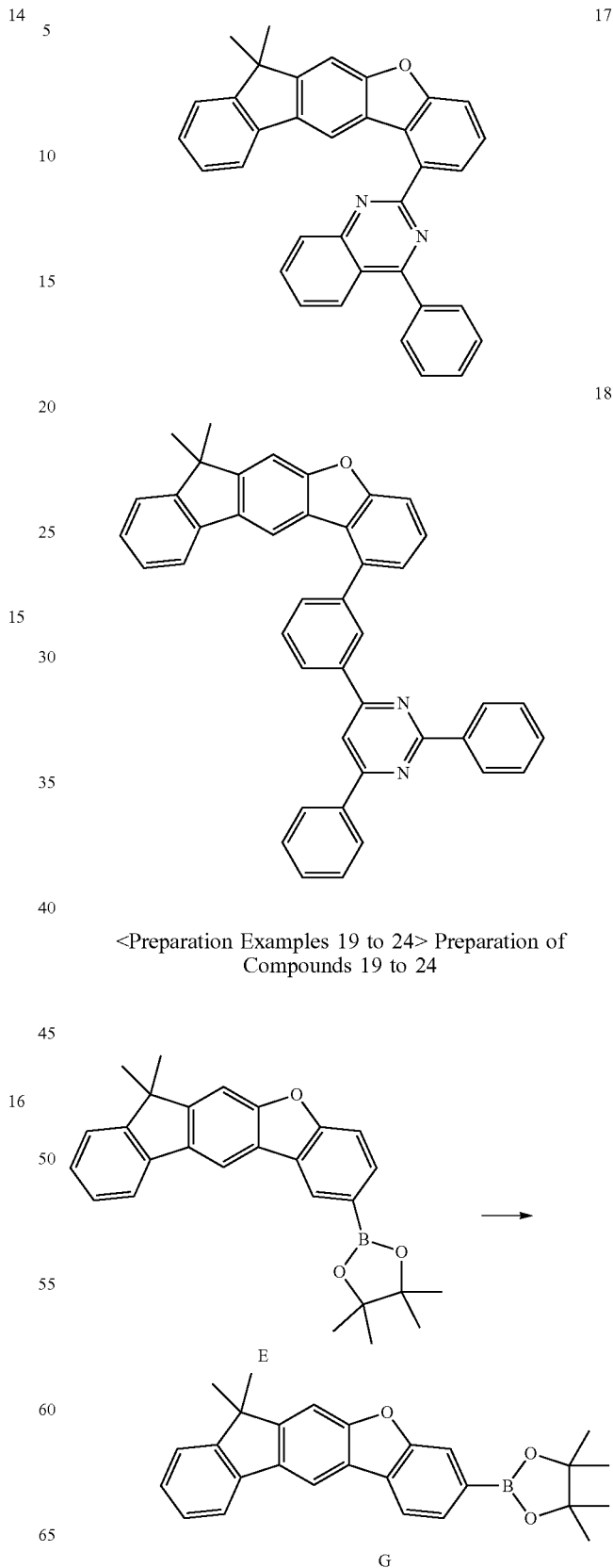
<Preparation Examples 19 to 24> Preparation of Compounds 19 to 24

The following Compounds 19 to 24 were prepared in the same manner as in Preparation Examples 3 to 8, except that Compound G was used instead of Compound E as a starting material.

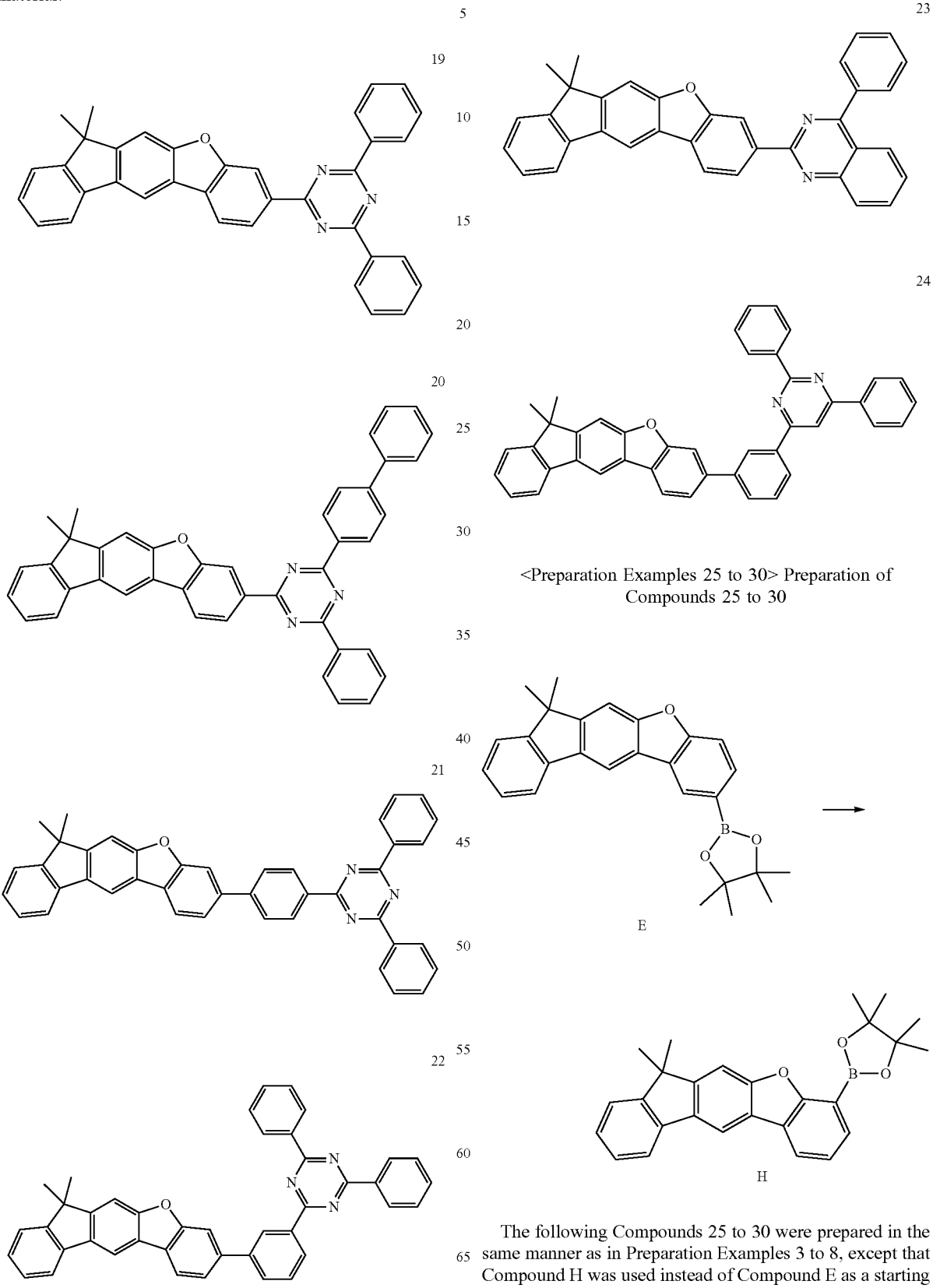

<Preparation Examples 25 to 30> Preparation of Compounds 25 to 30

The following Compounds 25 to 30 were prepared in the same manner as in Preparation Examples 3 to 8, except that Compound H was used instead of Compound E as a starting material.

25
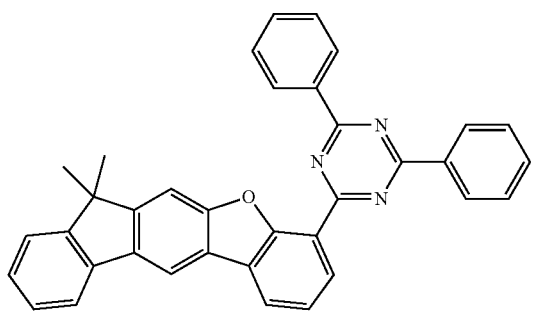
26
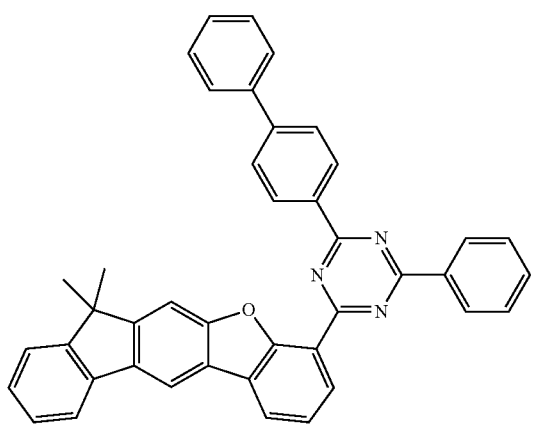
27
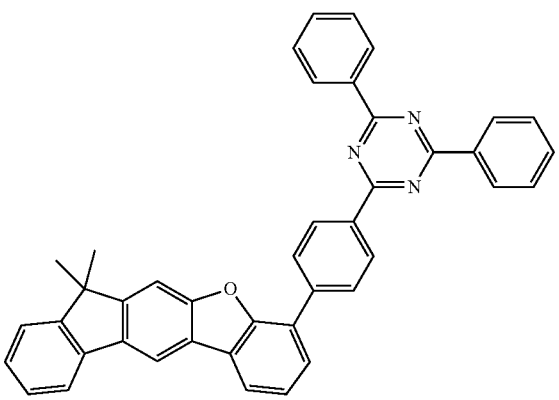
28
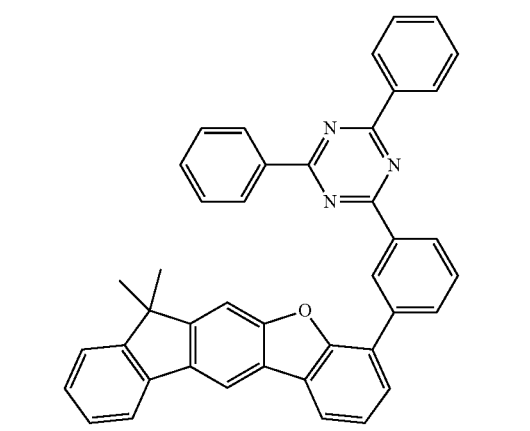
29
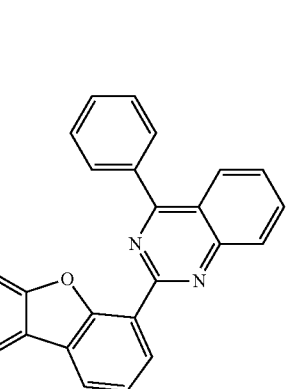
30
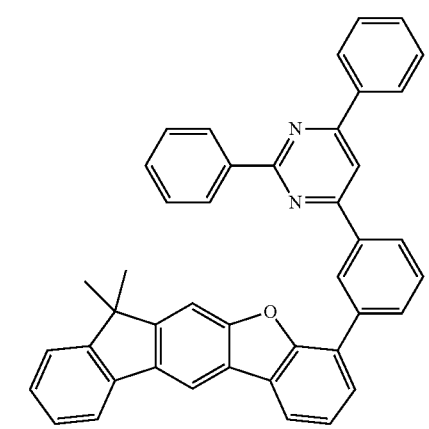
<Preparation Example 31> Preparation of Compound 31
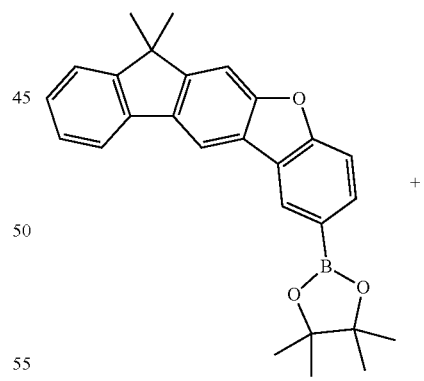
2-chloro-4,6-diphenypyridine

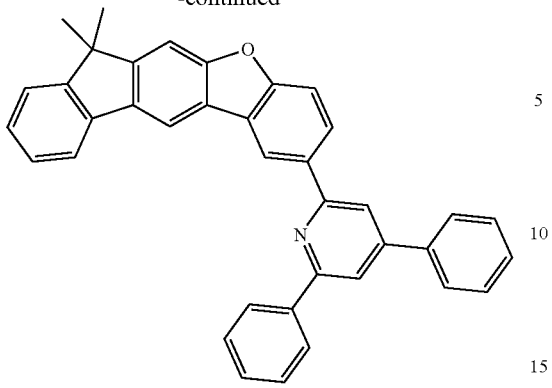

Compound E (14.59 g, 35.58 mmol) and 2-chloro-4,6-diphenylpyridine (10.0 g, 37.42 mmol) were completely dissolved in 320 ml of tetrahydrofuran in a 500-ml round bottom flask under a nitrogen atmosphere, and then an aqueous 2 M potassium carbonate solution (160 ml) was added thereto, tetrakis-(triphenylphosphine)palladium (0.87 g, 0.75 mmol) was put thereinto, and then the resulting mixture was heated and stirred for 3 hours. The temperature was lowered to room temperature, the aqueous layer was removed, and the residue was dried over anhydrous magnesium sulfate, and then concentrated under reduced pressure, and recrystallized with 250 ml of ethyl acetate to prepare Compound 31 (17.49 g, 74%).

MS[M+H]$^+$=514

<Preparation Example 32> Preparation of Compound 32

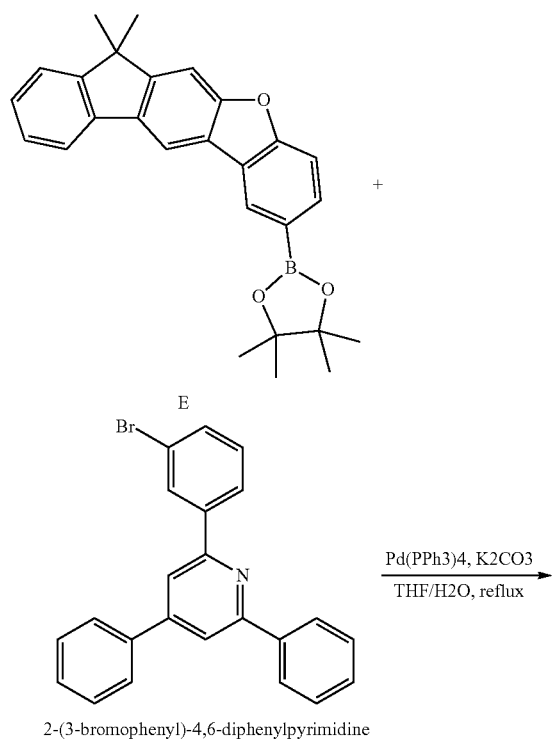

2-(3-bromophenyl)-4,6-diphenylpyrimidine

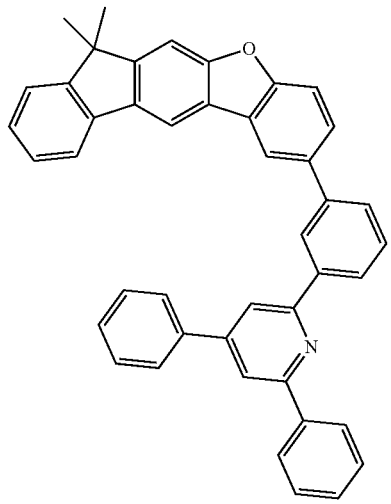

Compound E (10.06 g, 24.55 mmol) and 2-(3-bromophenyl)-4,6-diphenylpyridine (10.0 g, 25.83 mmol) were completely dissolved in 300 ml of tetrahydrofuran in a 500-ml round bottom flask under a nitrogen atmosphere, and then an aqueous 2 M potassium carbonate solution (150 ml) was added thereto, tetrakis-(triphenylphosphine)palladium (0.91 g, 0.79 mmol) was put thereinto, and then the resulting mixture was heated and stirred for 6 hours. The temperature was lowered to room temperature, the aqueous layer was removed, and the residue was dried over anhydrous magnesium sulfate, and then concentrated under reduced pressure, and recrystallized with 160 ml of tetrahydrofuran to prepare Compound 32 (8.78 g, 58%).

MS[M+H]$^+$=590

Experimental Example 1-1

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

Hexanitrile hexaazatriphenylene (HAT) of the following Chemical Formula was thermally vacuum deposited to have a thickness of 500 Å on the thus prepared ITO transparent electrode, thereby forming a hole injection layer.

[HAT]

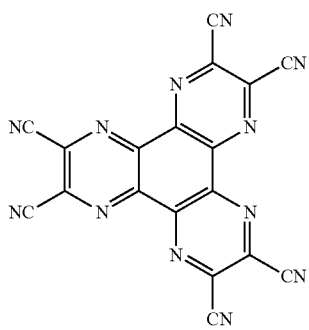

[BH]

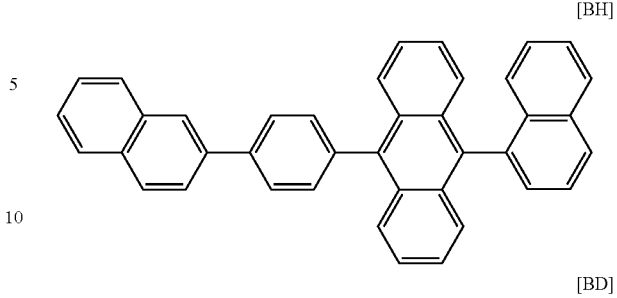

The following compound 4-4'-bis[N-(1-naphthyl)-N-phenylamino]biphenyl (NPB) (300 Å), which is a material for transporting holes, was vacuum deposited on the hole injection layer, thereby forming a hole transporting layer.

[BD]

[NPB]

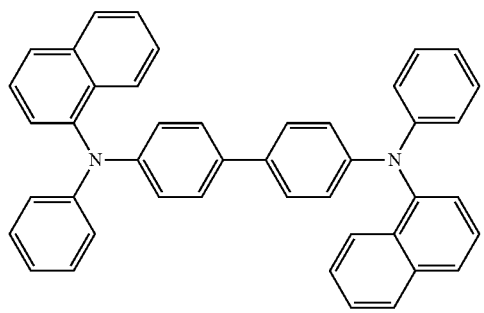

[ET1]

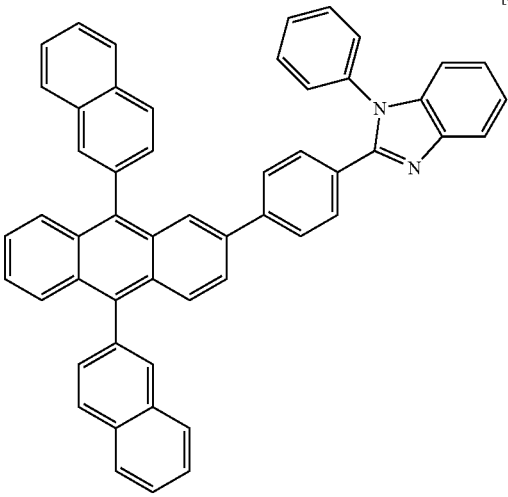

Subsequently, the following Compound 1 was vacuum deposited to have a film thickness of 100 Å on the hole transporting layer, thereby forming an electron blocking layer.

[Compound 1]

[LiQ]

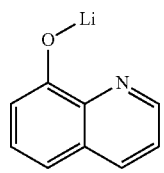

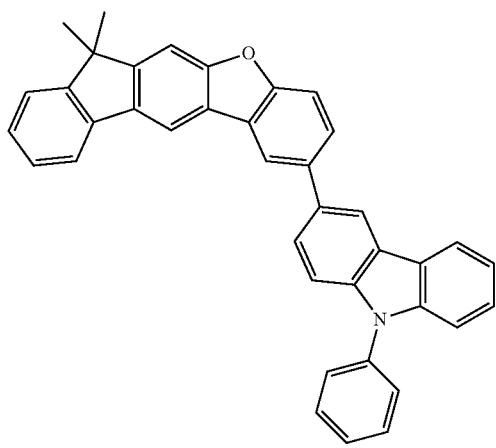

Compound ET1 and Compound LiQ (lithium quinolate) were vacuum deposited at a weight ratio of 1:1 on the light emitting layer, thereby forming an electron injection and transporting layer having a thickness of 300 Å. Lithium fluoride (LiF) and aluminum were sequentially deposited on the electron injection and transporting layer to have a thickness of 12 Å and 2,000 Å, respectively, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

Subsequently, the following BH and BD were vacuum deposited at a weight ratio of 25:1 to have a film thickness of 300 Å on the electron blocking layer, thereby forming a light emitting layer.

Experimental Example 1-2

An organic light emitting device was manufactured in the same manner as in Experimental Example 1-1, except that Compound 2 was used instead of Compound 1 in Experimental Example 1-1.

Comparative Example 1-1

An organic light emitting device was manufactured in the same manner as in Experimental Example 1-1, except that a compound of the following EB1 was used instead of Compound 1 in Experimental Example 1-1.

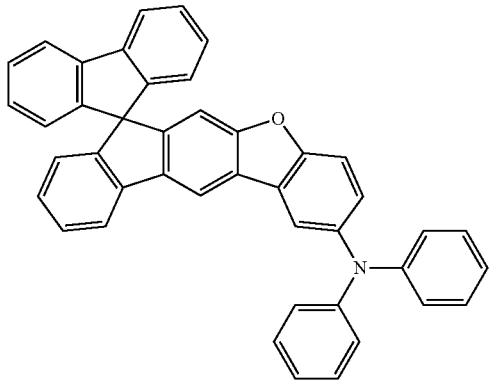

[EB1]

Comparative Example 1-2

An organic light emitting device was manufactured in the same manner as in Experimental Example 1-1, except that a compound of the following EB2 was used instead of Compound 1 in Experimental Example 1-1.

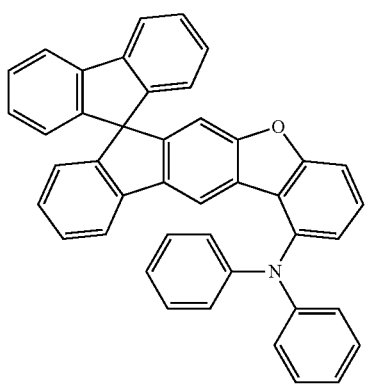

[EB2]

When current was applied to the organic light emitting devices manufactured in Experimental Examples 1-1 and 1-2 and Comparative Examples 1-1 and 1-2, the results of Table 1 were obtained.

TABLE 1

| | Compound (Electron blocking layer) | Voltage (V@10 mA/cm$^2$) | Efficiency (cd/A@10 mA/cm$^2$) | Color coordinate (x, y) |
|---|---|---|---|---|
| Experimental Example 1-1 | Compound 1 | 3.75 | 6.47 | (0.137, 0.126) |
| Experimental Example 1-2 | Compound 2 | 3.86 | 6.35 | (0.137, 0.127) |
| Comparative Example 1-1 | EB1 | 4.15 | 5.86 | (0.136, 0.127) |
| Comparative Example 1-2 | EB2 | 4.37 | 5.62 | (0.136, 0.127) |

As seen in Table 1, the organic light emitting device manufactured by using the compound of the present invention as an electron blocking layer exhibits excellent characteristics in terms of efficiency, driving voltage, and/or stability of the organic light emitting device.

The organic light emitting device manufactured by using the compound of the present invention as an electron blocking layer exhibits lower voltage and higher efficiency characteristics than the organic light emitting devices manufactured by using the compounds in Comparative Examples 1-11 and 1-2, in which a ring is formed to have a structure similar to the core of the hetero-cyclic compound of Chemical Formula 1 according to an exemplary embodiment of the present specification, as an electron blocking layer. As in the result in Table 1, it could be confirmed that the compound according to the present invention has an excellent hole blocking capability and thus can be applied to an organic light emitting device.

Comparative Example 2-1

The compounds prepared in the Preparation Examples were subjected to high-purity sublimation purification by a typically known method, and then a green organic light emitting device was manufactured by the following method.

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

An organic light emitting device was manufactured by configuring the light emitting device in the order of m-MTDATA (60 nm)/TCTA (80 nm)/CBP+10% Ir(ppy)$_3$ (300 nm)/BCP (10 nm)/Alq$_3$ (30 nm)/LiF (1 nm)/Al (200 nm) on the thus prepared ITO transparent electrode by using CBP as a host.

The structures of m-MTDATA, TCTA, Ir(ppy)₃, CBP, and BCP are as follows.

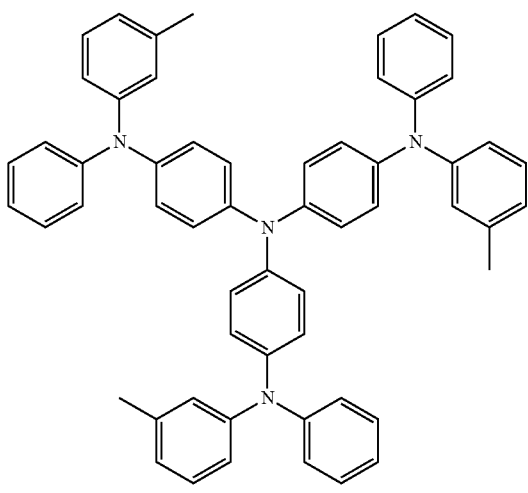

m-MTDATA

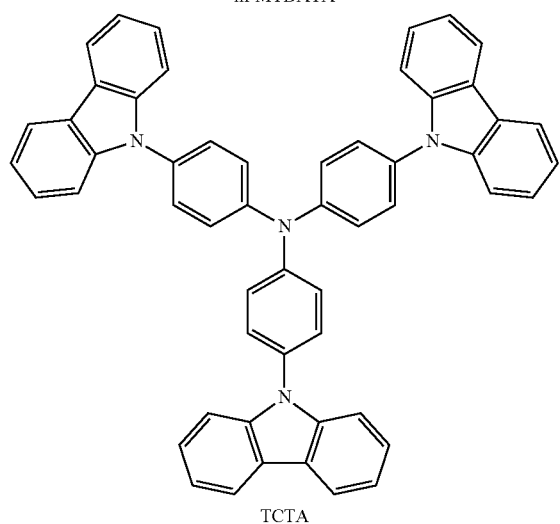

TCTA

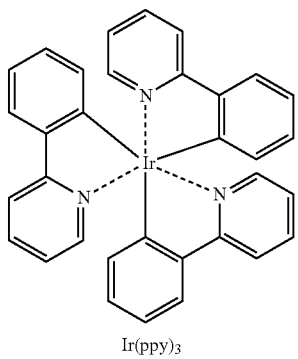

Ir(ppy)₃

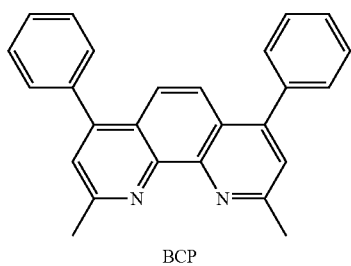

BCP

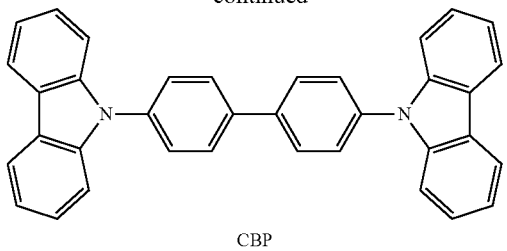

CBP

Experimental Example 2-1

An organic light emitting device was manufactured in the same manner as in Comparative Example 2-1, except that Compound 3 was used instead of CBP in Comparative Example 2-1.

Experimental Example 2-2

An organic light emitting device was manufactured in the same manner as in Comparative Example 2-1, except that Compound 4 was used instead of Compound CBP in Comparative Example 2-1.

Experimental Example 2-3

An organic light emitting device was manufactured in the same manner as in Comparative Example 2-1, except that Compound 5 was used instead of Compound CBP in Comparative Example 2-1.

Experimental Example 2-4

An organic light emitting device was manufactured in the same manner as in Comparative Example 2-1, except that Compound 6 was used instead of Compound CBP in Comparative Example 2-1.

Experimental Example 2-5

An organic light emitting device was manufactured in the same manner as in Comparative Example 2-1, except that Compound 7 was used instead of Compound CBP in Comparative Example 2-1.

Experimental Example 2-6

An organic light emitting device was manufactured in the same manner as in Comparative Example 2-1, except that Compound 8 was used instead of Compound CBP in Comparative Example 2-1.

Experimental Example 2-7

An organic light emitting device was manufactured in the same manner as in Comparative Example 2-1, except that Compound 14 was used instead of Compound CBP in Comparative Example 2-1.

Experimental Example 2-8

An organic light emitting device was manufactured in the same manner as in Comparative Example 2-1, except that Compound 16 was used instead of Compound CBP in Comparative Example 2-1.

Experimental Example 2-9

An organic light emitting device was manufactured in the same manner as in Comparative Example 2-1, except that Compound 20 was used instead of Compound CBP in Comparative Example 2-1.

Experimental Example 2-10

An organic light emitting device was manufactured in the same manner as in Comparative Example 2-1, except that Compound 22 was used instead of Compound CBP in Comparative Example 2-1.

Experimental Example 2-11

An organic light emitting device was manufactured in the same manner as in Comparative Example 2-1, except that Compound 26 was used instead of Compound CBP in Comparative Example 2-1.

Experimental Example 2-12

An organic light emitting device was manufactured in the same manner as in Comparative Example 2-1, except that Compound 28 was used instead of Compound CBP in Comparative Example 2-1.

Experimental Example 2-13

An organic light emitting device was manufactured in the same manner as in Comparative Example 2-1, except that Compound 31 was used instead of Compound CBP in Comparative Example 2-1.

Experimental Example 2-14

An organic light emitting device was manufactured in the same manner as in Comparative Example 2-1, except that Compound 32 was used instead of Compound CBP in Comparative Example 2-1.

Comparative Example 2-2

An organic light emitting device was manufactured in the same manner as in Comparative Example 2-1, except that a compound of the following GH 1 was used instead of Compound CBP in Comparative Example 2-1.

[GH 1]

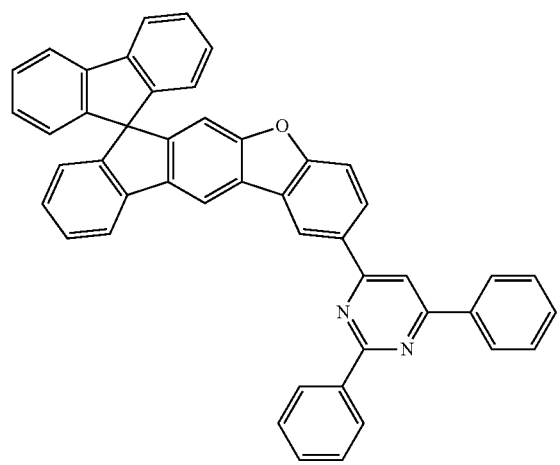

Comparative Example 2-3

An organic light emitting device was manufactured in the same manner as in Comparative Example 2-1, except that a compound of the following GH 2 was used instead of Compound CBP in Comparative Example 2-1.

[GH 2]

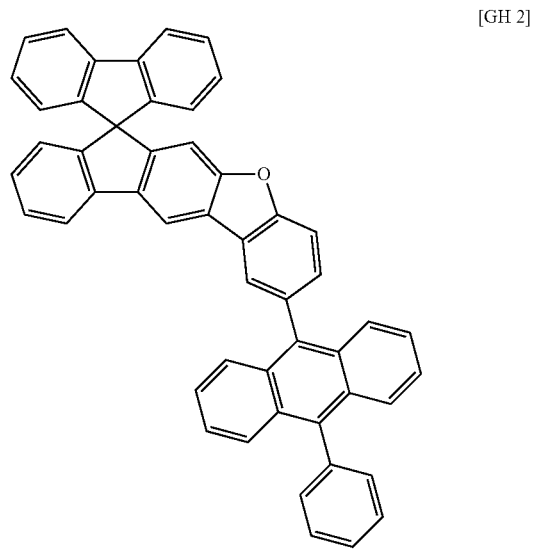 [SMILES: c1ccc(-c2c3ccccc3c(-c3ccc4oc5cc6c(cc5c4c3)-c3ccccc3C63c4ccccc4-c4ccccc43)c3ccccc23)cc1]

When current was applied to the organic light emitting devices manufactured in Experimental Examples 2-1 to 2-14 and Comparative Examples 2-1 to 2-3, the results of the following Table 2 were obtained.

TABLE 2

|  | Compound (Host) | Voltage (V@10 mA/cm$^2$) | Efficiency (cd/A@10 mA/cm$^2$) | EL peak (nm) |
| --- | --- | --- | --- | --- |
| Comparative Example 2-1 | CBP | 7.62 | 35.32 | 516 |
| Experimental Example 2-1 | Compound 3 | 6.70 | 44.73 | 517 |
| Experimental Example 2-2 | Compound 4 | 6.66 | 44.85 | 516 |
| Experimental Example 2-3 | Compound 5 | 6.71 | 44.72 | 517 |
| Experimental Example 2-4 | Compound 6 | 6.69 | 44.75 | 518 |
| Experimental Example 2-5 | Compound 7 | 6.85 | 44.31 | 517 |
| Experimental Example 2-6 | Compound 8 | 6.63 | 44.63 | 517 |
| Experimental Example 2-7 | Compound 14 | 6.64 | 44.60 | 516 |
| Experimental Example 2-8 | Compound 16 | 6.62 | 44.66 | 517 |
| Experimental Example 2-9 | Compound 20 | 6.68 | 44.558 | 517 |
| Experimental Example 2-10 | Compound 22 | 6.67 | 44.59 | 517 |
| Experimental Example 2-11 | Compound 26 | 6.66 | 44.60 | 517 |
| Experimental Example 2-12 | Compound 28 | 6.69 | 44.62 | 517 |
| Experimental Example 2-13 | Compound 31 | 6.57 | 44.98 | 517 |

TABLE 2-continued

|  | Compound (Host) | Voltage (V@10 mA/cm$^2$) | Efficiency (cd/A@10 mA/cm$^2$) | EL peak (nm) |
|---|---|---|---|---|
| Experimental Example 2-14 | Compound 32 | 6.62 | 44.34 | 517 |
| Comparative Example 2-2 | GH 1 | 7.25 | 39.52 | 517 |
| Comparative Example 2-3 | GH 2 | 7.56 | 37.41 | 516 |

As seen in Table 2, it could be confirmed that the green organic light emitting devices in Experimental Examples 2-1 to 2-14, in which the hetero-cyclic compound represented by Chemical Formula 1 according to an exemplary embodiment of the present specification was used as a host material of a light emitting layer, exhibited better performances in terms of current efficiency and driving voltage than the organic light emitting devices in Comparative Example 2-1, in which CBP in the related art was used, and Comparative Examples 2-2 and 2-3, in which a ring was formed to have a structure similar to the core of the present invention. In particular, it can be seen that the compounds having triazine and pyrimidine as the substituent are suitable for a green organic light emitting device.

Experimental Examples 3-1 to 3-4

The compounds prepared in the Preparation Examples were subjected to high-purity sublimation purification by a typically known method, and then red organic light emitting devices were manufactured by the following method.

An ITO glass was patterned and then washed, such that the light emitting area of the ITO glass became 2 mm×2 mm. The substrate was mounted into a vacuum chamber, and then the base pressure was allowed to be 1×10$^{-6}$ torr, and then for the organic material, DNTPD (700 Å), α-NPB (300 Å), and Compound 7, 17, 23, or 29 prepared by the present invention were used as a host (90 wt %) on the ITO, the following (piq)$_2$Ir(acac) (10 wt %) was co-deposited (300 Å) as a dopant, films were formed in the order of Alq$_3$ (350 Å), LiF (5 Å), and Al (1,000 Å), and measurements were made at 0.4 mA.

The structures of DNTPD, α-NPB, (piq)$_2$Ir(acac), and Alq$_3$ are as follows.

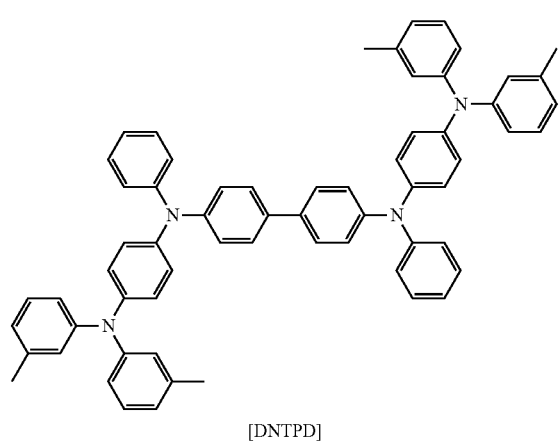

[DNTPD]

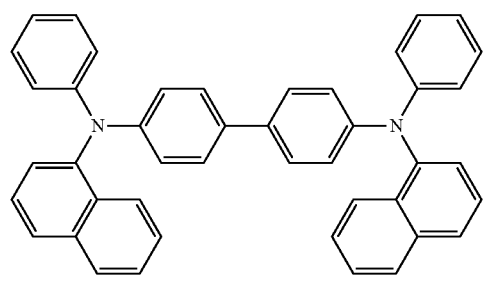

[α-NPB]

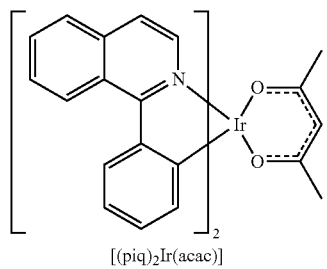

[(piq)$_2$Ir(acac)]

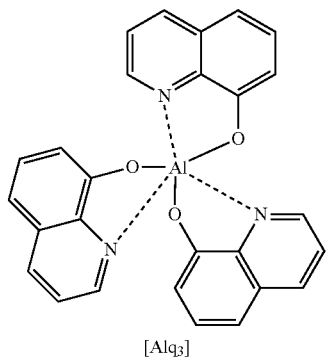

[Alq$_3$]

Comparative Example 3-1

An organic light emitting device was manufactured in the same manner as in Experimental Example 3-1, except that CBP was used instead of Compound 7 in Experimental Example 3-1.

For the organic light emitting devices manufactured by Experimental Examples 3-1 to 3-4 and Comparative Example 3-1, the voltages, current densities, luminances, color coordinates, and service lives were measured, and the results are shown in the following Table 3. T95 means the time taken for the luminance to be reduced to 95% of the initial luminance (5,000 nit).

TABLE 3

| Classification | Host | Dopant | Voltage (V) | Luminance (cd/m²) | CIEx, CIEy | T95 (hr) |
|---|---|---|---|---|---|---|
| Experimental Example 3-1 | Compound 7 | [(piq)2Ir(acac)] | 4.4 | 1860 | 0.673, 0.326 | 395 |
| Experimental Example 3-2 | Compound 17 | [(piq)2Ir(acac)] | 4.7 | 1780 | 0.674, 0.325 | 390 |
| Experimental Example 3-3 | Compound 23 | [(piq)2Ir(acac)] | 4.3 | 1910 | 0.673, 0.326 | 425 |
| Experimental Example 3-4 | Compound 29 | [(piq)2Ir(acac)] | 4.5 | 1840 | 0.674, 0.325 | 385 |
| Comparative Example 3-1 | CBP | [(piq)2Ir(acac)] | 5.7 | 1420 | 0.670, 0.331 | 350 |

As a result of the experiment, it could be confirmed that the red organic light emitting devices in Experimental Examples 3-1 to 3-4 according to an exemplary embodiment of the present specification exhibited better performances in terms of current efficiency, driving voltage, and service life than the red organic light emitting device in Comparative Example 3-1 in which Compound CBP in the related art was used. In particular, it can be seen that the compounds having triazine and quinazoline as the substituent are suitable for a red organic light emitting device.

Experimental Example 4-1

An experiment was performed in the same manner as in Experimental Example 1-1, except that as the electron transporting layer, Compound 3 was used instead of ET1.

Experimental Example 4-2

An experiment was performed in the same manner as in Experimental Example 1-1, except that as the electron transporting layer, Compound 4 was used instead of ET1.

Experimental Example 4-3

An experiment was performed in the same manner as in Experimental Example 1-1, except that as the electron transporting layer, Compound 5 was used instead of ET1.

Experimental Example 4-4

An experiment was performed in the same manner as in Experimental Example 1-1, except that as the electron transporting layer, Compound 6 was used instead of ET1.

Experimental Example 4-5

An experiment was performed in the same manner as in Experimental Example 1-1, except that as the electron transporting layer, Compound 8 was used instead of ET1.

Experimental Example 4-6

An experiment was performed in the same manner as in Experimental Example 1-1, except that as the electron transporting layer, Compound 13 was used instead of ET1.

Experimental Example 4-7

An experiment was performed in the same manner as in Experimental Example 1-1, except that as the electron transporting layer, Compound 14 was used instead of ET1.

Experimental Example 4-8

An experiment was performed in the same manner as in Experimental Example 1-1, except that as the electron transporting layer, Compound 15 was used instead of ET1.

Experimental Example 4-9

An experiment was performed in the same manner as in Experimental Example 1-1, except that as the electron transporting layer, Compound 16 was used instead of ET1.

Experimental Example 4-10

An experiment was performed in the same manner as in Experimental Example 1-1, except that as the electron transporting layer, Compound 18 was used instead of ET1.

Experimental Example 4-11

An experiment was performed in the same manner as in Experimental Example 1-1, except that as the electron transporting layer, Compound 19 was used instead of ET1.

Experimental Example 4-12

An experiment was performed in the same manner as in Experimental Example 1-1, except that as the electron transporting layer, Compound 20 was used instead of ET1.

Experimental Example 4-13

An experiment was performed in the same manner as in Experimental Example 1-1, except that as the electron transporting layer, Compound 21 was used instead of ET1.

Experimental Example 4-14

An experiment was performed in the same manner as in Experimental Example 1-1, except that as the electron transporting layer, Compound 22 was used instead of ET1.

Experimental Example 4-15

An experiment was performed in the same manner as in Experimental Example 1-1, except that as the electron transporting layer, Compound 25 was used instead of ET1.

Experimental Example 4-16

An experiment was performed in the same manner as in Experimental Example 1-1, except that as the electron transporting layer, Compound 26 was used instead of ET1.

Experimental Example 4-17

An experiment was performed in the same manner as in Experimental Example 1-1, except that as the electron transporting layer, Compound 27 was used instead of ET1.

Experimental Example 4-18

An experiment was performed in the same manner as in Experimental Example 1-1, except that as the electron transporting layer, Compound 28 was used instead of ET1.

Comparative Example 4-1

An organic light emitting device was manufactured in the same manner as in Experimental Example 4-1, except that as the electron transporting layer, a compound of the following ET2 was used instead of Compound 3.

[ET2]

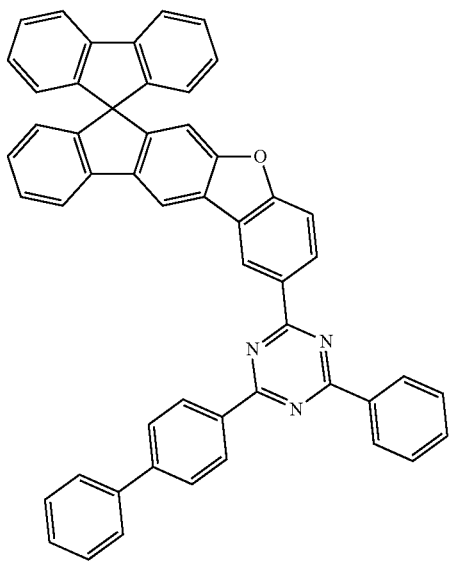

Comparative Example 4-2

An organic light emitting device was manufactured in the same manner as in Experimental Example 4-1, except that as the electron transporting layer, a compound of the following ET3 was used instead of Compound 3.

[ET3]

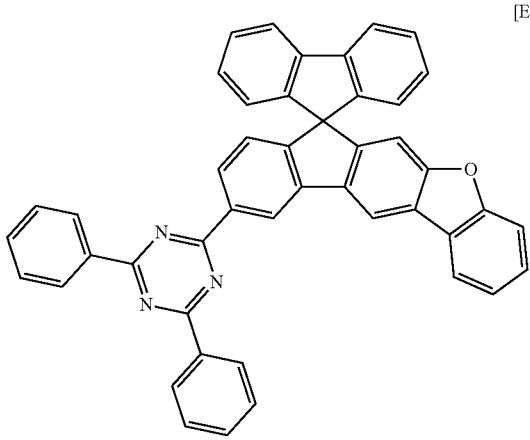

When current was applied to the organic light emitting devices manufactured in Experimental Examples 4-1 to 4-18 and Comparative Examples 4-1 and 4-2, the results of the following Table 4 were obtained.

TABLE 4

| | Compound | Voltage (V@10 mA/cm$^2$) | Efficiency (cd/A@10 mA/cm$^2$) | Color coordinate (x, y) |
|---|---|---|---|---|
| Experimental Example 4-1 | Compound 3 | 3.78 | 4.91 | (0.138, 0.126) |
| Experimental Example 4-2 | Compound 4 | 3.55 | 4.95 | (0.139, 0.127) |
| Experimental Example 4-3 | Compound 5 | 3.66 | 4.85 | (0.138, 0.126) |
| Experimental Example 4-4 | Compound 6 | 3.65 | 4.82 | (0.138, 0.127) |
| Experimental Example 4-5 | Compound 8 | 3.69 | 4.65 | (0.137, 0.129) |
| Experimental Example 4-6 | Compound 13 | 3.75 | 4.64 | (0.138, 0.128) |
| Experimental Example 4-7 | Compound 14 | 3.70 | 4.72 | (0.138, 0.129) |
| Experimental Example 4-8 | Compound 15 | 3.76 | 4.65 | (0.136, 0.128) |
| Experimental Example 4-9 | Compound 16 | 3.78 | 4.69 | (0.137, 0.127) |
| Experimental Example 4-10 | Compound 18 | 3.75 | 4.65 | (0.137, 0.127) |
| Experimental Example 4-11 | Compound 19 | 3.79 | 4.66 | (0.138, 0.127) |
| Experimental Example 4-12 | Compound 20 | 3.77 | 4.67 | (0.137, 0.126) |
| Experimental Example 4-13 | Compound 21 | 3.73 | 4.52 | (0.137, 0.128) |
| Experimental Example 4-14 | Compound 22 | 3.78 | 4.71 | (0.137, 0.127) |
| Experimental Example 4-15 | Compound 25 | 3.77 | 4.73 | (0.137, 0.128) |
| Experimental Example 4-16 | Compound 26 | 3.76 | 4.72 | (0.138, 0.127) |
| Experimental Example 4-17 | Compound 27 | 3.75 | 4.70 | (0.137, 0.127) |
| Experimental Example 4-18 | Compound 28 | 3.79 | 4.72 | (0.137, 0.127) |
| Comparative Example 4-1 | ET2 | 4.15 | 4.25 | (0.136, 0.130) |
| Comparative Example 4-2 | ET3 | 4.37 | 4.07 | (0.136, 0.129) |

As a result of the experiment, it could be confirmed that the organic light emitting devices in Experimental Examples 4-1 to 4-18 according to an exemplary embodiment of the present specification exhibited better performances in terms of current efficiency and driving voltage than the organic light emitting devices in Comparative Examples 4-1 and 4-2, in which a ring is formed to have a structure similar to the core of the present invention.

Comparative Example 5

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

Hexanitrile hexaazatriphenylene (HAT) of the following Chemical Formula was thermally vacuum deposited to have a thickness of 500 Å on the thus prepared ITO transparent electrode, thereby forming a hole injection layer.

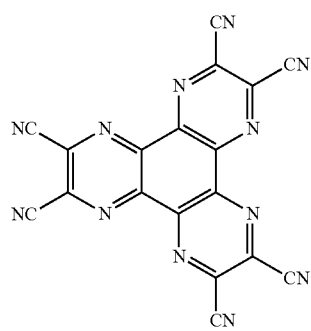
[HAT]

The following compound N4,N4,N4',N4'-tetra([1,1'-biphenyl]-4-yl)-[1,1'-biphenyl]-4,4'-diamine (300 Å) being a material for transporting holes was vacuum deposited on the hole injection layer, thereby forming a hole transporting layer.

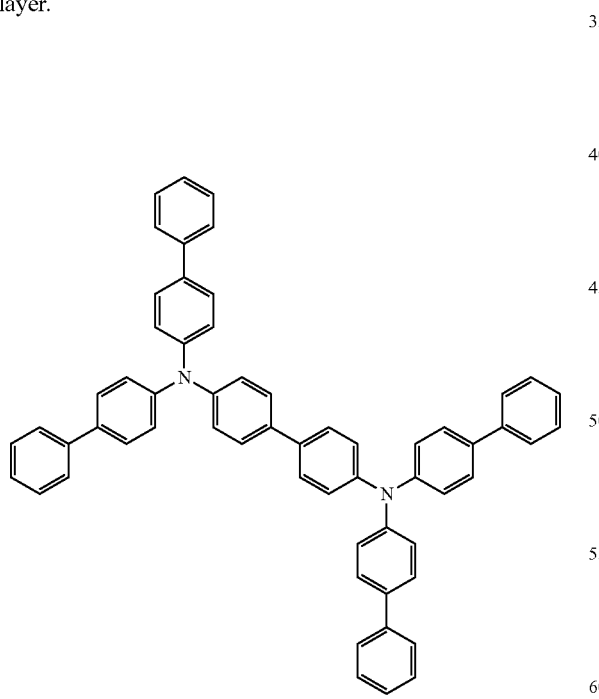

Subsequently, the following compound N,N-di([1,1'-biphenyl]-4-yl)-4'-(9H-carbazol-9-yl)-[1,1'-biphenyl]-4-amine was vacuum deposited to have a film thickness of 100 Å on the hole transporting layer, thereby forming an electron blocking layer.

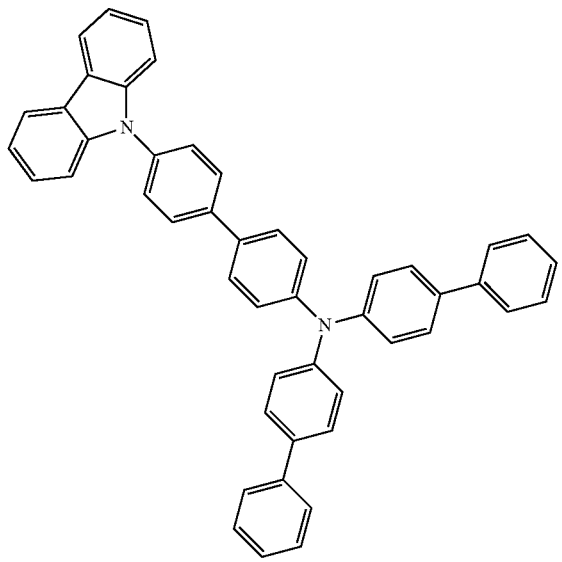
[EBL]

Subsequently, the following BH and BD were vacuum deposited at a weight ratio of 25:1 to have a film thickness of 300 Å on the electron blocking layer, thereby forming a light emitting layer.

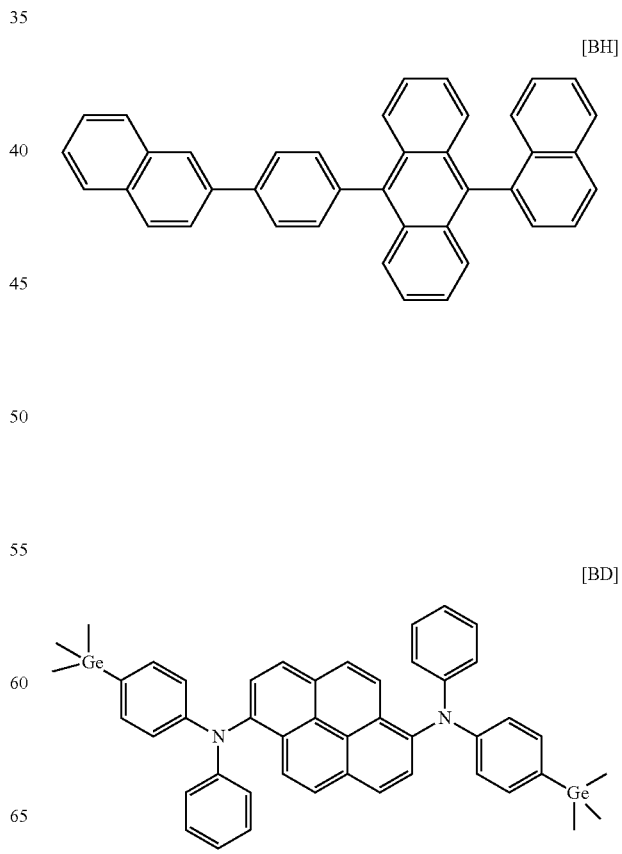
[BH]

[BD]

[R-1]

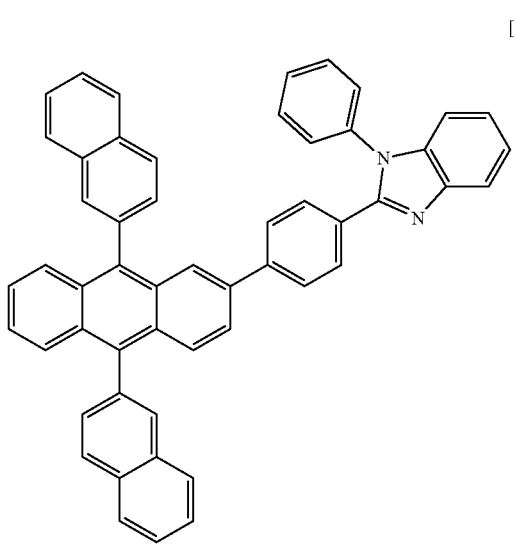

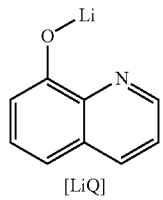

[LiQ]

Compound R-1 and Compound LiQ (lithium quinolate) were vacuum deposited at a weight ratio of 1:1 on the light emitting layer, thereby forming an electron injection and transporting layer having a thickness of 300 Å. Lithium fluoride (LiF) and aluminum were sequentially deposited on the electron injection and transporting layer to have a thickness of 12 Å and 2,000 Å, respectively, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

ET-2

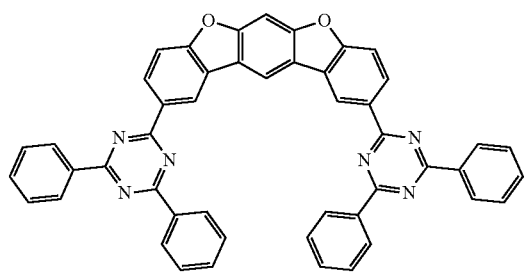

ET-3

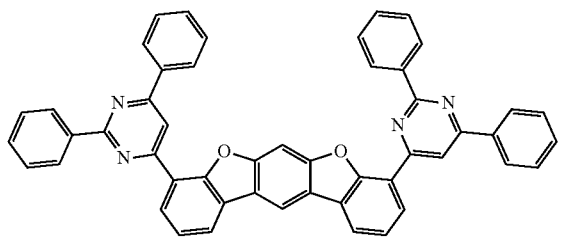

ET-4

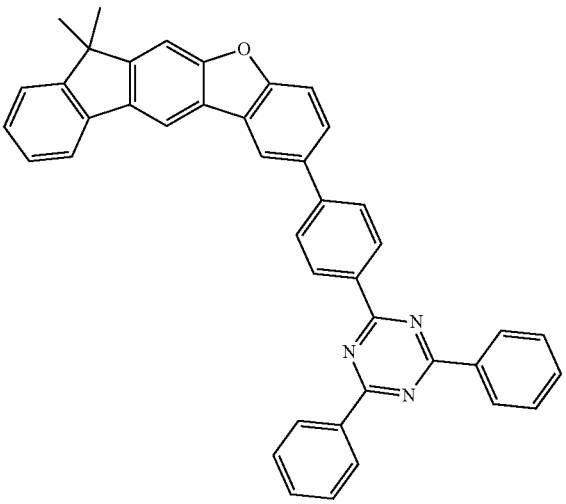

ET-5

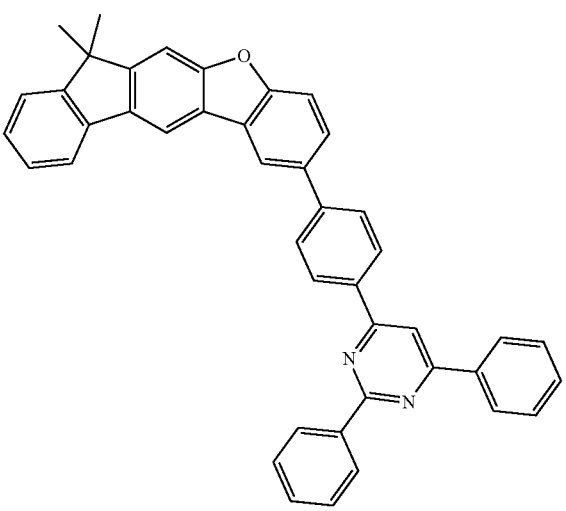

-continued

ET-6

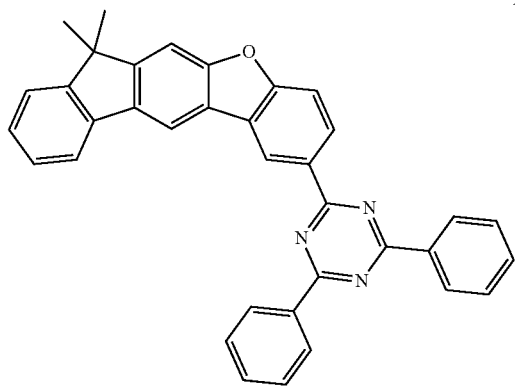

Comparative Example 5-1

An organic light emitting device was manufactured in the same manner as in Comparative Example 5, except that Compound ET-2 was used instead of R-1 in Comparative Example 5.

Comparative Example 5-2

An organic light emitting device was manufactured in the same manner as in Comparative Example 5, except that Compound ET-3 was used instead of R-1 in Comparative Example 5.

Experimental Example 5-1

An organic light emitting device was manufactured in the same manner as in Comparative Example 5, except that Compound ET-4 was used instead of R-1 in Comparative Example 5.

Experimental Example 5-2

An organic light emitting device was manufactured in the same manner as in Comparative Example 5, except that Compound ET-5 was used instead of R-1 in Comparative Example 5.

Experimental Example 5-3

An organic light emitting device was manufactured in the same manner as in Comparative Example 5, except that Compound ET-6 was used instead of R-1 in Comparative Example 5.

For the organic light emitting devices manufactured by Comparative Examples 5-1 and 5-2 and Experimental Examples 5-1 to 5-3, the voltages, current densities, luminances, color coordinates, and service lives were measured, and the results are shown in the following [Table 5]. T95 means the time taken for the luminance to be reduced to 95% of the initial luminance (5,000 nit).

TABLE 5

| | Compound | Voltage (V@10 mA/cm$^2$) | Efficiency (cd/A@10 mA/cm$^2$) | Color coordinate (x, y) | T95 (hr) |
|---|---|---|---|---|---|
| Comparative Example 5 | R-1 | 4.12 | 6.16 | (0.137, 0.126) | 330 |

TABLE 5-continued

| | Compound | Voltage (V@10 mA/cm$^2$) | Efficiency (cd/A@10 mA/cm$^2$) | Color coordinate (x, y) | T95 (hr) |
|---|---|---|---|---|---|
| Comparative Example 5-1 | ET-2 | 4.19 | 6.35 | (0.137, 0.127) | 265 |
| Comparative Example 5-2 | ET-3 | 4.26 | 6.29 | (0.137, 0.126) | 275 |
| Experimental Example 5-1 | ET-4 | 3.74 | 6.47 | (0.137, 0.126) | 380 |
| Experimental Example 5-2 | ET-5 | 3.75 | 6.47 | (0.137, 0.126) | 380 |
| Experimental Example 5-3 | ET-6 | 3.86 | 6.35 | (0.137, 0.127) | 390 |

As seen in Table 5, the organic light emitting device manufactured by using the compound of the present invention having a fluorene core, in which benzofuran is fused, as an electron transporting layer exhibits excellent characteristics in terms of efficiency, driving voltage, and/or stability of the organic light emitting device. The organic light emitting device exhibits lower voltage, higher efficiency, and longer service life characteristics than the organic light emitting devices in Comparative Examples 5-1 and 5-2 manufactured by a compound having a dibenzofuran core, in which benzofuran is fused, as an electron transporting layer.

In Table 5, it can be confirmed that Experimental Examples 5-1 to 5-3 in which a compound in which 'triazine or pyrimidine' is bonded to the core structure (a fluorene in which benzofuran is fused) of Chemical Formula 1 of the present application is used are better in terms of voltage, efficiency, and service life (T95: the time taken for the luminance to be reduced to 95% of the initial luminance) than Comparative Examples 5-1 and 5-2 in which a compound in which 'triazine or pyrimidine' is bonded to dibenzofuran, in which benzofuran is fused, is used.

The compound of the present invention had low voltage characteristics of relatively 10% or more due to the difference in mobilities of the core and served to block electrons from being injected in a barrier with a light emitting layer (the LUMO value is relatively high), thereby obtaining a result that the service life thereof was increased by 15% or more.

Comparative Example 6

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

Hexanitrile hexaazatriphenylene (HAT) of the following Chemical Formula was thermally vacuum deposited to have a thickness of 100 Å on the thus prepared ITO transparent electrode, thereby forming a hole injection layer.

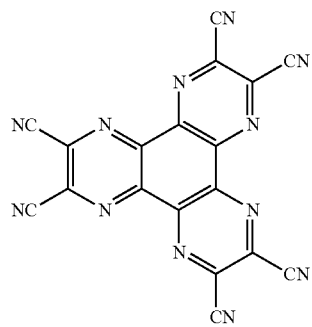

[HAT]

The following compound N-([1,1'-biphenyl]-4-yl)-9,9-dimethyl-N-(4-(9-phenyl-9H-carbazol-3-yl)phenyl)-9H-fluoren-2-amine [HT1] (1,150 Å) being a material for transporting holes was vacuum deposited on the hole injection layer, thereby forming a hole transporting layer.

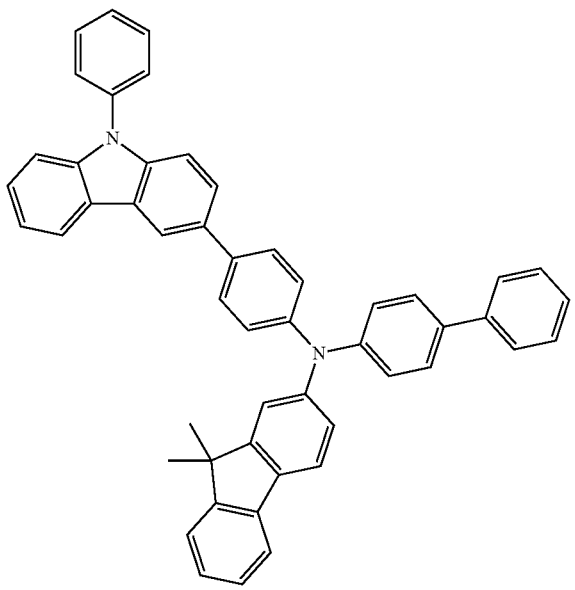 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]

Subsequently, the following compound N,N-di([1,1'-biphenyl]-4-yl)-4'-(9H-carbazol-9-yl)-[1,1'-biphenyl]-4-amine was vacuum deposited to have a film thickness of 150 Å on the hole transporting layer, thereby forming an electron blocking layer.

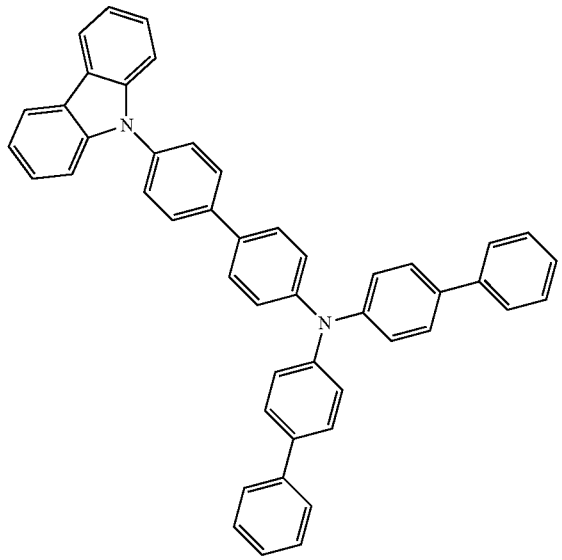

[EBL]

Subsequently, the following GH and GD were vacuum deposited at a weight ratio of 25:1 to have a film thickness of 400 Å on the electron blocking layer, thereby forming a green light emitting layer.

[GH]

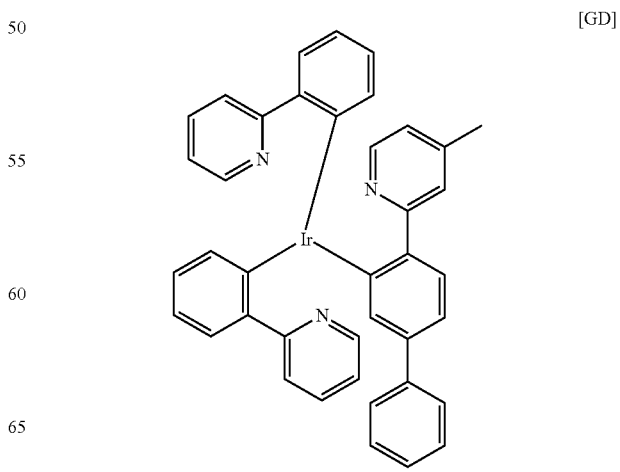

[GD]

[R-2]

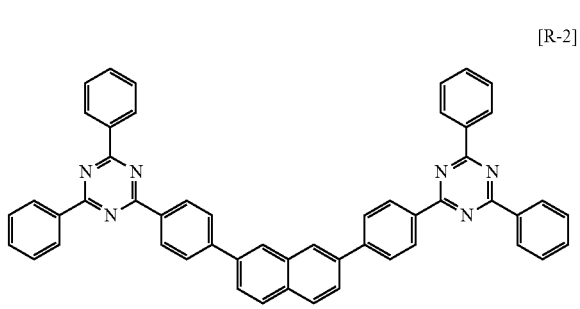

[LiQ]

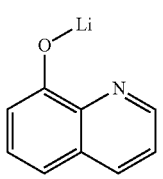

Compound R-2 and Compound LiQ (lithium quinolate) were vacuum deposited at a weight ratio of 1:1 on the light emitting layer, thereby forming an electron injection and transporting layer having a thickness of 360 Å. Lithium fluoride (LiF) and aluminum were sequentially deposited on the electron injection and transporting layer to have a thickness of 12 Å and 2,000 Å, respectively, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2\times10^{-7}$ to $5\times10^{-6}$ torr, thereby manufacturing an organic light emitting device.

ET-4

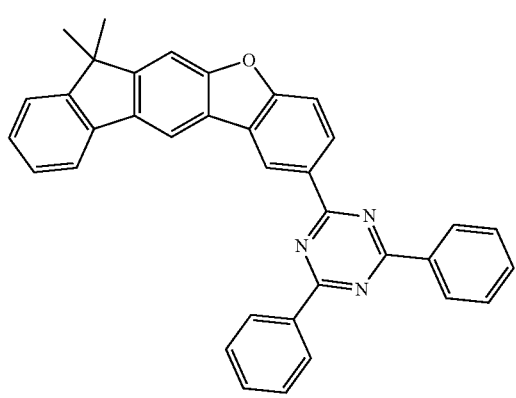

ET-5

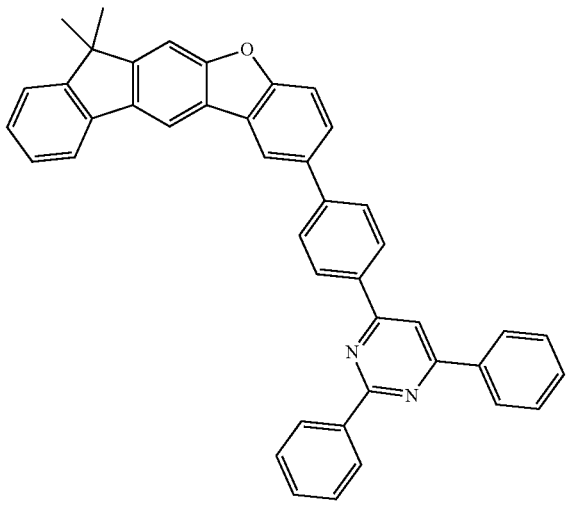

ET-6

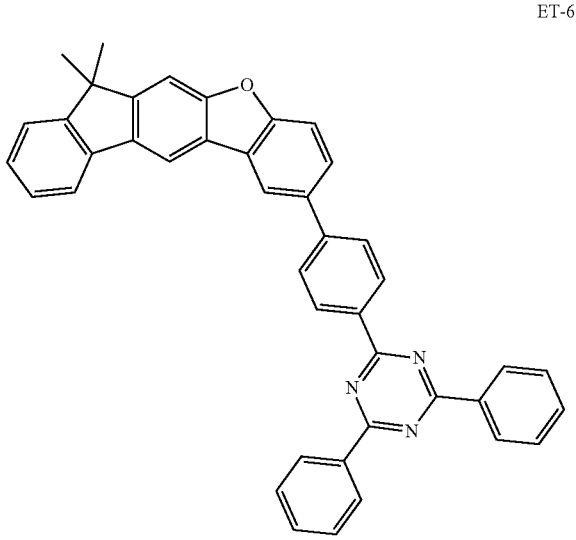

ET-7

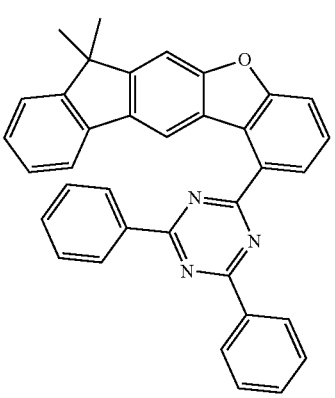

ET-8
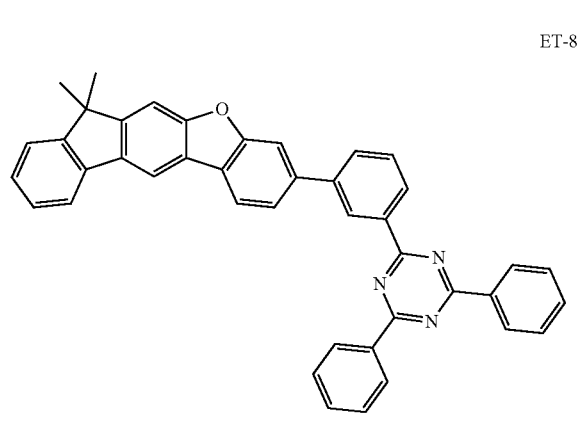
ET-9
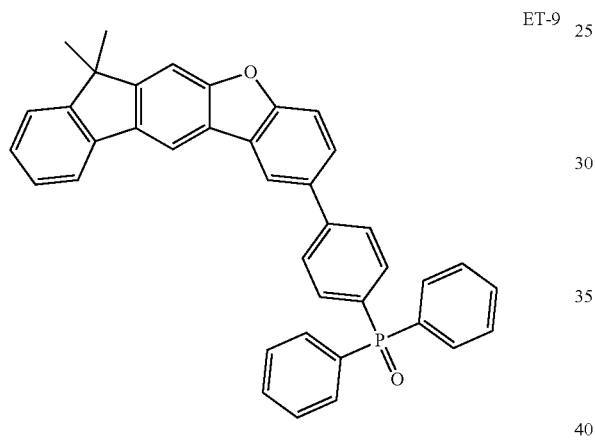
ET-10
ET-11
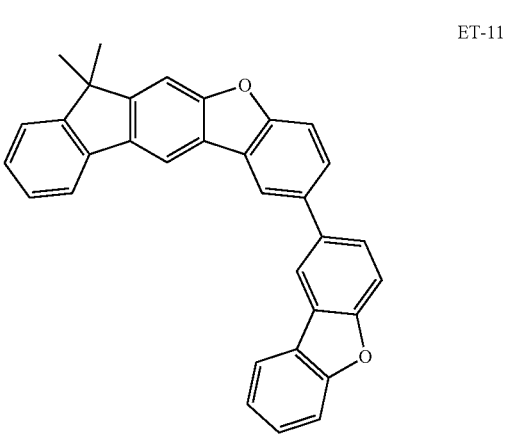
ET-12
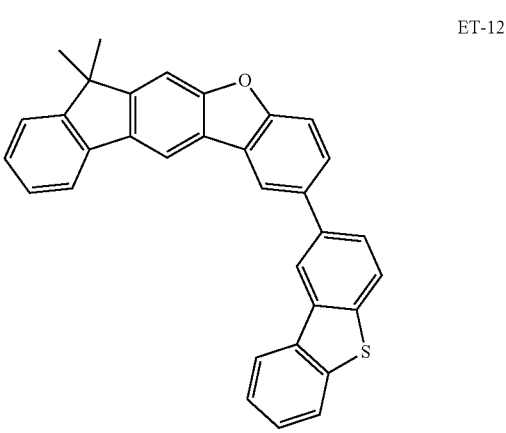
ET-2
ET-3
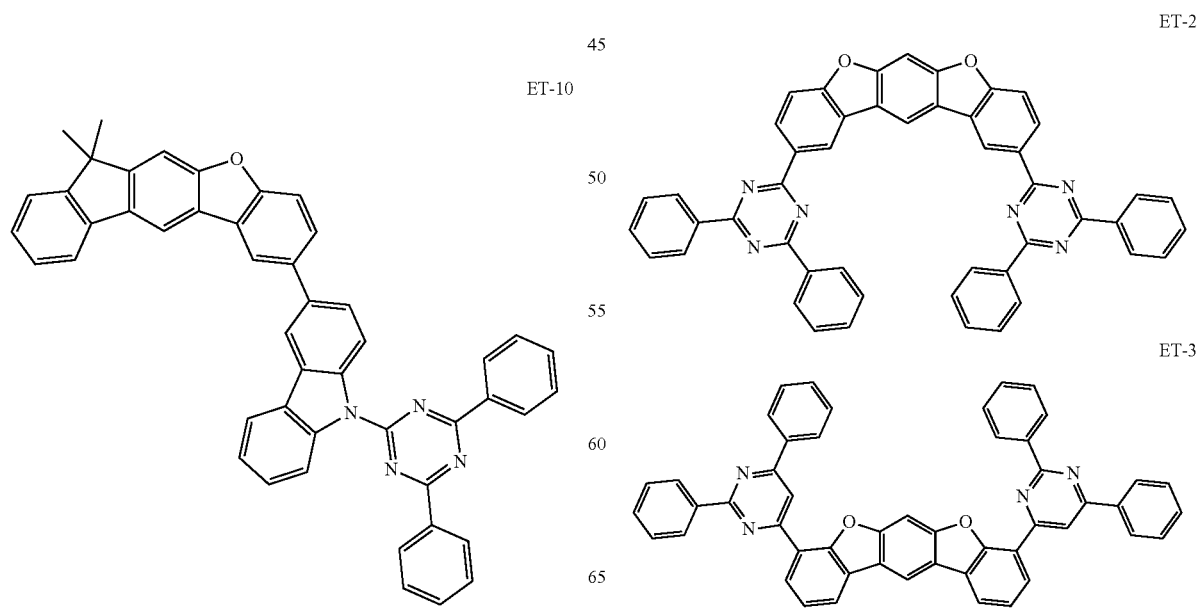

-continued

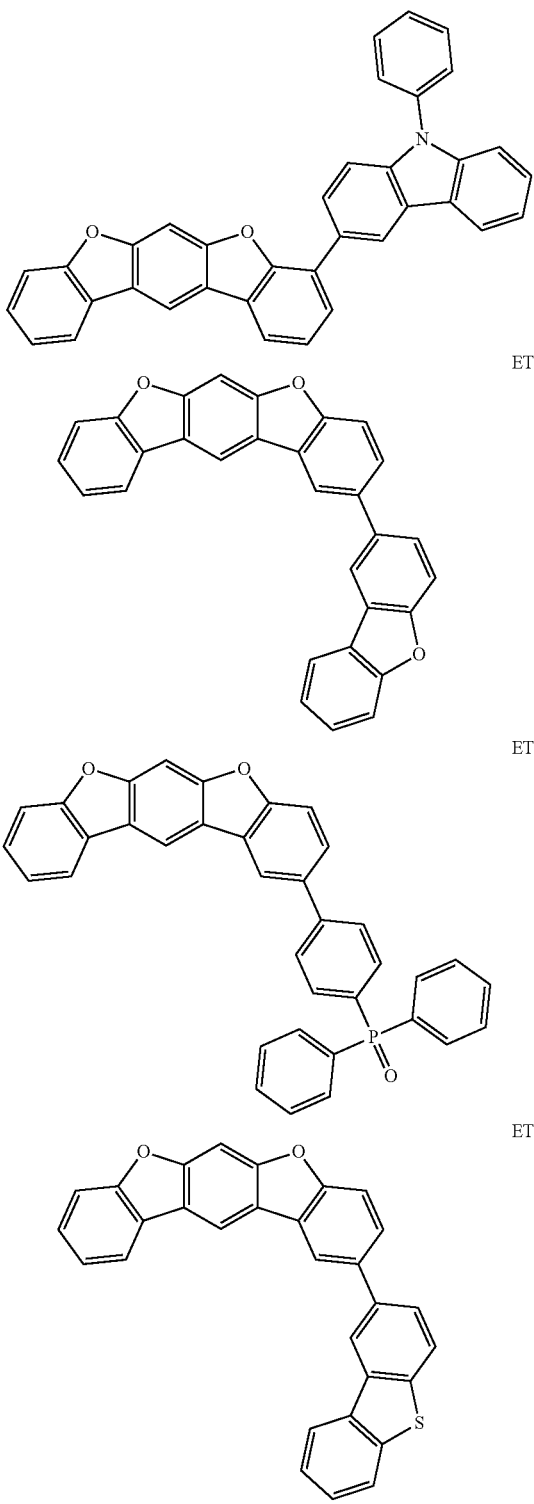

ET-13

ET-14

ET-15

ET-16

Experimental Example 6-1

An organic light emitting device was manufactured in the same manner as in Comparative Example 6, except that Compound ET-4 was used instead of R-2 in Comparative Example 6.

Experimental Example 6-2

An organic light emitting device was manufactured in the same manner as in Comparative Example 6, except that Compound ET-5 was used instead of R-2 in Comparative Example 6.

Experimental Example 6-3

An organic light emitting device was manufactured in the same manner as in Comparative Example 6, except that Compound ET-6 was used instead of R-2 in Comparative Example 6.

Experimental Example 6-4

An organic light emitting device was manufactured in the same manner as in Comparative Example 6, except that Compound ET-7 was used instead of R-2 in Comparative Example 6.

Experimental Example 6-5

An organic light emitting device was manufactured in the same manner as in Comparative Example 6, except that Compound ET-8 was used instead of R-2 in Comparative Example 6.

Experimental Example 6-6

An organic light emitting device was manufactured in the same manner as in Comparative Example 6, except that Compound ET-9 was used instead of R-2 in Comparative Example 6.

Experimental Example 6-7

An organic light emitting device was manufactured in the same manner as in Comparative Example 6, except that Compound ET-10 was used instead of R-2 in Comparative Example 6.

Experimental Example 6-8

An organic light emitting device was manufactured in the same manner as in Comparative Example 6, except that Compound ET-11 was used instead of R-2 in Comparative Example 6.

Comparative Example 6-1

An organic light emitting device was manufactured in the same manner as in Comparative Example 6, except that Compound ET-15 was used instead of R-2 in Comparative Example 6.

Comparative Example 6-2

An organic light emitting device was manufactured in the same manner as in Comparative Example 6, except that Compound ET-2 was used instead of R-2 in Comparative Example 6.

Comparative Example 6-3

An organic light emitting device was manufactured in the same manner as in Comparative Example 6, except that Compound ET-3 was used instead of R-2 in Comparative Example 6.

Comparative Example 6-4

An organic light emitting device was manufactured in the same manner as in Comparative Example 6, except that Compound ET-13 was used instead of R-2 in Comparative Example 6.

Comparative Example 6-5

An organic light emitting device was manufactured in the same manner as in Comparative Example 6, except that Compound ET-14 was used instead of R-2 in Comparative Example 6.

Comparative Example 6-6

An organic light emitting device was manufactured in the same manner as in Comparative Example 6, except that Compound ET-12 was used instead of R-2 in Comparative Example 6.

Comparative Example 6-7

An organic light emitting device was manufactured in the same manner as in Comparative Example 6, except that Compound ET-16 was used instead of R-2 in Comparative Example 6.

For the organic light emitting devices manufactured by Comparative Examples 6-1 to 6-7 and Experimental Examples 6-1 to 6-8, the voltages, current densities, luminances, color coordinates, and service lives were measured, and the results are shown in the following [Table 6]. T95 means the time taken for the luminance to be reduced to 95% of the initial luminance (5,000 nit).

TABLE 6

|  | Compound | Voltage (V@10 Ma/cm$^2$) | Efficiency (cd/A@10 mA/cm$^2$) | T90 (hr) | Color coordinate (x, y) |
|---|---|---|---|---|---|
| Experimental Example 6-1 | ET-4 | 3.93 | 6.15 | 265 | (0.241, 0.715) |
| Experimental Example 6-2 | ET-5 | 3.84 | 5.85 | 285 | (0.242, 0.712) |
| Experimental Example 6-3 | ET-6 | 3.96 | 6.04 | 290 | (0.240, 0.714) |
| Experimental Example 6-4 | ET-7 | 3.81 | 5.92 | 245 | (0.240, 0.716) |
| Experimental Example 6-5 | ET-8 | 3.87 | 6.02 | 265 | (0.241, 0.720) |
| Experimental Example 6-6 | ET-9 | 3.99 | 5.74 | 345 | (0.240, 0.716) |
| Experimental Example 6-7 | ET-10 | 4.29 | 5.84 | 280 | (0.242, 0.711) |
| Experimental Example 6-8 | ET-11 | 4.31 | 5.54 | 220 | (0.240, 0.716) |
| Comparative Example 6-1 | ET-15 | 5.16 | 4.18 | 225 | (0.248, 0.721) |
| Comparative Example 6-2 | ET-2 | 4.42 | 5.27 | 190 | (0.239, 0.719) |
| Comparative Example 6-3 | ET-3 | 4.41 | 5.18 | 195 | (0.249, 0.720) |
| Comparative Example 6-4 | ET-13 | 4.63 | 4.87 | 190 | (0.238, 0.720) |
| Comparative Example 6-5 | ET-14 | 4.84 | 4.64 | 120 | (0.237, 0.711) |
| Comparative Example 6-6 | ET-12 | 4.35 | 5.42 | 230 | (0.242, 0.711) |
| Comparative Example 6-7 | ET-16 | 4.77 | 4.22 | 180 | (0.246, 0.725) |

Table 6 shows the results of Experimental Examples 6-7 and 6-8, in which a compound in which not only triazine and pyrimidine, but also 'carbazole or dibenzofuran' are bonded to the core structure (a fluorene in which benzofuran is fused) of Chemical Formula 1 of the present application is used. Through the result, it can be confirmed that Experimental Examples 6-7 and 6-8 are better in terms of voltage, efficiency, and service life than Comparative Examples 6-4 and 6-5 in which a compound in which 'carbazole or dibenzofuran' is bonded to dibenzofuran, in which benzofuran is fused, is used.

Specifically, since the driving voltages in Experimental Examples 6-7 and 6-8 in which carbazole or dibenzofuran is each bonded to the core structure are 4.29 and 4.31, respectively, but the driving voltages in Comparative Examples 6-4 and 6-5 are 4.63 and 4.84, respectively, the driving voltages in Comparative Examples 6-4 and 6-5 are more increased than those in Experimental Examples 6-7 and 6-8.

Further, since the efficiencies in Experimental Examples 6-7 and 6-8 are 5.84 and 5.54, respectively, but the efficiencies in Comparative Examples 6-4 and 6-5 are 4.87 and 4.64, respectively, it can be confirmed that the case of using the compound of Chemical Formula 1 of the present application has high efficiency.

Comparative Example 7

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

The following compound N4,N4,N4',N4'-tetra([1,1'-biphenyl]-4-yl)-[1,1'-biphenyl]-4,4'-diamine was thermally vacuum deposited to have a thickness of 100 Å on the thus prepared ITO transparent electrode, thereby forming a hole injection layer.

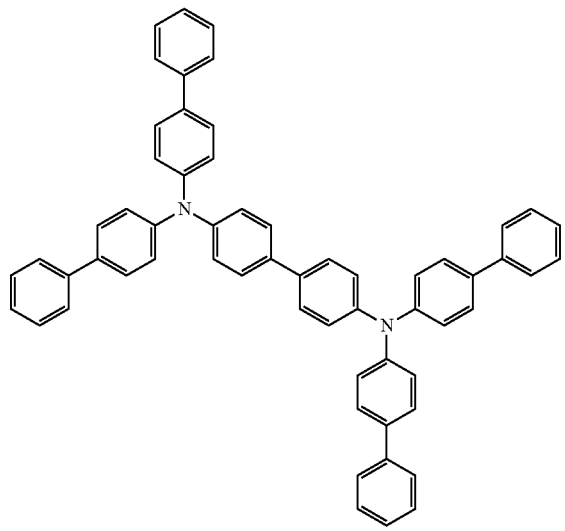 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]

The following compound N-([1,1'-biphenyl]-4-yl)-9,9-dimethyl-N-(4-(9-phenyl-9H-carbazol-3-yl)phenyl)-9H-fluoren-2-amine (1,250 Å) being a material for transporting holes was vacuum deposited on the hole injection layer, thereby forming a hole transporting layer.

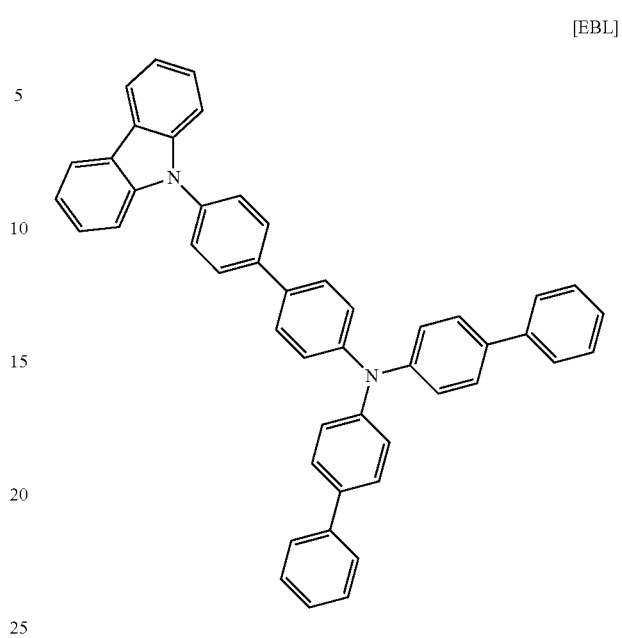
[EBL]

Subsequently, the following BH and BD were vacuum deposited at a weight ratio of 25:1 to have a film thickness of 300 Å on the electron blocking layer, thereby forming a light emitting layer.

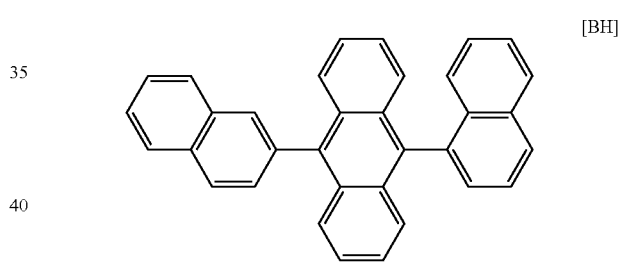
[BH]

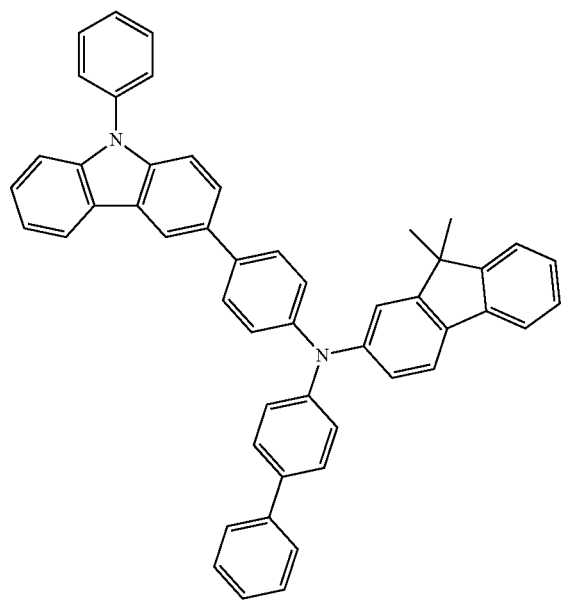 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]

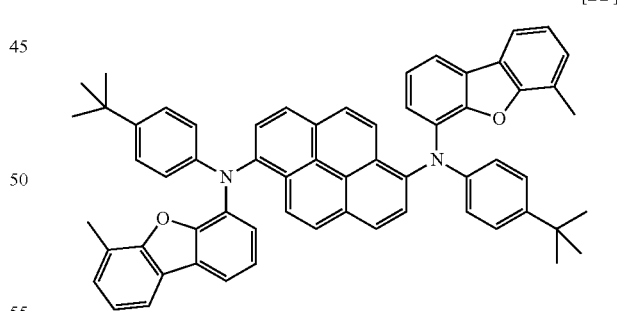
[BD]

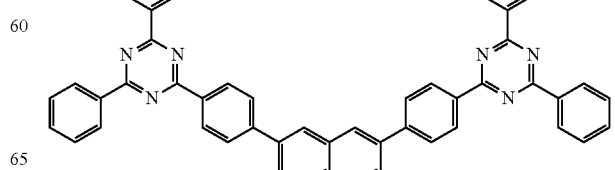
[R-3]

Subsequently, the following compound N,N-di([1,1'-biphenyl]-4-yl)-4'-(9H-carbazol-9-yl)-[1,1'-biphenyl]-4-amine was vacuum deposited to have a film thickness of 150 Å on the hole transporting layer, thereby forming an electron blocking layer.

[LiQ]

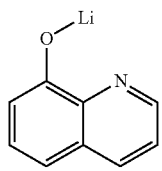

Compound R-3 and Compound LiQ (lithium quinolate) were vacuum deposited at a weight ratio of 1:1 on the light emitting layer, thereby forming an electron injection and transporting layer having a thickness of 360 Å. Lithium fluoride (LiF) and aluminum were sequentially deposited on the electron injection and transporting layer to have a thickness of 12 Å and 2,000 Å, respectively, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

ET-4

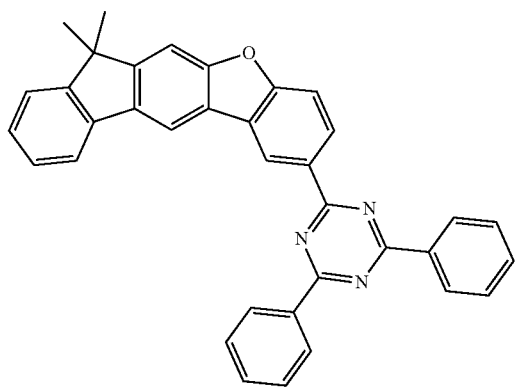

ET-5

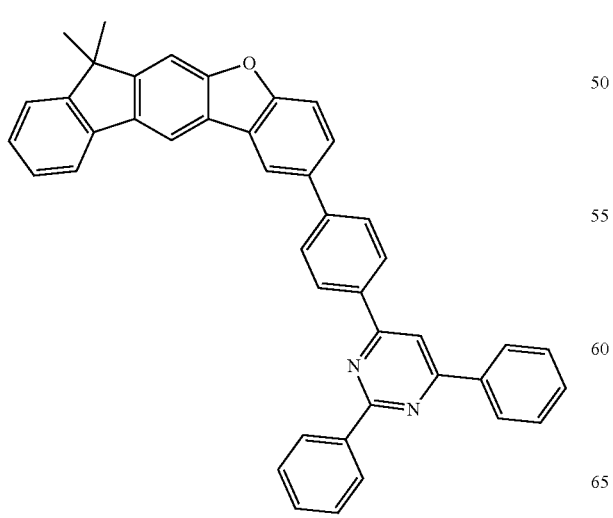

ET-6

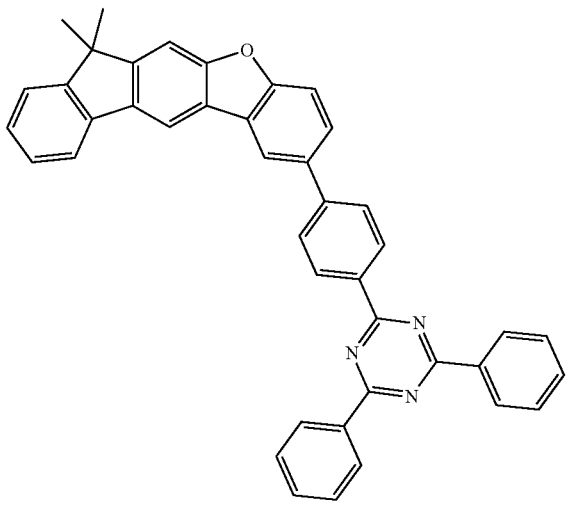

ET-9

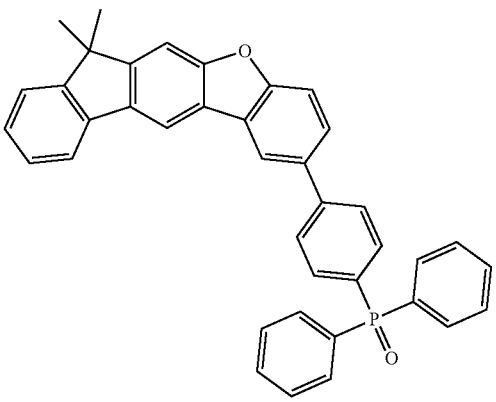

ET-10

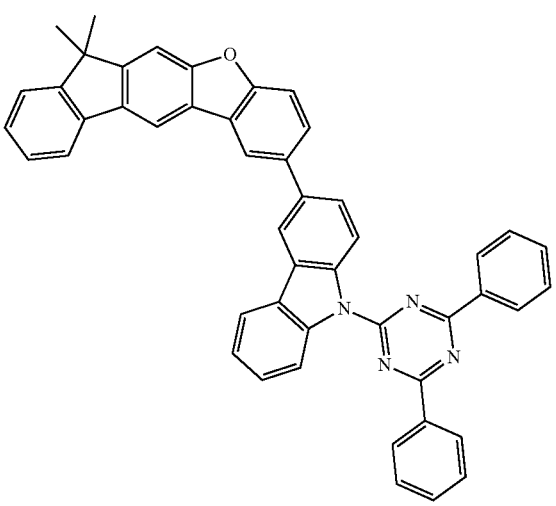

ET-17
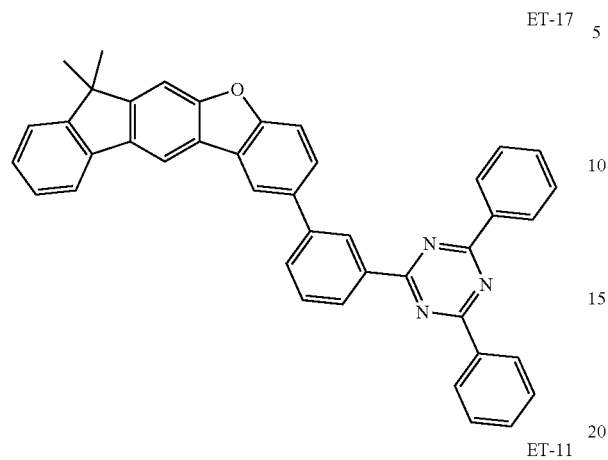
ET-11
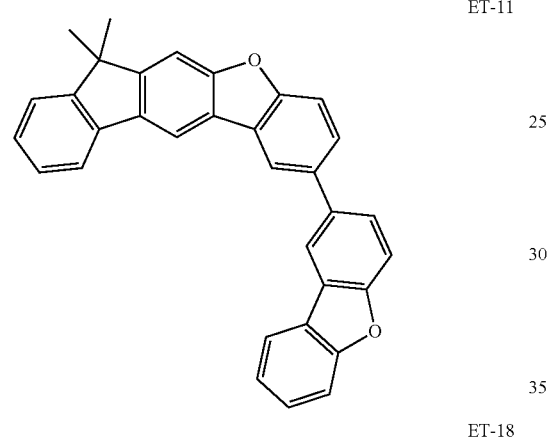
ET-18
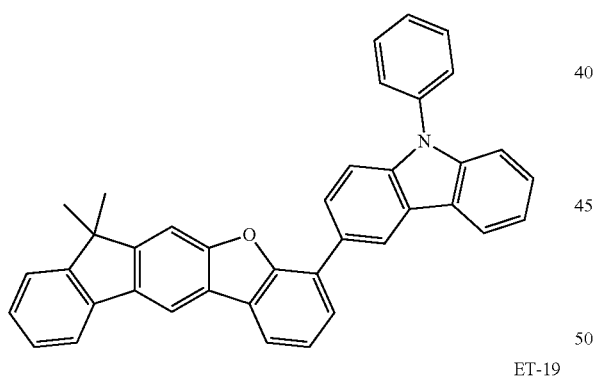
ET-19
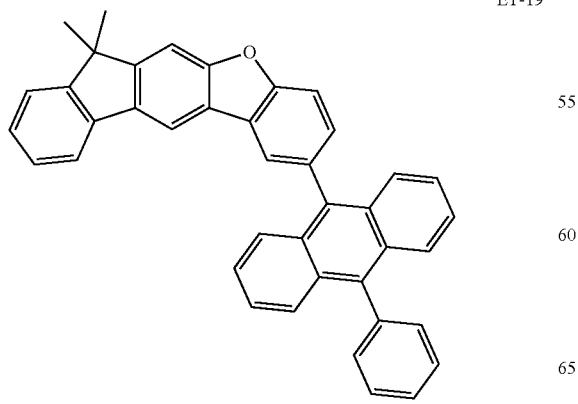
ET-13
ET-14
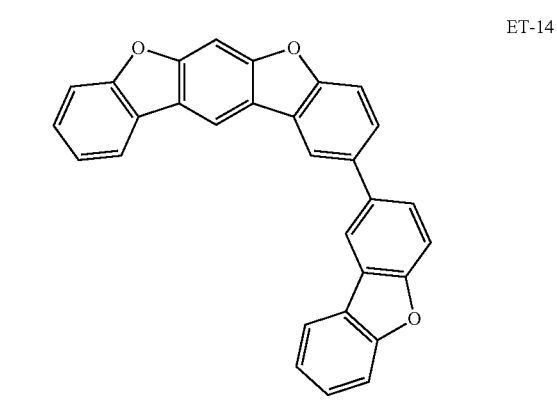
ET-15
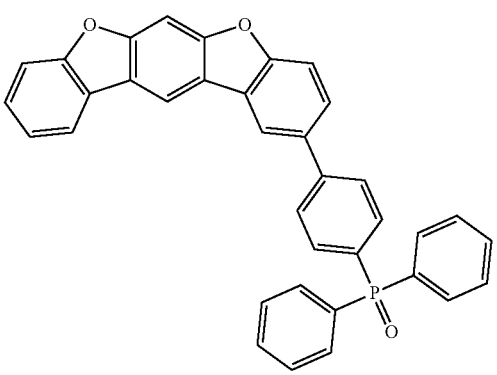
ET-16
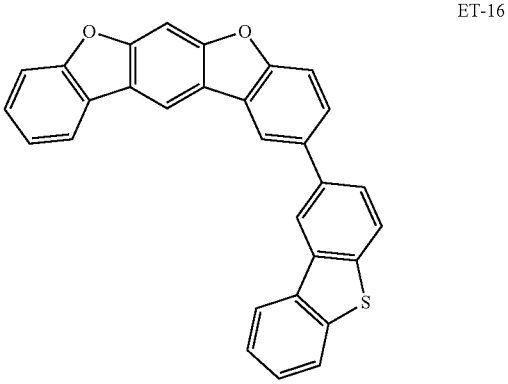

-continued

ET-2

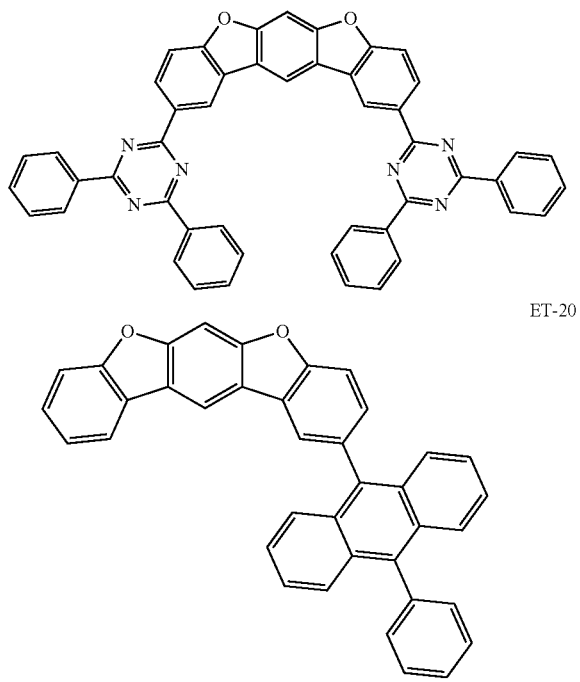

ET-20

Experimental Example 7-1

An organic light emitting device was manufactured in the same manner as in Comparative Example 7, except that Compound ET-4 was used instead of R-3 in Comparative Example 7.

Experimental Example 7-2

An organic light emitting device was manufactured in the same manner as in Comparative Example 7, except that Compound ET-5 was used instead of R-3 in Comparative Example 7.

Experimental Example 7-3

An organic light emitting device was manufactured in the same manner as in Comparative Example 7, except that Compound ET-6 was used instead of R-3 in Comparative Example 7.

Experimental Example 7-4

An organic light emitting device was manufactured in the same manner as in Comparative Example 7, except that Compound ET-9 was used instead of R-3 in Comparative Example 7.

Experimental Example 7-5

An organic light emitting device was manufactured in the same manner as in Comparative Example 7, except that Compound ET-10 was used instead of R-3 in Comparative Example 7.

Experimental Example 7-6

An organic light emitting device was manufactured in the same manner as in Comparative Example 7, except that Compound ET-17 was used instead of R-3 in Comparative Example 7.

Experimental Example 7-7

An organic light emitting device was manufactured in the same manner as in Comparative Example 7, except that Compound ET-11 was used instead of R-3 in Comparative Example 7.

Experimental Example 7-8

An organic light emitting device was manufactured in the same manner as in Comparative Example 7, except that Compound ET-18 was used instead of R-3 in Comparative Example 7.

Comparative Example 7-1

An organic light emitting device was manufactured in the same manner as in Comparative Example 7, except that Compound ET-2 was used instead of R-3 in Comparative Example 7.

Comparative Example 7-2

An organic light emitting device was manufactured in the same manner as in Comparative Example 7, except that Compound ET-13 was used instead of R-3 in Comparative Example 7.

Comparative Example 7-3

An organic light emitting device was manufactured in the same manner as in Comparative Example 7, except that Compound ET-14 was used instead of R-3 in Comparative Example 7.

Comparative Example 7-4

An organic light emitting device was manufactured in the same manner as in Comparative Example 7, except that Compound ET-15 was used instead of R-3 in Comparative Example 7.

Comparative Example 7-5

An organic light emitting device was manufactured in the same manner as in Comparative Example 7, except that Compound ET-16 was used instead of R-3 in Comparative Example 7.

Comparative Example 7-6

An organic light emitting device was manufactured in the same manner as in Comparative Example 7, except that Compound ET-19 was used instead of R-3 in Comparative Example 7.

Comparative Example 7-7

An organic light emitting device was manufactured in the same manner as in Comparative Example 7, except that Compound ET-20 was used instead of R-3 in Comparative Example 7.

For the organic light emitting devices manufactured by Comparative Example 7, Experimental Examples 7-1 to 7-8, and Comparative Examples 7-1 to 7-7, the voltages, current densities, luminances, color coordinates, and service lives were measured, and the results are shown in the following [Table 7]. T95 means the time taken for the luminance to be reduced to 95% of the initial luminance (5,000 nit).

TABLE 7

| | Compound | Voltage (V@10 mA/cm²) | Efficiency (cd/A@10 mA/cm²) | Color coordinate (x, y) | T95 (hr) |
|---|---|---|---|---|---|
| Comparative Example 7 | R-3 | 4.29 | 6.06 | (0.138, 0.050) | 295 |
| Experimental Example 7-1 | ET-4 | 3.86 | 6.20 | (0.141, 0.052) | 355 |
| Experimental Example 7-2 | ET-5 | 3.75 | 6.45 | (0.140, 0.050) | 345 |
| Experimental Example 7-3 | ET-6 | 3.86 | 6.34 | (0.145, 0.049) | 350 |
| Experimental Example 7-4 | ET-9 | 3.75 | 6.57 | (0.144, 0.045) | 420 |
| Experimental Example 7-5 | ET-10 | 3.74 | 6.28 | (0.142, 0.046) | 380 |
| Experimental Example 7-6 | ET-17 | 3.92 | 6.49 | (0.141, 0.044) | 365 |
| Experimental Example 7-7 | ET-11 | 4.08 | 6.09 | (0.145, 0.049) | 325 |
| Experimental Example 7-8 | ET-18 | 4.20 | 6.15 | (0.142, 0.046) | 330 |
| Comparative Example 7-1 | ET-2 | 4.53 | 5.02 | (0.137, 0.044) | 280 |
| Comparative Example 7-2 | ET-13 | 4.76 | 5.34 | (0.141, 0.047) | 215 |
| Comparative Example 7-3 | ET-14 | 4.82 | 5.65 | (0.139, 0.049) | 210 |
| Comparative Example 7-4 | ET-15 | 5.55 | 5.92 | (0.138, 0.048) | 250 |
| Comparative Example 7-5 | ET-16 | 4.76 | 5.66 | (0.137, 0.044) | 225 |
| Comparative Example 7-6 | ET-19 | 4.19 | 6.00 | (0.141, 0.044) | 325 |
| Comparative Example 7-7 | ET-20 | 5.06 | 5.00 | (0.137, 0.044) | 180 |

As seen in Table 7, there are shown the results of Experimental Examples 7-8 and 7-4 in which a compound in which 'N-phenylcarbazole or diphenylphosphine oxide' is bonded to the core structure (fluorene in which benzofuran is fused) of Chemical Formula 1 of the present application is used. Through the result, it can be confirmed that Experimental Examples 7-8 and 7-4 are better in terms of voltage, efficiency, and service life than Comparative Examples 7-2 and 7-4 in which a compound in which 'N-phenylcarbazole or diphenylphosphine oxide' is bonded to dibenzofuran, in which benzofuran is fused, is used.

Specifically, since i) the driving voltages in Experimental Examples 7-8 and 7-4 are 4.20 and 3.75, respectively, but the driving voltages in Comparative Examples 7-2 and 7-4 are 4.76 and 5.55, respectively, ii) the efficiencies in Experimental Examples 7-8 and 7-4 are 6.15 and 6.57, respectively, but the efficiencies in Comparative Examples 7-2 and 7-4 are 5.34 and 5.92, respectively, and iii) the T95 values in Experimental Examples 7-8 and 7-4 are 330 and 420, respectively, but the T95 values in Comparative Examples 7-2 and 7-4 are 215 and 250, respectively, it can be confirmed that the case of using the compound of Chemical Formula 1 of the present application has an excellent effect due to the low driving voltage and high efficiency.

Therefore, it can be confirmed that the case of using a compound in which a substituent of pyrimidine, triazine, carbazole, diphenylphosphine oxide or dibenzofuran is bonded to the core structure (fluorene in which benzofuran is fused) of Chemical Formula 1 of the present application has better efficiency and service life and a lower driving voltage of the organic light emitting device than the case of using a compound in which the substituents are bonded to a dibenzofuran core structure in which benzofuran is fused.

EXPLANATION OF REFERENCE NUMERALS AND SYMBOLS

10, 11: Organic light emitting device
20: Substrate
30: First electrode
40: Light emitting layer
50: Second electrode
60: Hole injection layer
70: Hole transporting layer
80: Electron transporting layer
90: Electron injection layer

The invention claimed is:
1. A hetero-cyclic compound represented by the following Chemical Formula 1:

[Chemical Formula 1]

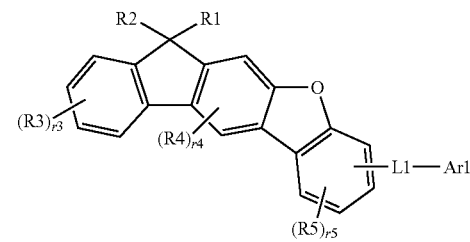

in Chemical Formula 1,
R1 and R2 are the same as or different from each other, and are each independently a substituted or unsubstituted alkyl group,
R3 to R5 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, and
L1 is a direct bond; a substituted or unsubstituted monocyclic or bicyclic arylene group; a substituted or unsubstituted phenanthrenylene group; a substituted or unsubstituted phenalenylene group; a substituted or unsubstituted fluorenylene group; a substituted or unsubstituted polycyclic arylene group, wherein the polycyclic arylene group refers to a cyclic arylene group contains a tetra—or more—cyclic arylene group; or a substituted or unsubstituted heteroarylene group, Ar1 is a substituted or unsubstituted phosphine oxide group; or a substituted or unsubstituted dibenzofuranyl, wherein the heteroaryl group in the heteroarylene group for L1 is a thiophene group, a furanyl group, a pyrrole group, a thiazolyl group, an oxazolyl group, an oxadiazolyl group, a triazolyl group, a quinoxalinyl group, a pyridopyrimidyl group, a pyridopyrazinyl group, a pyrazinopyrazinyl group, a carbazolyl group, a benzimidazolyl group, a benzocarbazolyl group, a benzothiophene group, a dibenzothiophene group, a benzofuranyl group, a phenanthrolinyl group, an isoxazolyl group, a thiadiazolyl group, a phenothiazinyl group, or a dibenzofuranyl group, and when the carbazolyl group is substituted, the carbazolyl group is N-substituted with an unsubstituted phenyl, an unsubstituted naphthyl, or an unsubstituted biphenyl group, provided when Ar1 is a substituted or unsubstituted dibenzofuranyl, the heteroaryl group in the heteroarylene group for L1 is not a carbazolyl group, r3 is an integer from 1 to 4, r4 is 1 or 2, r5 is an integer from 1 to 3, and when r3 to r5 each present in a plural number, a plurality of structures in the parenthesis is the same as or different from each other.

2. The hetero-cyclic compound of claim 1, wherein Chemical Formula 1 is represented the following Chemical Formula 2:

[Chemical Formula 2]

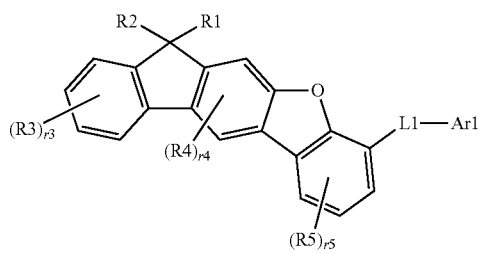

in Chemical Formula 2, the definitions of R1 to R5, r3 to r5, L1, and Ar1 are the same as those in Chemical Formula 1.

3. The hetero-cyclic compound of claim 1, wherein R1 and R2 are the same as or different from each other, and are each independently an unsubstituted alkyl group.

4. The hetero-cyclic compound of claim 1, wherein L1 is a direct bond; a phenylene group; or a heteroarylene group.

5. The hetero-cyclic compound of claim 1, wherein Ar1 is a phosphine oxide group that is substituted with an aryl group; or a dibenzofuranyl that is unsubstituted or substituted with an aryl group, which is unsubstituted or substituted with an alkyl group, or a heteroaryl group.

6. The hetero-cyclic compound of claim 1, wherein Chemical Formula 1 is any one selected from the following compounds:

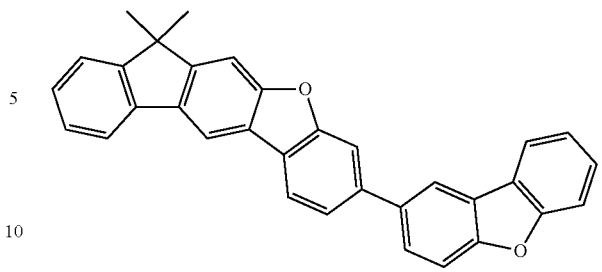

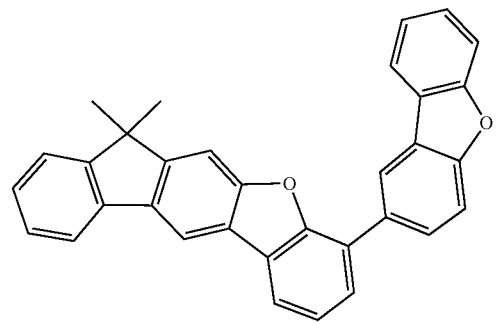

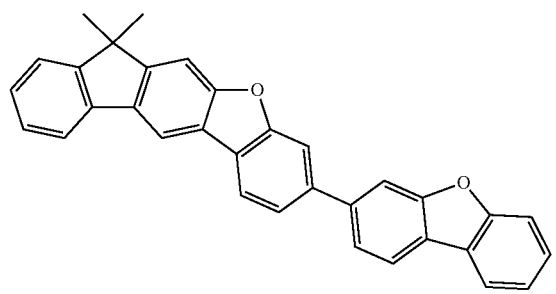

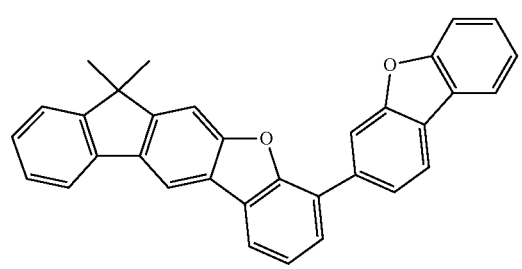

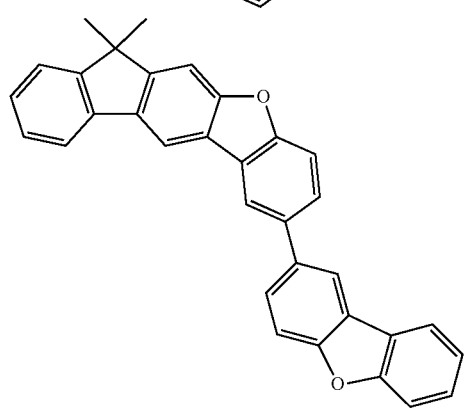

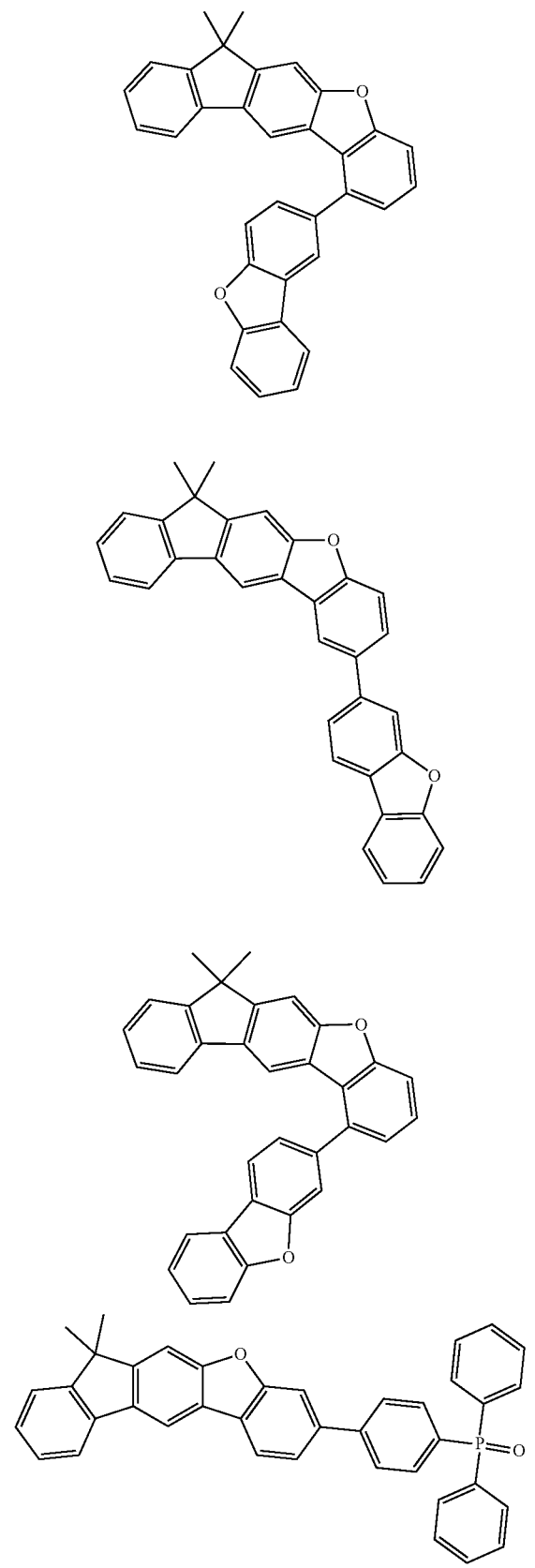
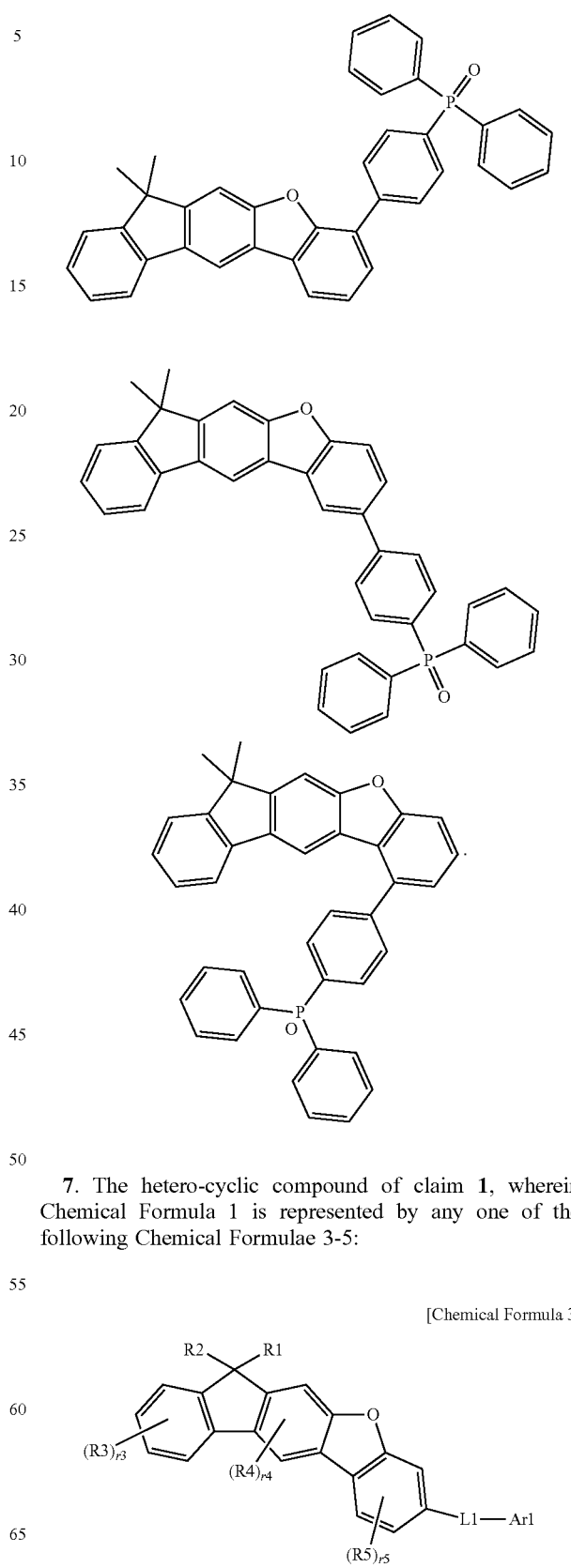
7. The hetero-cyclic compound of claim 1, wherein Chemical Formula 1 is represented by any one of the following Chemical Formulae 3-5:
[Chemical Formula 3]

-continued

[Chemical Formula 4]

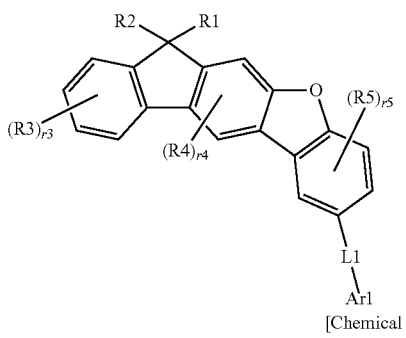

[Chemical Formula 5]

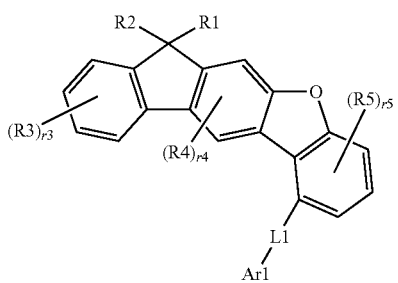

in Chemical Formulae 3 to 5,
the definitions of R1 to R5, r3 to r5, L1, and Ar1 are the same as those in Chemical Formula 1.

8. An organic light emitting device comprising:
a first electrode;
a second electrode disposed to face the first electrode; and
an organic material layer having one or more layers disposed between the first electrode and the second electrode,
wherein the one or more layers of the organic material layer comprise the hetero-cyclic compound of claim 1.

9. The organic light emitting device of claim 8, wherein the organic material layer comprises a hole transporting layer, and the hole transporting layer comprises the hetero-cyclic compound.

10. The organic light emitting device of claim 8, wherein the organic material layer comprises an electron blocking layer, and the electron blocking layer comprises the hetero-cyclic compound.

11. The organic light emitting device of claim 8, wherein the organic material layer comprises an electron transporting layer, and the electron transporting layer comprises the hetero-cyclic compound.

12. The organic light emitting device of claim 8, wherein the organic material layer comprises a light emitting layer, and the light emitting layer comprises the hetero-cyclic compound.

13. The organic light emitting device of claim 8, wherein the organic material layer comprises a light emitting layer, and the light emitting layer comprises the hetero-cyclic compound as a host of the light emitting layer.

* * * * *